US007829688B2

(12) United States Patent
Garry et al.

(10) Patent No.: US 7,829,688 B2
(45) Date of Patent: Nov. 9, 2010

(54) PEPTIDES OF CAV2.2 THAT INHIBIT PAIN

(75) Inventors: Mary Garry, Dallas, TX (US); Ilya Bezprozvanny, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 172 days.

(21) Appl. No.: 12/190,459

(22) Filed: Aug. 12, 2008

(65) Prior Publication Data

US 2009/0068148 A1 Mar. 12, 2009

Related U.S. Application Data

(63) Continuation of application No. 11/096,281, filed on Mar. 31, 2005, now Pat. No. 7,410,950.

(60) Provisional application No. 60/558,383, filed on Apr. 1, 2004.

(51) Int. Cl.
*C07H 21/00* (2006.01)
*C40B 40/06* (2006.01)

(52) U.S. Cl. .......................... 536/23.5; 506/16; 506/17; 536/23.4

(58) Field of Classification Search ....................... None
See application file for complete search history.

(56) References Cited

U.S. PATENT DOCUMENTS

| | | | | |
|---|---|---|---|---|
| 5,429,921 | A | 7/1995 | Harpold et al. | 435/4 |
| 5,792,846 | A | 8/1998 | Harpold et al. | 536/23.1 |
| 5,846,757 | A | 12/1998 | Harpold et al. | 435/29 |
| 5,851,824 | A | 12/1998 | Harpold et al. | 435/325 |
| 6,096,514 | A | 8/2000 | Harpold et al. | 435/69.1 |
| 6,140,485 | A * | 10/2000 | Franco et al. | 536/23.1 |
| 6,229,000 | B1 | 5/2001 | Franz et al. | 536/23.1 |
| 6,353,091 | B1 | 3/2002 | Lipscombe et al. | 530/350 |
| 6,441,156 | B1 | 8/2002 | Lerman et al. | 536/23.5 |
| 6,528,630 | B1 | 3/2003 | Williams et al. | 536/23.1 |
| 6,653,097 | B1 | 11/2003 | Harpold et al. | 435/69.1 |
| 2004/0018510 | A1 | 1/2004 | Harpold et al. | 435/6 |

FOREIGN PATENT DOCUMENTS

| | | |
|---|---|---|
| WO | WO 01/49312 | 7/2001 |
| WO | WO 02/07678 | 1/2002 |
| WO | WO 02/07756 | 1/2002 |
| WO | WO 02/42422 | 5/2002 |
| WO | WO 03/079025 | 9/2003 |
| WO | WO 04/000882 | 12/2003 |

OTHER PUBLICATIONS

Bell et al., "Cell-specific alternative splicing increases calcium channel current density in the pain pathway," *Neuron*, 41:127-138, 2004.

Bell et al., "N-Type calcium currents and $Ca_v2.2^{\alpha}1$ splice isoforms in nociceptive neurons," Program No. 251.11. *2002 Abstract Viewer/Itinerary Planner*. Washington, DC: Society for Neuroscience, 2002. Online.

Bell et al., "N-type $Ca_v2.2\ ^{\alpha}{}_1$ splice variants in nociceptive neurons," *2001 Abstract Viewer/Itinerary Planner*. Washington, DC: Society for Neuroscience, 27(1):998, 2001. Online.

Bezprozvanny and Maximov, "Classification of PDZ domains," *FEB Lett.*, 509:457-462, 2001.

GenBank Accession No. NM 000718, Dec. 23, 2003.

GenBank Accession No. NM 147141, Mar. 2, 2004.

Hatakeyama et al., "Differential nociceptive responses in mice lacking the $\alpha_{1B}$ subunit of N-type $Ca\text{-}^{2+}$ channels," *Neuroreport.*, 12:2423-2427, 2001.

Hibino et al., "RIM binding protein (RBPs) couple Rab3-interacting molecules (RIMs) to voltage-gated $Ca^{2+}$ channels," *Neuron.*, 34:411-423, 2002.

Ho et al., "A role for mints in transmitter release: mint 1 knockout mice exhibit impaired GABAergic synaptic transmission," *Proc. Natl. Acad. Sci. USA*, 100(3):1409-1414, 2003.

Kim et al., "Altered nociceptive response in mice deficient in the $\alpha_{1B}$ subunit of the voltage-dependent calcium channel," *Mol. Cell Neurosci.*, 18:235-245, 2001.

Malmberg and Yaksh, "Effect of continuous intrathecal infusion of ω-conopeptides, N-type calcium-channel blockers, on behavior and antinociception in the formalin and hot-plate tests in rats," *Pain*, 60:83-90, 1995.

Maximov and Bezprozvanny, "Synaptic targeting of No-type calcium channels in hippocampal neurons," *J. Neurosci.*, 22:6939-6952, 2002.

Maximov et al., "Association of neuronal calcium channels with modular adaptor protein," *J. Biol.Chem.*, 274:24453-24456, 1999.

Office Communication, issued in U.S. Appl. No. 11/096,281, dated Jan. 26, 2006.

Office Communication, issued in U.S. Appl. No. 11/096,281, dated Sep. 27, 2007.

Penn and Paice, "Adverse effects associated with the intrathecal administration of ziconotide," *Pain*, 85:291-296, 2000.

Saegusa et al., "Effects of ablation of N- and R-type Ca(2+) channels of pain transmission," *Neuroscience Research*, 43:1-7, 2002.

Saegusa et al., "Lack of No-type calcium channel leads to suppression of inflammatory and neuropathic pain symptoms," *Society for Neuroscience Abstracts*, 27(1):396, 2001.

Saegusa et al., "Suppression of inflammatory and neuropathic pain symptoms in mice lacking the N-type $Ca^{2+}$ channel," *Embo J.*, 20:2349-2356, 2001.

Taverna et al., "Role of lipid microdomains in P/Q-type calcium channel (Cav2.1) clustering and function in presynaptic membranes," *J. Biol. Chem.*, 279:5127-5134, 2003.

* cited by examiner

*Primary Examiner*—Andrew D Kosar
*Assistant Examiner*—Satyanarayana R Gudibande
(74) *Attorney, Agent, or Firm*—Fulbright & Jaworski, L.L.P.

(57) ABSTRACT

The present invention relates to peptides of CaV2.2 and their use in the treatment of pain. The sequence of the peptides is derived from the C-terminus of CaV2.2. and is believed to inhibit the interaction of CaV2.2 with Mint1-PDZ1. The invention is related to use of this peptide to treat pain and to use of this peptide in binding reaction with int-PDZ to screen for small molecules that can inhibit pain.

17 Claims, 7 Drawing Sheets

A

R9-NC = RRRRRRRRRHSYHHPDQDHWC

B

PEPTIDES OF CAV2.2 THAT INHIBIT PAIN

This application is a continuation of U.S. patent application Ser. No. 11/096,281 filed on Mar.31, 2005 now U.S. Pat. No. 7,410,950, which claims the benefit of U.S. Provisional Application No. 60/558,383, filed Apr. 1, 2004. The entire contents of the foregoing applications are hereby incorporated by reference.

This invention was made with government support under Grant No. P50-CA70907 awarded by National Institute of Health. The government has certain rights in the invention.

The government owns rights in the present invention pursuant to grant number NS039552 from the NINDS.

BACKGROUND OF THE INVENTION

1. Field of the Invention

The present invention relates to fields of molecular biology and pathology. More particularly, the present invention relates to peptides of CaV2.2 and methods for their use in the treatment of pain.

2. Description of Related Art

There are six distinguishable types of voltage-dependent calcium channels (VDCC) presently described, designated L-type, N-type, P/Q-type, L-type, R-type, and T-type, which are expressed throughout the nervous system (Tsien et al., 1991). Presynaptic voltage-gated $Ca2^+$ channels mediate rapid $Ca2^+$ influx into the synaptic terminal that triggers synaptic vesicle exocytosis and neurotransmitter release (Llinas et al., 1981). N-type $Ca2^+$ channels, encoded by CaV2.2 pore-forming subunit (Williams et al., 1992; Ertel et al., 2000) and P/Q-type $Ca2^+$ channels, encoded by the CaV2.1 pore-forming subunit (Mori et al., 1991; Ertel et al., 2000), play a predominant role in supporting chemical neurotransmission in central synapses (Takahashi and Momiyama, 1993; Wheeler et al., 1994; Dunlap et al., 1995; Reuter, 1995). Sensation of pain is mediated by nociceptive neurons in the dorsal root ganglia (DRG) (McCleskey and Gold, 1999; Yaksh, 1999). N-type voltage-gated $Ca^{2+}$ channels ($Ca_v2.2$) are abundantly expressed in DRG neurons (Kerr et al., 1988; Gohil et al., 1994; Westenbroek et al., 1998) and play a predominant role in control of glutamate release from DRG neurons in the spinal cord. Thus, inhibition of N-type $Ca^{2+}$ channels is expected to have anti-nociceptive effect. Indeed, studies have suggested that N-type calcium channel antagonists are mainly effective in reducing pain associated with inflammation and tissue/nerve injury, although some effect has been shown in acute models of pain. Anti-nociceptive effects of L- and P/Q-type VDCC antagonists have also been reported; however, these effects appear to be moderate at best.

Pain can be essentially divided into 2 broad categories: physiological pain and pathological pain. Physiological pain is good for the organism in that it is protective. To prevent damage to tissue, physiological pain pathways are activated by noxious stimulation. Physiological pain must only be controlled under specific clinical situations, such as during surgery, medical procedures, or following trauma. Drugs that chronically disable pathways that transmit physiological pain are undesirable as they cause the organism to lose the protective function of pain. Pathological pain, on the other hand, is not the result of a noxious stimulation or healing tissue. Pathological pain originates from abnormal function of the nervous system due to nerve lesion or compression, neuropathy, tumor growth, or tissue inflammation. Current therapeutics that are used for the treatment of pathological pain are typically limited by serious side effects and the development of tolerance.

Pain researchers developed three classes of pain animal models: acute (physiological) pain model (hot plate, tail flick, paw pressure), inflammatory models (carrageenan and formalin), and nerve injury (sciatic nerve ligation, focal spinal injury) (Yaksh, 1999). A biphasic behavioural response is observed in the formalin model. The phase I of the response (1-10 min after injection) corresponds to acute afferent input resulting from the activation of primary afferent neurons. The phase II of the response (10-60 min) results from sensitization of spinal responses and considered to be an appropriate model for persistent pain (Yaksh, 1999).

Consistent with the role of N-type $Ca^{2+}$ channels in pain pathway, pharmacological block of N-type $Ca^{2+}$ channels by single injection or continuos infusion of synthetic ω-conopetide SNX-111 inhibited phase II formalin response in rat animal model (Malmberg and Yaksh, 1994, 1995). The role of N-type $Ca^{2+}$ channels in pain pathway was further supported by analysis of $Ca_v2.2$ knockout mice (Hatakeyama et al., 2001; Kim et al., 2001; Saegusa et al., 2001). All 3 groups observed supression of phase II formalin response in $Ca_v2.2$–/– mice when compared to wild type mice.

These results pointed to N-type $Ca^{2+}$ channels as potential drug target for a treatment of persistent pain. Based on this idea, Elan Pharmaceuticals (initially Neurex) developed a drug Ziconotide (SNX-111, a synthetic version of ω-conotoxin MVIIA). Very promising results were obtained with Ziconitide in clinical trails and currently FDA is considering Ziconotide for approval. However, although Ziconotide is highly effective for treatment of chronic pain, there is also a number of problems associated with its use. Ziconitide (SNX-111) is a polypeptide with a complex chemical structure and very difficult to synthesize. Ziconitide does not pass blood-brain-barrier and has to be delivered by pump infusion directly into a spinal cord, greatly limiting score of its applications. In addition, a number of severe side-effects were reported in some patients in response to Ziconitide (Penn and Paice, 2000).

It has been demonstrated that neuron-to-neuron contact is required for N-type $Ca2^+$ channel clustering during synapse formation in rat hippocampal neuronal culture (Bahls et al., 1998). More recently, synaptic targeting of an auxiliary P/Q-type $Ca2^+$ channel subunitβ4 was investigated (Wittemann et al., 2000). The present inventors have previously investigated targeting of recombinant N-type $Ca2^+$ channels to synaptic locations in rat hippocampal neuronal cultures. It was found that in immature and in mature low-density hippocampal cultures, recombinant N-type $Ca2^+$ channels are uniformly distributed in both axonal and somatodendritic compartments. In contrast, in mature high-density cultures, the recombinant N-type $Ca2^+$ channels are clustered in presynaptic sites and primarily excluded from the somatodendritic domain. Synaptic clustering of recombinant N-type channels depended critically on the most C-terminal region of the "long" splice variant of the N-type $Ca2^+$ channel pore-forming subunit CaV2.2a (Williams et al., 1992; Ertel et al., 2000).

In another earlier study, the inventors identified postsynaptic density-95 (PSD-95)/discs large/zona occludens-1 (PDZ) and Src homology 3 (SH3) domainbinding motifs in the same region of the CaV2.2 subunit (Maximov et al., 1999). The association of CaV2.2-NC1 C termini with the Mint1/CASK/veli-neurexin/neuroligin complex (Maximov et al., 1999) provides a possible molecular mechanism for N-type $Ca2^+$ channel synaptic targeting during synaptogenesis, and the association of CaV2.2a-NC1 C terminal with Mint1-PDZ1 and CASK-SH3 domains (Maximov et al., 1999) links synaptic N-type channels to neurexin-neuroligin neuronal adhesion complex (Irie et al., 1997; Nguyen and Sudhof, 1997; Butz et al., 1998; Song et al., 1999) and synaptic clustering of the channels and synaptic organization (Fanning and Anderson, 1996; Kornau et al., 1997; Craven and Bredt, 1998). The importance of N-type channel association with Mint1 and neurexins is consistent with impaired presynaptic function in neurons from Mint1 kockout (Ho et al., 2003) and α-neurexins (Missler et al., 2003) knockout mice.

More recently, the inventors have shown that CaV2.2 C termini also bind to INADL-5, PAR6, and MUPP1-9 PDZ domains (Bezprozvanny and Maximov, 2001) and that the proline-rich region of the CaV2.2 C-terminus has been implicated recently in interactions with the SH3 domain of RBP (Hibino et al., 2002). Subsequently, the inventors also demonstrated that these motifs act as synergistic synaptic targeting signals for N-type channels in rat hippocampal neurons (Maximov and Bexprozvanny, 2002). The inventors also demonstrated that introduction of CaV2.2 carboxy-terminal sequence into hippocampal neurons by transfection impairs their presynaptic function (Maximov & Bezprozvanny, 2002). However, there have yet to be reported attempts to specifically block these interactions and determine the ensuing biological consequences, particular with regard to pain.

SUMMARY OF THE INVENTION

Thus, in accordance with the present invention, there is provided an isolated and purified peptide of 4 to about 50 residues comprising the sequence DHWC (SEQ ID NO:1), or conservative variants thereof. The peptide may comprises the sequence QDHWC (SEQ ID NO:2), DQDHWC (SEQ ID NO:3), PDQDHWC (SEQ ID NO:4), HPDQDHWC (SEQ ID NO:5), HHPDQDHWC (SEQ ID NO:6), YHHPDQDHWC (SEQ ID NO:7), SYHHPDQDHWC (SEQ ID NO:8) or HSYHHPDQDHWC (SEQ ID NO:9). The peptide may further comprise a permeant protein delivery motif, such as a TAT sequence or an R9 sequence. The peptide may be 40 residues in length, 30 residues in length, 20 residues in length, 15 residues in length, 12 residues in length, 10 residues in length, 8 residues in length, 7 residues in length, 6 residues in length, 5 residues in length, or 4 residues in length. The peptide may be further comprised within a pharmaceutically acceptable buffer, diluent or excipient, or within a lipid vehicle, such as a liposome.

In another embodiment, there is provided a nucleic acid encoding peptide of 4 to about 50 residues comprising the sequence DHWC or conservative variants thereof operably linked to a promoter. The promoter may be tissue specific or constitutive. Constitutive promoters include CMV IE, RSV, and SV40 large T. The nucleic acid may further comprise a polyadenylation signal. The nucleic acid may be located in a viral vector, such as a retrovirus, adenovirus, adeno-associated virus, vaccinia virus, herpesvirus or polyoma virus. The nucleic acid may also be comprised in a non-viral vector, such as a non-viral vector comprised in a lipid vehicle, e.g. a a liposome. The nucleic acid may further encode a permeant protein delivery motif fused to SEQ ID NO:1.

In yet another embodiment, there is provided a method of inhibiting pain in an animal comprising administering to the animal a peptide of 4 to about 50 residues comprising the sequence DHWC (SEQ ID NO:1) or conservative variants thereof, the peptide dispersed in a pharmaceutically acceptable buffer, diluent or excipient. The peptide may be 40 residues in length, 20 residues in length, 12 residues in length, 8 residues in length or 4 residues in length. The peptide may further be comprised within a lipid vehicle, such as a liposome. The pain to be treated may be selected from the group consisting of neuropathic pain, inflammatory pain and pain secondary to cancer. The method may further comprise administering a second anti-pain agent to the animal, such as a steroid, an NTHE, or an opioid. The animal may be a human, a dog, a cat, a rat, a mouse, a horse, a cow or a rabbit.

In still yet another embodiment, there is provided a method of inhibiting pain in an animal comprising administering to the animal a nucleic acid encoding peptide of 4 to about 50 residues comprising the sequence DHWC (SEQ ID NO:1) or conservative variants thereof operably linked to a promoter, the nucleic acid dispersed in a pharmaceutically acceptable buffer, diluent or excipient. The nucleic acid may be located in a viral vector, such as a retrovirus, adenovirus, adeno-associated virus, vaccinia virus, herpesvirus and polyoma virus. The nucleic acid may be comprised in a non-viral vector, such as in a lipid vehicle, e.g., a lipsome. The pain to be treated may be neuropathic pain, inflammatory pain or pain secondary to cancer. The method may further comprise administering a second anti-pain agent to the animal, such as a steroid, an NTHE, or an opioid.

In further embodiments, there are provided methods of screening for an anti-pain agents comprising:

(a) providing a peptide of 4 to about 50 residues comprising the a peptide with one or more conservative variants of DHWC (SEQ ID NO:1);
(b) contacting the peptide with an animal model of pain; and
(c) determining the ability of the peptide to inhibit pain in the animal model, or:

(a) providing a peptide of 4 to about 50 residues comprising the sequence DHWC (SEQ ID NO:1);
(b) contacting the peptide and Mint1, Mint1-PDZ1 domain, Mint2, or Mint2-PDZ1 domain in the presence of a candidate substance; and
(c) determining the ability of candidate substance to inhibit the peptide binding Mint1, Mint1-PDZ1 domain, Mint2, or Mint2-PDZ1 domain, or:

(a) providing a peptide of 4 to about 50 residues comprising the sequence DHWC (SEQ ID NO:1);
(b) contacting said peptide and Mint1-PDZ1/2 domains in the presence of a candidate substance; and
(c) determining the ability of candidate substance to inhibit the peptide bindning Mint1-PDZ1/2 domains, or:

(a) providing a peptide of 4 to about 50 residues comprising the sequence DHWC (SEQ ID NO:1);
(b) contacting said peptide and Mint2 in the presence of a candidate substance; and
(c) determining the ability of candidate substance to inhibit the peptide bindning Mint2, or:

(a) providing a peptide of 4 to about 50 residues comprising the sequence DHWC (SEQ ID NO:1);
(b) contacting said peptide and Mint2-PDZ1 domain in the presence of a candidate substance; and
(c) determining the ability of candidate substance to inhibit the peptide bindning Mint2-PDZ1 domain, or:

(a) providing a peptide of 4 to about 50 residues comprising the sequence DHWC (SEQ ID NO:1);
(b) contacting said peptide and Mint2-PDZ1/2 domains in the presence of a candidate substance; and (c) determining the ability of candidate substance to inhibit the peptide bindning Mint2-PDZ1/2 domains.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Sequence of R9-NC peptide. FIG. 1B. Results of formalin assay in control mouse (n=8) and mouse injected with R9-NC 60 min prior to formalin injection (n=8). Phase I response (1-10 min from formalin injection) and phase II response (11-60 min from formalin injection) are shown.

DESCRIPTION OF ILLUSTRATIVE EMBODIMENTS

Figure 1:
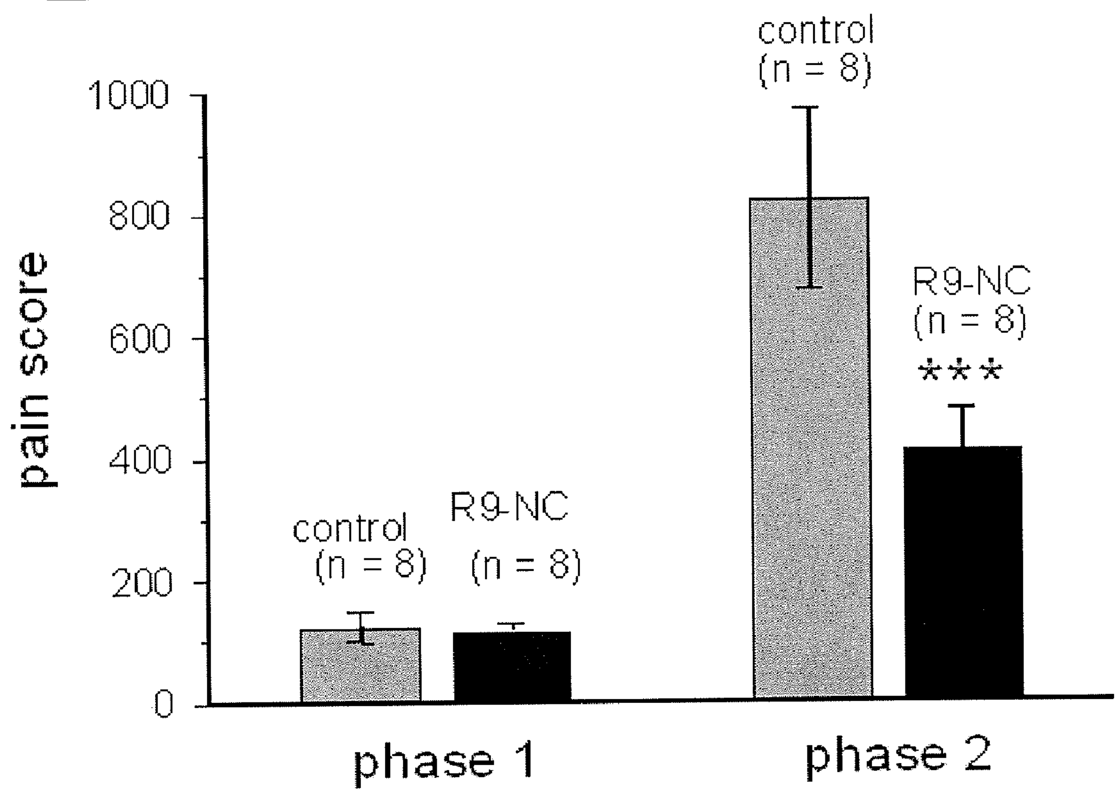
FIGS. 1A & 1B—Supression of phase II, but not phase I formalin response in mouse injected with R9-NC peptide.

As stated above, the inventors reported previously (Maximov et al., 1999) that there was specific association of the CaV2.2 C-terminal region with the first PDZ domain in the neuronal adaptor protein Mint1 and with the SH3 domain of the adaptor protein CASK. More recently, they have shown that CaV2.2 C termini also bind to INADL-5, PAR6, and MUPP1-9 PDZ domains (Bezprozvanny and Maximov, 2001). The proline-rich region of the CaV2.2 C terminal also has been implicated recently in interactions with the SH3 domain of RBP (Hibino et al., 2002). Thus, a number of adaptor proteins appear to play a role in N-type $Ca2^+$ channel synaptic targeting, with Mint1 and CASK being the best candidates for an important interacting role with N-type $Ca2^+$ channel synaptic targeting.

In previous reports, the inventors speculated that the association of CaV2.2-NC1 C termini with the Mint1/CASK/veli-neurexin/neuroligin complex (Maximov et al., 1999) provided a possible molecular mechanism for N-type $Ca2^+$ channel synaptic targeting during synaptogenesis (Maximov and Bezprozvanny, 2002). Here, the inventors now provide evidence that a discrete peptide, derived from the C-terminal region of CaV2.2, can in fact inhibit pain responses in vivo. The synthesis and use of such peptides in the treatment of pain is described in greater detail below.

1. CaV2.2 Peptides or Polypeptides

The present invention relates to the use of C-terminal peptides of CaV2.2. Accession nos. for human and rat CaV2.2 proteins are NM000718 (SEQ ID NO:11) and NM147141 (SEQ ID NO:13), respectively. CaV2.2 is the $\alpha$1B subunit for an N-type $Ca2^+$ channel. It has been localized to the piriform cortex, hippocampus, hypothalamus, locus coeruleus, dorsal raphe, thalamic nuclei, and granular layer of the cortex. The human protein is 2339 residues, and the rat protein is 2333 residues. Each polypeptide concludes with an identical 12 residue sequence of HSYHHPDQDHWC (SEQ ID NO:9), which is a subject of the present invention.

Documents relating to CaV2.2 include U.S. Pat. Nos. 5,429,921, 5,792,846, 5,846,757, 5,851,824, 6,096,514, 6,140,485, 6,229,000, 6,353,091, 6,528,630 and 6,653,097, each of which are hereby incorporated by reference.

A. Structural Features

CaV2.2 peptides will comprise molecules of 4 to about 50 residues in length having the sequence DHWC. A particular preferred length may be less than 35 residues, less than 30 residues, less than 25 residues, less than 20 residues, less than 15 residues, or less than 13, including 4, 5, 6, 7, 8, 9, 10, 11 or 12 residues. The peptides may be generated synthetically or by recombinant techniques, and are purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

The peptides may be labeled using various molecules, such as fluorescent, chromogenic or colorimetric agents. The peptides may also be linked to other molecules, including other anti-pain agents. The links may be direct or through distinct linker molecules. The linker molecules in turn may be subject, in vivo, to cleavage, thereby releasing the agent from the peptide. Peptides may also be rendered multimeric by linking to larger, and possibly inert, carrier molecules.

B. Variants or Analogs of CaV2.2 i) Substitutional Variants

It also is contemplated in the present invention that variants or analogs of CaV2.2 peptides may also inhibit pain. Polypeptide sequence variants of CaV2.2, primarily making conservative amino acid substitutions to SEQ ID NO:1, may provide improved compositions. Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a peptide to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a peptide that defines that peptide's biological functional activity, certain amino acid substitutions can be made in a protein sequence, and its underlying DNA coding sequence, and nevertheless obtain a peptide with like properties. It is thus contemplated by the inventors that various changes may be made in the DNA sequences coding the peptide without appreciable loss of their biological utility or activity, as discussed below.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant peptide, which in turn defines the interaction of the peptide with other molecules.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a peptide with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (±3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide containing molecules that mimic elements of protein secondary structure (Johnson et al, 1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of MBPs, but with altered and even improved characteristics.

ii) Altered Amino Acids

The present invention may employ peptides that comprise modified, non-natural and/or unusual amino acids. A table of exemplary, but not limiting, modified, non-natural and/or unusual amino acids is provided herein below. Chemical synthesis may be employed to incorporated such amino acids into the peptides of interest.

TABLE 1

Modified, Non-Natural and Unusual Amino Acids

| Abbr. | Amino Acid |
|---|---|
| Aad | 2-Aminoadipic acid |
| BAad | 3-Aminoadipic acid |
| BAla | beta-alanine, beta-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| BAib | 3-Aminoisobutyric acid |
| Apm | 2-Aminopimelic acid |

TABLE 1-continued

| Modified, Non-Natural and Unusual Amino Acids | |
|---|---|
| Abbr. | Amino Acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| Aile | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

iii) Mimetics

In addition to the variants discussed above, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

Other approaches have focused on the use of small, multi-disulfide-containing proteins as attractive structural templates for producing biologically active conformations that mimic the binding sites of large proteins (Vita et al., 1998). A structural motif that appears to be evolutionarily conserved in certain toxins is small (30-40 amino acids), stable, and high permissive for mutation. This motif is composed of a beta sheet and an alpha helix bridged in the interior core by three disulfides.

Beta II turns have been mimicked successfully using cyclic L-pentapeptides and those with D-amino acids (Weisshoff et al., 1999). Also, Johannesson et al. (1999) report on bicyclic tripeptides with reverse turn inducing properties.

Methods for generating specific structures have been disclosed in the art. For example, alpha-helix mimetics are disclosed in U.S. Pat. Nos. 5,446,128; 5,710,245; 5,840,833; and 5,859,184. Theses structures render the peptide or protein more thermally stable, also increase resistance to proteolytic degradation. Six, seven, eleven, twelve, thirteen and fourteen membered ring structures are disclosed.

Methods for generating conformationally restricted beta turns and beta bulges are described, for example, in U.S. Pat. Nos. 5,440,013; 5,618,914; and 5,670,155. Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

C. Fusion Proteins

Another variant is a fusion protein. This molecule generally has all or a substantial portion of the original molecule, in this case a peptide comprising the sequence DHWC (SEQ ID NO:1), linked at the N- or C-terminus, to all or a portion of a second peptide or polypeptide. For example, fusions may employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. Of particular interest are peptide permeant motifs that improve peptides transfer through membranes. Such mofits include those from TAT and R9:

TAT=RKKRRQRRR (Schwarze et al., 2000; Becker-Hapak et al., 2001; Denicourt and Dowdy, 2003)

R9=RRRRRRRRR (Wender et al., 2000)

There also may be instances where a greater degree of intracellular specificity is desired. For example, with targeting nuclear proteins, RNA, DNA or cellular proteins or nucleic acids that are subsequently processed. Thus, one preferably uses localization sequences for such targets.

Localization sequences have been divided into routing signals, sorting signals, retention or salvage signals and membrane topology-stop transfer signals (Yellon et al., 1992). For example, there are signals to target the endoplasmic reticulum (Munro, et al., 1987), the nucleus (Lanford et al., 1986; Stanton et al., 1986; Harlow et al., 1985), the nucleolar region (Kubota et al., 1989; and Siomi et al., 1988), the endosomal compartment (Bakke et al., 1990), mitochondria (Yellon et al., 1992) and liposomes (Letourneur et al., 1992). One preferred nuclear targeting sequence may be the SV40 nuclear localization signal.

D. Purification of Proteins

It may be desirable to purify MBPs, variants, peptide-mimics or analogs thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and Helix pomatia lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

E. Peptide Synthesis

CaV2.2-related peptides may be generated synthetically for use in various embodiments of the present invention. Because of their relatively small size, the peptides of the invention can be synthesized in solution or on a solid support in accordance with conventional techniques. Various automatic synthesizers are commercially available and can be used in accordance with known protocols. See, for example, Stewart & Young, (1984); Tam et al., (1983); Merrifield, (1986); Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

2. CaV2.2 Nucliec Acids

Important aspects of the present invention concern isolated DNA segments and recombinant vectors encoding CaV2.2 and peptides thereof, the creation and use of recombinant host cells through the application of DNA technology, that express CaV2.2 or peptides thereof, and biologically functional equivalents thereof. Accession nos. for human and rat CaV2.2 DNA sequences are GI4502522 (SEQ ID NO:10) and GI25453409 (SEQ ID NO:12), respectively.

The present invention concerns DNA segments, isolatable from mammalian cells, such as mouse, rat or human cells, that are free from total genomic DNA and that encode a CaV2.2 polypeptide or peptide. As used herein, the term "DNA segment" refers to a DNA molecule that has been isolated free of total genomic DNA of a particular species. Therefore, a DNA segment encoding CaV2.2 refers to a DNA segment that contains wild-type, polymorphic or mutant CaV2.2 coding sequences yet is isolated away from, or purified free from, total mammalian genomic DNA. Included within the term "DNA segment" are DNA segments and also recombinant vectors, including, for example, plasmids, cosmids, phage, viruses, and the like.

A. CaV2.2 Splice Forms

Human (Williams et al., 1992), chicken (Lu and Dunlap, 1999), and rat (Maximov and Bezprozvanny, 2002) CaV2.2 subunits undergo alternative splicing in the C-terminal region. The results suggest that in mature high density cultures, the long CaV2.2a-NC1 splice variant (CaV2.2a) is the axonal/presynaptic isoform, and the short CaV2.2a-NC2 splice variant (CaV2.2b) is the somatodendritic isoform (Maximov and Bezprozvanny, 2002). Similar to the CaV2.2 subunit, the P/Q-type channel pore-forming subunit CaV2.1 is alternatively spliced at the C termini (Zhuchenko et al., 1997).

The long C-terminal splice variant of CaV2.1a, but not the short splice variants, contains a similar PDZ domainbinding motif (Maximov et al., 1999). The inventors have previously suggested that the N-type and the P/Q-type $Ca2^+$ channels are targeted to synapses via interactions with a similar or identical set of adaptor proteins (Maximov and Bezprozvanny, 2002). The also have suggested that an alternative splicing of the CaV2.2 and CaV2.1 subunit C termini provides a potential regulatory mechanism of N-type and P/Q-type $Ca2^+$ channel sorting (Maximov and Bezprozvanny, 2002). In the case of P/Q-type $Ca2^+$ channels, association of CaV2.1 C terminal with an auxiliary β4 subunit (Walker et al., 1998) may play an additional role in synaptic targeting (Wittemann et al., 2000). It is also possible that truncation of SH3, PDZ, and β4 binding motifs in the CaV2.1 subunit (Fletcher et al., 1996) may lead to mistargeting of P/Q-type $Ca2^+$ channels in leaner mice, resulting in severe neurological phenotype.

A recent report suggested the importance of alternative splicing in the CaV2.1 subunit II/III loop region for P/Q-type $Ca2^+$ channel sorting between axonal and somatodendritic compartments of GABAergic cortical neurons (Timmermann et al., 2002). Novel II/III splice variants of human CaV2.2 subunit that lack the soluble SNARE-binding synprint site were identified recently (Kaneko et al., 2002). At the moment it is not clear whether alternative splicing of the CaV2.2 and CaV2.1 II/III loop and C-terminal regions are independent or correlated events, and future studies will be needed to answer this question. However, these data suggest that the alternative splicing-dependent sorting of $Ca2^+$ channels in neurons may be a general phenomenon.

B. Variants

In particular embodiments, the invention concerns isolated DNA segments and recombinant vectors incorporating DNA sequences that encode a CaV2.2, a peptide, peptide-mimic or a biologically functional equivalent of a CaV2.2. The term "biologically functional equivalent" is well understood in the art and is further defined in detail herein. Accordingly, sequences that have about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, about 70% to about 80%, and more preferably about 81% and about 90%; or even more preferably, between about 91% and about 99%; of amino acids that are identical or functionally equivalent to the amino acids of SEQ ID NO:1 or any analog or variant thereof provided the biological activity of the protein is maintained. In particular embodiments, the biological activity of a CaV2.2 C-terminal peptide, or a biologically functional equivalent, comprises binding to Mint1.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein, polypeptide or peptide activity where an amino acid sequence expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

3. Screening Assays

The present invention also contemplates the screening of compounds, e.g., peptides, peptide-mimics, variants, analogs or small molecules, for various abilities to interact with Mint1 and/or affect pain signaling in an animal model of pain. Particularly preferred compounds will be those that mimic the function of the CaV2.2 C-terminal peptide disclosed herein. In the screening assays of the present invention, the candidate substance may first be screened for basic biochemical activity—e.g., binding to a target molecule (e.g., Mint1)—and then tested for its ability to inhibit pain at the whole animal level.

A. Modulators

The present invention provides methods of screening for agents that bind Mint1. In an embodiment, the present invention is directed to a method of:

(a) providing a Mint1, Mint1-PDZ1, Mint2, or Mint2-PDZ1 polypeptide;

(b) contacting the Mint1, Mint1-PDZ1, Mint2, or Mint2-PDZ1 polypeptide with a candidate substance; and (c) determining the binding of the candidate substance to the Mint1, Mint1-PDZ1, Mint2, or Mint2-PDZ1 polypeptide, wherein binding to Mint1 identifies the compound as a putative anti-pain agent. Measuring binding to Mint1 may be direct, by identifying a Mint1-candidate complex, by identifying labeled candidate associated with Mint1, or by assessing the inhibition of binding of a peptide comprising SEQ ID NO:1 to Mint1 by the candidate. In still yet other embodiments, one would look at the effect of a candidate on pain in an appropriate model.

As used herein, the term "candidate substance" refers to any molecule that may potentially modulate bind to Mint1 in a manner analogous to a peptide having the sequence of SEQ ID NO:1. The candidate substance may be a peptide, or a small molecule inhibitor, or even a nucleic acid molecule. It may prove to be the case that the most useful pharmacological compounds will be compounds that are structurally related to compounds which interact naturally with Mint1. Creating and examining the action of such molecules is known as "rational drug design," and include making predictions relating to the structure of target molecules.

The goal of rational drug design is to produce structural analogs of biologically active polypeptides or target compounds. By creating such analogs, it is possible to fashion drugs which are more active or stable than the natural molecules, which have different susceptibility to alteration or which may affect the function of various other molecules. In one approach, one would generate a three-dimensional structure for a molecule like Mint1, and then design a molecule for its ability to interact with Mint1. This could be accomplished by x-ray crystallography, computer modeling or by a combination of both approaches.

It also is possible to use antibodies to ascertain the structure of a target compound or inhibitor. In principle, this approach yields a pharmacore upon which subsequent drug design can be based. An example of such an approach is to use a peptide of SEQ ID NO:1 as a model, and then make modifications that would improve the ability of the molecule to bind Mint1.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds or may be found as active combinations of known compounds which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be a polypeptide, polynucleotide, small molecule inhibitor or any other compounds that may be designed through rational drug design starting from known inhibitors of hypertrophic response.

It will, of course, be understood that all the screening methods of the present invention are useful in themselves notwithstanding the fact that effective candidates may not be found. The invention provides methods for screening for such candidates, not solely methods of finding them.

B. In Vitro Assays

A quick, inexpensive and easy assay to run is a Mint1 binding assay. Binding of a molecule to Mint1 may, in and of itself, be inhibitory, due to steric, allosteric or charge-charge interactions. This can be performed in solution or on a solid phase and can be utilized as a first round screen to rapidly eliminate certain compounds before moving into more sophisticated screening assays.

The target (e.g., Mint1) may be either free in solution, fixed to a support, expressed in or on the surface of a cell. Either the target or the compound may be labeled, thereby permitting determination of binding. Competitive binding assays can be performed in which a peptide comprising SEQ ID NO:1 is used. The peptide may be labeled, or the candidate may be labeled. One may measure the amount of free label versus bound label to determine binding or inhibition of binding.

A technique for high throughput screening of compounds is described in WO 84/03564. Large numbers of small peptide test compounds are synthesized on a solid substrate, such as plastic pins or some other surface. The peptide test compounds are reacted with, for example, Mint1 and washed. Bound polypeptide is detected by various methods.

To search for small molecule inhibitors of association between CaV2.2 carboxy-terminal and Mint1-PDZ1 domain, the inventors will utilize a variety of different approaches. First, they will synthesize biotinylated CaV2.2a N-type $Ca^{2+}$ channels carboxy-terminal peptide and express Mint1-PDZ1 domain in bacteria as GST-fusion protein. Next, two methods are contemplated for use in high throughput screens—a scintillation-proximity assay (SPA) and a homogeneous time-resolved fluorescence resonance energy transfer assay (HTRF) (see Whitfield et al., 2003). These methods will be used to screen an 8,000 compound subset selected from a compound library available at UT Southwestern HTS facility. SPA and HTRF pilot screens will be optimized to yield Z score (Zhang et al., 1999) of at least 0.5 with the test library of 8,000 compounds. Identified compounds (hits) will be validated in formalin-induced pain model (Malmberg and Yaksh, 1995).

i) Z Score Determination

Pilot studies will provide the inventors with initial information if SPA and/or HTRF assays can be used to analyze association of bio-NC peptide and GST-Mint1-PDZ1 protein. Recently developed simple statistical parameter (Z score) can be used for evaluation of high throughput screens (Zhang et al., 1999). According to Zhang et al. (1999), in order to validate a quality of proposed high throughput screens, one has to calculate a ratio of separation band to the signal dynamic range of the assay. Obtained parameter (Z factor) defines the capability of hit identification for each given high throughput screens at the defined screening conditions.

As a first step of high throughput screen optimization, Zhang et al. (1999) recommend to determine Z' factor that is calculated similar to Z factor using only control data. The Z' factor is a characteristic parameter for the quality of assay itself, without intervention of any test compounds. In order to determine Z' score, the inventors will measure SPA signal or HTRF signal for each well of 3 384 well plates with bio-NC peptide and GST-Mint1-PDZ1 protein. These measurements will be analyzed to yield $\mu_{C+}$ (mean positive signal) and $\sigma_{C+}$ (variablity of positive signal). They will also measure SPA signal or HTRF signal for each well of 3 384 well plates with bio-NC-W2338A peptide and GST-Mint1-PDZ1 protein. As NC-W2338A mutant does not bind to Mint1-PDZ1, these measurements will provide us with $\mu_{C-}$ (mean negative signal) and $\sigma_{C-}$ (variablity of negative signal).

Once these values are obtained, the inventors will calculate Z' score using formula from (Zhang et al., 1999):

$$Z'=1-(3\sigma_{C+}+3\sigma_{C-})/|\mu_{C+}-\mu_{C-}| \quad \text{(eq 1)}$$

If the inventors obtain Z'>0.5 for SPA and/or HTRF assay, they will proceed with pilot screen using 8,000 test compound library. If Z'<0.5 for either assay, the screen will be optimized to result in Z'>0.5. The optimization steps for SPA assay include optimization of SPA beads concentration, replacement of PVT beads with Ysi beads, optimization of $^{35}$S-Streptavidin concentration, optimization of bio-NC peptide and GST-Mint1-PDZ1 protein amounts, dilution of samples prior to SPA counting, changes in incubation time and temperature, change in agitation, etc. The optimization steps for HTRF assay include changes in EuK-anti-GST-mAb and Streptavidin-XL concentrations, changes in number of flashes per well and in HTRF integration time, optimization of bio-NC peptide and GST-Mint1-PDZ1 protein amounts, dilution of samples prior to HTRF counting, changes in incubation time and temperature, change in agitation, etc.

Once Z'>0.5 condition is met, the inventors will fix the assay conditions and perform a pilot screen with the test library of 8,000 compounds (each at 5 μM concentration) and measure SPA signal and/or HTRF signal for each well containing different test compounds mixed with bio-NC peptide and GST-Mint1-PDZ1 protein. The test library of 8,000 compounds is available at UT Southwestern HTS facility. These measurements will be analyzed to yield $\mu_S$ (mean sample signal) and $\sigma_S$ (variablity of sample signal). As most of test compounds are not expected to disrupt bio-NC peptide association with GST-Mint1-PDZ1 domain, Z-score will be calculated using negative control (bio-NC-W2338A) data as follows (Zhang et al., 1999):

$$Z=1-(3\sigma_S+3\sigma_{C-})/|\mu_S-\mu_{C-}| \quad \text{(eq 2).}$$

Previous HTS screens at UT Southwestern HTS facility with the test library of 8,000 compounds (at 5 μM concentration) resulted in a sample mean within 4% from DMSO control and it is most likely that the HTS screen with Z'>0.5 will yield Z>0.5. If Z>0.5, the inventors can proceed with the complete screen. If Z<0.5, the inventors will need to optimize the concentration of test compounds to yield Z>0.5 but still a resonable "hit rate" (Zhang et al., 1999). The biological activity of the "hits" from the full screen will be tested in formalin-induced pain model (Malmberg and Yaksh, 1995).

ii) Scintillation Proximity Assay

In scintillation-proximity assay (SPA) studies, biotinylated NC peptide (bio-NC) and GST-Mint1-PDZ1 protein will be mixed in SPA buffer (0.2% BSA in PBS) in the presence of 5 μM concentration of tested small molecule compounds in a white 384 well Optiplates (Packard) in a final volume of 25 μl for 1 hour. SPA readout will be initated by addition of Glutathione-PVT SPA beads (RPNQ0030 from Amersham) and $^{35}$S-Streptavidin (Amersham SJ436). The plates will be sealed and incubated for 10 min with shaking. Following incubation, the plates will be spun for 5 min at 1,000 g to float PVT SPA beads and the luminescence signal from each well will be determined by CLIPR luminescence plate reader. Association of bio-NC peptide with GST-Mint1-PDZ1 will bring radiolabeled Streptavidin (bio-NC binding partner) in proximity of Glutathione-PVT SPA beads (GST-binding partner), resulting in strong luminescence signal. Control studies will be performed with bio-NC-W2338A peptide instead of bio-NC peptide. NC-W2338A does not bind Mint1-PDZ1 domain and bio-NC-W2338A/GST-Mint1-PDZ1 pair should not result in significant SPA luminescence signal. Results obtained with bio-NC/GST-Mint1-PDZ1 and bio-NC-W2338A/GST-Mint1-PDZ1 pairs will be used to optimize Z' score (Zhang et al., 1999) of the screen. Following optimization of Z' score, pilot HTS screen with a library of 8,000 test compounds will be performed and Z score (Zhang et al., 1999) will be optimized. Compounds that reduce luminescence signal by more than 50% will be selected for further evaluation.

iii) Homogenous Time-Resolved Fluorescence Resonance Energy Transfer

The homogeneous time-resolved fluorescence resonance energy transfer (HTRF) studies are based on the FRET energy transfer between caged donor fluorophore with a delayed emission and a neighboring acceptor fluorophore. Excitation of a donor fluorophore by a Xenon flash lamp results in prompt fluorescence. Photons emmited during delayed emission stage are absorbed by an acceptor and result in HTRF signal. HTRF signal is collected during integration time that can be adjusted to yield maximal signal to noise ratio. To further improve signal to noise ratio, multiple flashes can be used to stimulate the same sample.

Bio-NC peptide and GST-Mint1-PDZ1 proteins will be mixed in HTRF buffer (0.2% BSA in PBS, 100 mM KF) in the presence of 5 μM concentration of tested small molecule compounds in a black 384 well plates (Costar) in a final volume of 25 μl for 1 hour. For donor labeling, $Eu^{3+}$ cryptate (EuK) conjugated anti-GST monoclonal antibodies (CIS Bio International, 61GSTKLA) will be added. For acceptor labeling, Streptavidin-XL (Streptavidin conjugated to XL665, 610SAXLA from CIS Bio International) will be added to yield a final volume of 50 μl. The plates will be sealed and incubated for 2 h with shaking in the dark.

Following incubation, HTRF measurements will be taken using LJL Analyst. In these studies, brief Xenon lamp flash will be used for EuK excitation. Prompt EuK fluorescence at 620 nM will be measured for each well on the plate, and then delayed HTRF fluorescence of XL665 at 665 nM will be measured. Time-delayed fluorescence of XL665 will be measured with 50 μs delay after the excitation and 400 μs integration time. Due to 50 μs delay, only the long-lived FRET signal is detected, drastically reducing fluorescence background. The HTRF ratio of A/B counts (665 nm/620 nm), determined for each well, will indicate a dedree of bio-NC peptide association with GST-Mint1-PDZ1 protein.

Control studies will be performed with bio-NC-W2338A peptide instead of bio-NC peptide. Results obtained with bio-NC/GST-Mint1-PDZ1 and bio-NC-W2338A/GST-Mint1-PDZ1 pairs will be used to optimize Z' score (Zhang et al., 1999) of the screen. Following optimization of Z' score, pilot HTS screen with a library of 8,000 test compounds will be performed and Z score (Zhang et al., 1999) will be optimized. Compounds that reduce A/B HTRF ratio by more than 50% will be selected for further evaluation.

iv) AlphaScreen Assay

Figure 6:
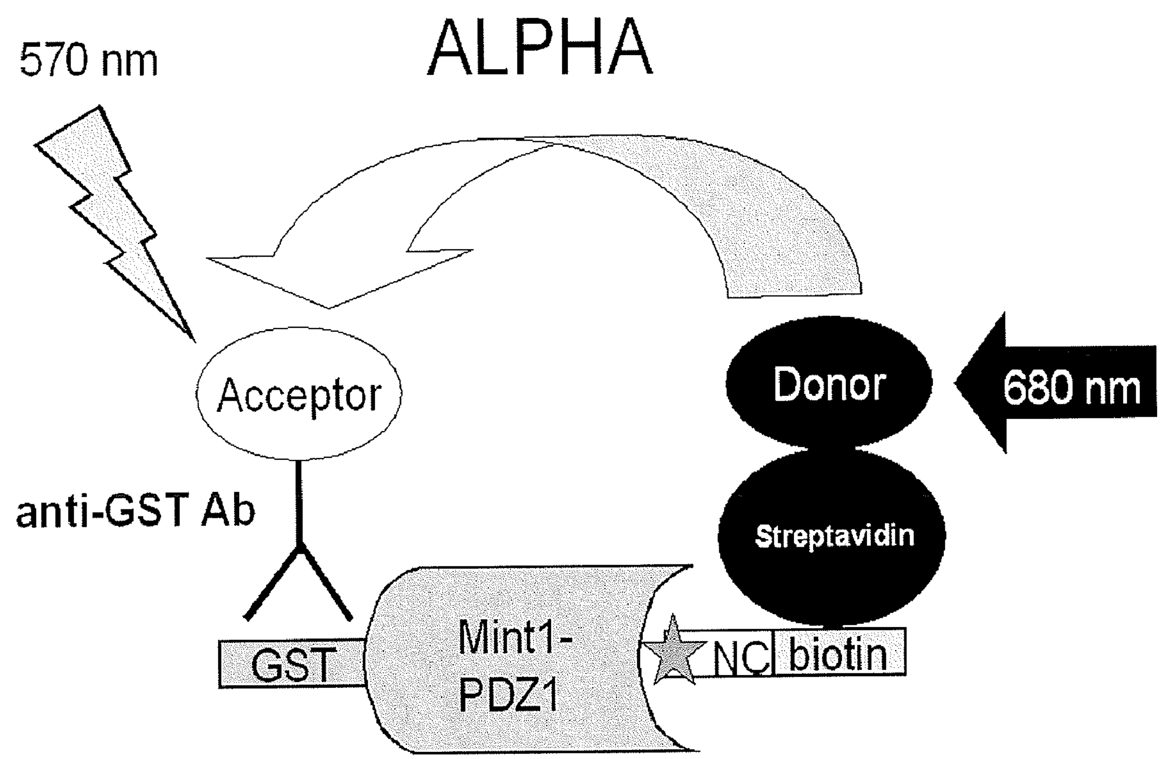
FIG. 6—Principle of ALPHA-based HTS screen for blockers of bio-NC peptide association with GST-Mint1-PDZ1 domain.

The AlphaScreen signal amplification strategy (Perkin Elemers) involves, as a first step, is the conversion of ambient oxygen to the singlet state by a photosensitizer in the Donor bead upon illumination at 680 nm (FIG. 6). The Acceptor beads contain a thioxene derivative that reacts with the singlet oxygen to generate chemiluminescence at 370 nm. Energy transfer to fluorescent acceptors in the same beads shifts the emission wavelength to 520-620 nm. The half-life of the decay reaction is 0.3 sec, which makes the AlphaScreen fluorescence signal very long lived and allows the technology to operate in time-resolved mode. The short lifetime of singlet oxygen in aqueous solution (~4 μsec) allows diffusion over a distance up to ~200 nm (FIG. 6). The ALPHA measurements can be taken using Perkin Elmers Envision In one example, bio-NC peptide (63, 189, 1000 nM) and GST-Mint1-PDZ1/2 protein (63, 189, 1000 nM) were mixed in ALPHA buffer (Hepes 25 mM pH 7.2; NaCl 100 mM; BSA 0.1%) and incubated for 10 h. Anti-GST acceptor beads (Perkin Elmer) and Streptavidin donor beads (Perkin Elmer) were added. The reaction mixture was incubated for 60 more minutes. As a negative control (63, 189, 1000 nM) of Biotin was used in reaction instead of Bio-NC peptide. The reaction mixtures were aliquoted 50 μl per well in black 384 well plates (Costar) for ALPHA measurements. Measurement parameters include excitation at 680 nm, detection −570 nm; excitation time −180 ms; total measurement time −550 ms.

C. In Cyto Assays

Various cell that express Mint1, Mint1-PDZ1, Mint2, or Mint2-PDZ1 can be utilized for screening of candidate substances. Exemplary cells include, but are not limited to yeast cells, bacterial cells, COS cells, HEK293 cells. Depending on the assay, culture may be required. Labeled candidate substances or competitive inhibitors (a peptide of SEQ ID NO:1) is contacted with the cell and binding assessed. Various readouts for binding of candidate substances to cells may be utilized, including fluorescent microscopy and FACS.

D. In Vivo Assays

The present invention particularly contemplates the use of various animal models. For example, various animal models of pain may be used to determine if the binding of candidate substances to Mint1 (Mint1-PDZ1, Mint2, Mint2-PDZ1) affects the ability of the animal to perceive pain in animal models of pain. Testing of acute (physiological) pain: (hot plate, tail flick, paw pressure), inflammatory models: (carrageenan, formalin), and nerve injury: (sciatic nerve ligation, focal spinal injury) and other models including muscle inflammation and cancer evoked bone pain.

Treatment of these animals with test compounds will involve the administration of the compound, in an appropriate form, to the animal. Administration will be by any route the could be utilized for clinical or non-clinical purposes, including but not limited to oral, nasal, buccal, or even topical. Alternatively, administration may be by oral, sublingual, intratracheal instillation, bronchial instillation, intradermal, subcutaneous, intramuscular, intraperitoneal or intravenous injection. Specifically contemplated are oral administration and systemic intravenous injection.

4. Engineering Expression Constructs

In certain embodiments, the present invention involves either the production of CaV2.2 peptides or the administration of a CaV2.2 nucleic acid to an animal. Such methods both rely upon expression constructs containing a CaV2.2 coding region and the means for its expression, plus elements that permit replication of the constructs. A variety of elements and vector types are discussed below.

A. Selectable Markers

In certain embodiments of the invention, expression constructs of the present invention contain nucleic acid constructs whose expression may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin and histidinol are useful selectable markers. Alternatively, enzymes such as herpes simplex virus thymidine kinase (tk) may be employed. Immunologic markers also can be employed. The selectable marker employed is not believed to be important, so long as it is capable of being expressed simultaneously with the nucleic acid encoding a gene product. Further examples of selectable markers are well known to one of skill in the art and include reporters such as EGFP, β-gal or chloramphenicol acetyltransferase (CAT).

B. Polyadenylation Signals

One will typically desire to include a polyadenylation signal to effect proper polyadenylation of the transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read through from the cassette into other sequences.

C. Control Regions

Throughout this application, the term "expression construct" is meant to include any type of genetic construct containing a nucleic acid coding for the peptide of interest. The nucleic acid encoding the peptide is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation.

For the purpose of recombinant production, prokaryotic (bacteria) and lower eukaryotic organisms (yeast) are preferred. Commercial vectors and expression systems, including appropriate host cells and methods for transformation and culture, are well known to those of skill in the art.

In other embodiments, promoters refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

In some circumstances, it may be desirable to regulate expression of a transgene in a gene therapy vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific promoters may be used to effect transcription in specific tissues or cells so as to reduce potential toxicity or undesirable effects to non-targeted tissues. For example, promoters that are selectively active in neuronal tissues, such as dorsal root ganglion (DRG) neurons, nociceptive neurons may find particular utility in accordance with the present invention.

It is envisioned that any of the above promoters alone or in combination with another may be useful according to the present invention depending on the action desired. In addition, this list of promoters should not be construed to be exhaustive or limiting, those of skill in the art will know of other promoters that may be used in conjunction with the promoters and methods disclosed herein.

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters additional to the tissue specific promoters listed above, cellular promoters/enhancers and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

| PROMOTER |
|---|
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| e-fos |
| c-HA-ras |
| Insulin |
| Neural Cell Adhesion Molecule (NCAM) |
| α1-Antitrypsin |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

TABLE 3

| Element | Inducer |
|---|---|
| MT II | Phorbol Ester (TPA)<br>Heavy metals |
| MMTV (mouse mammary tumor virus) | Glucocorticoids |
| β-Interferon | Poly(rI)X<br>Poly(rc) |

TABLE 3-continued

| Element | Inducer |
|---|---|
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose |

5. Methods of Gene Transfer

In order to effect recombinant express of CaV2.2 peptide, it is necessary to transfer the appropriate expression construct into a host cell of interest. Such transfer may employ viral or non-viral methods of gene transfer. This section provides a discussion of methods and compositions of gene transfer.

A. Viral Vector-Mediated Transfer

In one embodiment of the invention, an expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses such as the papovaviruses (simian virus 40, bovine papilloma virus, and polyoma) (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. A wide variety of viruses are now used to successfully transfer genetic material to eukaryotic cells.

In certain embodiments, the nucleic acid sequence is incorporated into a viral particle to mediate gene transfer to a cell. Typically, the virus simply will be exposed to the appropriate host cell under physiologic conditions, permitting uptake of the virus. The present methods may be advantageously employed using a variety of viral vectors, as discussed below.

i) Adenovirus

Adenovirus is particularly suitable for use as a gene transfer vector because of its mid-sized DNA genome, ease of manipulation, high titer, wide target-cell range, and high infectivity. The roughly 36 kB viral genome is bounded by 100-200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present invention, it is possible achieve both these goals while retaining the ability to manipulate the therapeutic constructs with relative ease.

The large displacement of DNA is possible because the cis elements required for viral DNA replication all are localized in the inverted terminal repeats (ITR) (100-200 bp) at either end of the linear viral genome. Plasmids containing ITR's can replicate in the presence of a non-defective adenovirus (Hay et al., 1984). Therefore, inclusion of these elements in an adenoviral vector should permit replication.

In addition, the packaging signal for viral encapsidation is localized between 194-385 bp (0.5-1.1 map units) at the left end of the viral genome (Hearing et al., 1987). This signal mimics the protein recognition site in bacteriophage λ DNA where a specific sequence close to the left end, but outside the cohesive end sequence, mediates the binding to proteins that are required for insertion of the DNA into the head structure. E1 substitution vectors of Ad have demonstrated that a 450 bp (0-1.25 map units) fragment at the left end of the viral genome could direct packaging in 293 cells (Levrero et al., 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element, as provided for in the present invention, derives from the packaging function of adenovirus.

It has been shown that a packaging signal for adenovirus exists in the left end of the conventional adenovirus map (Tibbetts, 1977). Later studies showed that a mutant with a deletion in the E1A (194-358 bp) region of the genome grew poorly even in a cell line that complemented the early (E1A) function (Hearing and Shenk, 1983). When a compensating adenoviral DNA (0-353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved towards the interior of the Ad5 DNA molecule (Hearing et al., 1987).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals are packaged selectively when compared to the helpers. If the preference is great enough, stocks approaching homogeneity should be achieved.

ii) Retrovirus

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and Ψ components is constructed (Mann et al., 1983). When a recombinant plasmid containing a human cDNA, together with the retroviral LTR and Ψ sequences is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., 1975).

An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

iii) Adeno-Associated Virus

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al., 1987), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, 1996; Chatterjee et al., 1995; Ferrari et al., 1996; Fisher et al., 1996; Flotte et al., 1993; Goodman et al., 1994; Kaplitt et al., 1994; 1996, Kessler et al., 1996; Koeberl et al., 1997; Mizukami et al., 1996).

AAV-mediated efficient gene transfer and expression in the lung has led to clinical trials for the treatment of cystic fibrosis (Flotte and Carter, 1995; Flotte et al., 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., 1996; Flotte et al., 1993; Kaplitt et al., 1994; 1996; Koeberl et al., 1997; McCown et al., 1996; Ping et al., 1996; Xiao et al., 1996).

iv) Other Viral Vectors

Other viral vectors may be employed as expression constructs in the present invention. Vectors derived from viruses such as vaccinia virus (Ridgeway, 1988; Baichwal and Sugden, 1986; Coupar et al., 1988) canary pox virus, and herpes viruses may be employed. These viruses offer several features for use in gene transfer into various mammalian cells.

B. Non-Viral Transfer

Several non-viral methods for the transfer of expression constructs into cells are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

Once the construct has been delivered into the cell the nucleic acid encoding the therapeutic gene may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). The addition of DNA to cationic liposomes causes a topological transition from liposomes to optically birefringent liquid-crystalline condensed globules (Radler et al., 1997). These DNA-lipid complexes are potential non-viral vectors for use in gene therapy.

Liposome-mediated nucleic acid delivery and expression of foreign DNA in vitro has been very successful. Using the β-lactamase gene, Wong et al., (1980) demonstrated the feasibility of liposome-mediated delivery and expression of foreign DNA in cultured chick embryo, HeLa, and hepatoma cells. Nicolau et al., (1987) accomplished successful liposome-mediated gene transfer in rats after intravenous injection. Also included are various commercial approaches involving "lipofection" technology.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferring (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a cell type such as prostate, epithelial or tumor cells, by any number of receptor-ligand systems with or without liposomes. For example, the human prostate-specific antigen (Watt et al., 1986) may be used as the receptor for mediated delivery of a nucleic acid in prostate tissue.

In another embodiment of the invention, the expression construct may simply consist of naked recombinant DNA or plasmids. Transfer of the construct may be performed by any of the methods mentioned above which physically or chemically permeabilize the cell membrane. This is applicable particularly for transfer in vitro, however, it may be applied for in vivo use as well. Dubensky et al., (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a CAM also may be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

6. Methods of Treating Pain

The present invention also contemplates method of inhibiting pain using peptides or mimetics of the carboxy-terminus of CaV2.2. Binding of such agents to Mint1 has now been shown to reduce pain in vivo. Thus, it is contemplated that the administration of CaV2.2 or mimetics into subjects will reduce or even prevent pain.

As discussed above, pain can be essentially divided into 2 broad categories: physiological pain and pathological pain. Physiological pain is good for the organism in that it is protective. To prevent damage to tissue, physiological pain pathways are activated by noxious stimulation. Physiological pain must only be controlled under specific clinical situations, such as during surgery, medical procedures, or following trauma. Drugs that chronically disable pathways that transmit physiological pain are undesirable as they cause the organism to lose the protective function of pain. Pathological pain, on the other hand, is not the result of a noxious stimulation or healing tissue. Pathological pain originates from abnormal function of the nervous system due to nerve lesion or compression, neuropathy, tumor growth, or tissue inflammation. Current therapeutics that are used for the treatment of pathological pain are typically limited by serious side effects and the development of tolerance.

A. Physiological Pain

The sensory experience of physiological (acute) pain caused by a noxious stimulus is mediated by a specialized high-threshold sensory system. This system extends from the periphery through the spinal cord, brain stem and thalamus to the cerebral cortex where the sensation is perceived. A withdrawal response is initiated to prevent tissue damage. Physiological pain is a vital sensation and is associated with survival of the organism.

B. Inflammatory Pain

If tissue damage occurs in spite of the protection rendered by the physiological pain system (i.e., via trauma, surgery, or inflammatory disease), the body shifts from protecting against noxious stimulation to promoting the healing of injured tissue. Inflammatory pain helps to achieve this goal by increasing sensitivity to stimuli that are not normally painful (hyperalgesia). By having a heightened perception of pain, the organism limits movement and enables healing. When the inflammation is reduced, pain dissapates. In the case of chronic inflammation (e.g., rheumatoid arthritis), however, pain states inflammatory pain persists. Cancer pain can sometimes fit into this pain category as some tumors will release inflammatory mediators that serve to sensitive nerves in the surrounding tissue.

C. Neuropathic Pain

Neuropathic pain may result from lesions to the peripheral nervous system, as in patients with diabetes, post-herpetic neuralgias, AIDS, or in patients with spinal cord injuries. Cancer pain can fit into the category of neuropathic pain if tumor growth creates nerve impingements.

D. Genetic Based Therapies

Specifically, the present inventors intend to provide, to a cell, an expression construct that expresses a CaV2.2 peptide or variant thereof. The lengthy discussion of expression vectors and the genetic elements employed therein is incorporated into this section by reference. Particularly preferred expression vectors are viral vectors such as adenovirus, adeno-associated virus, herpesvirus, vaccinia virus and retrovirus. Also preferred is liposomally-encapsulated expression vector.

Those of skill in the art are well aware of how to apply gene delivery to in vivo and ex vivo situations. For viral vectors, one generally will prepare a viral vector stock. Depending on the kind of virus and the titer attainable, one will deliver $1\times10^4$, $1\times10^5$, $1\times10^6$, $1\times1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below.

E. Protein Therapy

Another therapy approach is the provision, to a subject, of CaV2.2 peptides, synthetic or recombinant, or variants, mimetics or analogs thereof. Formulations would be selected based on the route of administration and purpose including, but not limited to, parenteral formulations, topical formulations, liposomal formulations and classic pharmaceutical preparations for oral administration.

F. Combined Therapy

In order to increase the effectiveness of CaV2.2 peptides or mimics or analogs thereof, it may be desirable to combine these compositions with another agent effective in the treatment of pain. The terms "contacted" and "exposed," when applied to a cell, tissue or organism, are used herein to describe the process by which a CaV2.2 peptide or mimic or analog and/or another anti-pain agent are delivered to a target cell, tissue or organism or are placed in direct juxtaposition with the target cell, tissue or organism. Anti-pain agents include, but are not limited to, steroids, NSAIDS (COX-2 inhibitors, salicylates, indoleacetic acid derivatives, fenamates, benzothiazine derivatives, pyrrolacetic acids), and analgesics & opiods (lidocaine, morphine, fentanyl, midazolam, propofol, lorazepam, haloperidol, thiopental, pentobarbital, diazepam).

The CaV2.2 peptide or mimic or analog may precede, be co-current with and/or follow the other agent(s) by intervals ranging from minutes to weeks. In embodiments where the CaV2.2 peptide or mimic or analog, and other agent(s) are applied separately to a cell, tissue or organism, one would generally ensure that a significant period of time did not expire between the time of each delivery, such that the peptide and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the CaV2.2 peptide or mimic or analog. In other aspects, one or more agents may be administered within of from substantially simultaneously, about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 18 hours, about 24 hours, about 36 hours, about 48 hours, about 3 days, about 4 days, about 5 days, about 6 days, about 7 days, about 8 days, about 9 days, about 10 days, about 11 days, about 12 days, about 13 days, about 14 days, about 21 days, about 4 weeks, about 5 weeks, about 6 weeks, about 7 week or about 8 weeks or more, and any range derivable therein, prior to and/or after administering the CaV2.2 peptide or mimic or analog.

Various combination regimens of the CaV2.2 treatment and one or more other anti-pain agents may be employed. Non-limiting examples of such combinations are shown below, wherein a CaV2.2 composition is "A" and the other anti-pain agent is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the CaV2.2 composition to a cell, tissue or organism may follow general protocols for the administration of pharmaceuticals, taking into account the toxicity, if any. It is expected that the treatment cycles would be repeated as necessary. In particular embodiments, it is contemplated that various additional agents may be applied in any combination with the present invention.

G. Pharmaceutical Formulations

Pharmaceutical formulations of the present invention comprise an effective amount of a CaV2.2 agent dissolved or dispersed in a pharmaceutically acceptable carrier. The phrases "pharmaceutical or pharmacologically acceptable" refer to compositions that do not produce an adverse, allergic or other untoward reaction when administered to an animal, such as, for example, a human, as appropriate. The preparation of such pharmaceutical compositions are known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. Except insofar as any conventional carrier is incompatible with the active ingredient, its use in the therapeutic or pharmaceutical compositions is contemplated.

The pharmaceuticals of the present invention may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intramuscularly, intraperitoneally, subcutaneously, subconjunctival, intravesicularlly, mucosally, intrapericardially, intraumbilically, intraocularally, orally, topically, locally, inhalation (e.g., aerosol), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The pharmaceuticals may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g. glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In certain embodiments, the compositions are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

7. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

First, animals are injected with a 10 μM (20 μl) solution of the test compound (dissolved in PBS) in the dorsal surface of the hindpaw. One hour following the injection of the test compound, animals receive a formalin injection (20 μl of a 5% solution) into the dorsal surface of the hindpaw. The contralateral paw is not injected. Following injection, animals are immediately transferred to a plexiglass observation cage. Each animal is observed for a total of 60 minutes following formalin injection. The period spent biting, scratching, or licking the injected hindpaw is recorded (pain score). Data is presented as cumulative time spent biting, scratching, and licking in phase I (0-10 min) and phase II (11-60 min).

Example 2

Results

One hour following delivery of either saline (control) or R9-NC into the dorsum of the hindpaw, formalin (20 μl of a 5% solution) was injected into the same hindpaw. No effect of R9-NC on phase I of the formalin assay was observed. (FIG. 1B) In contrast, a significant reduction of phase II of the formalin assay in the R9-NC treated group was observed when compared to the control group. (FIG. 1B) These data indicate that R9-NC does not alter physiological pain (phase I), but it does block pain that is produced by central sensitization (phase II). Additionally, no untoward side effect of the R9-NC was observed when injected in the hindpaw.

Figure 2:
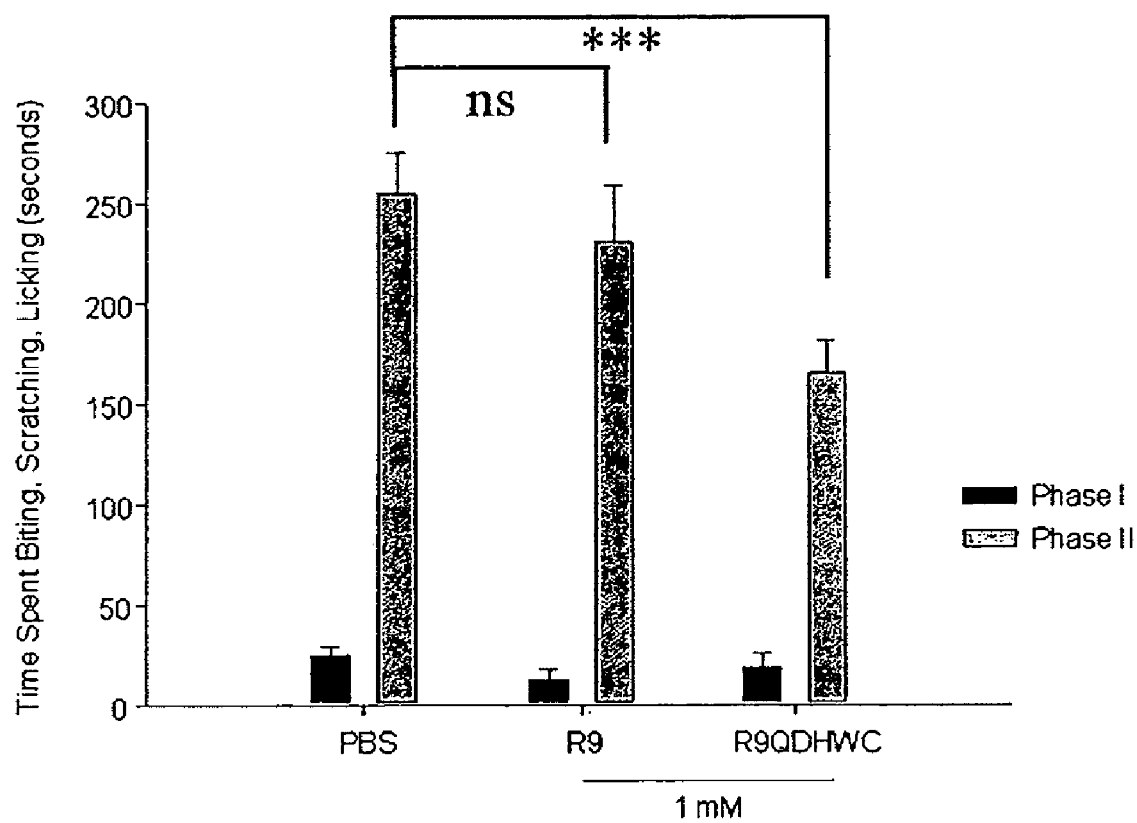
FIG. 2—Supression of phase II, but not phase I formalin response in rats injected with R9-QDHWC peptide. The effect of i.v. administration of PBS, R9 (1 mM) or R9-QDHWC (1 mM) on phase I and phase II of the formalin assay. Phase I represents the period from 0-10 min following formalin injection and phase II represents the period from 11-60 min following formalin injection. N=4-7 rats per group. *** indicates a significant difference when compared to PBS injection (p<0.01).

As is shown in FIG. 2, the peptide R9-QDHWC (full sequence RRRRRRRRRQDHWC; SEQ ID NO_also inhibits phage II but not phase I responses in the rat formalin model. Male Sprague Dawley rats (175-225 gm) received a tail vein injection of either PBS, R9 (1 mM), or R9-QDHWC (1 mM) following which they were placed in a plexiglass observation chamber to allow for acclimation. Thirty minutes following the tail vein injection, the dorsal surface of one hind paw was injected with 50 ul of a 5% formalin solution. Observers, blind to drug treatment, scored the number of biting, licking, and scratching behaviors of the injected hindlimb and paw. Data were analyzed with SigmaStat Software (SPSS, Inc. v. 2.03) using ANOVA followed by a Tukey post hoc analysis.

No significant differences between any group were observed during phase I of the formalin assay [$F(_{2,16})=0.691$ $p>0.5$]. In contrast, there was a significant reduction in formalin induced phase II behaviors in the R9-QDHWC treated animals when compared to the PBS treated rats [$F(_{2,17})=4.815$ $p=0.007$]. PBS vs R9 for phase II was not significantly different (n·s) and p=0.744. Further, delivery of the peptide to rats had no apparent adverse effects.

Figure 3:
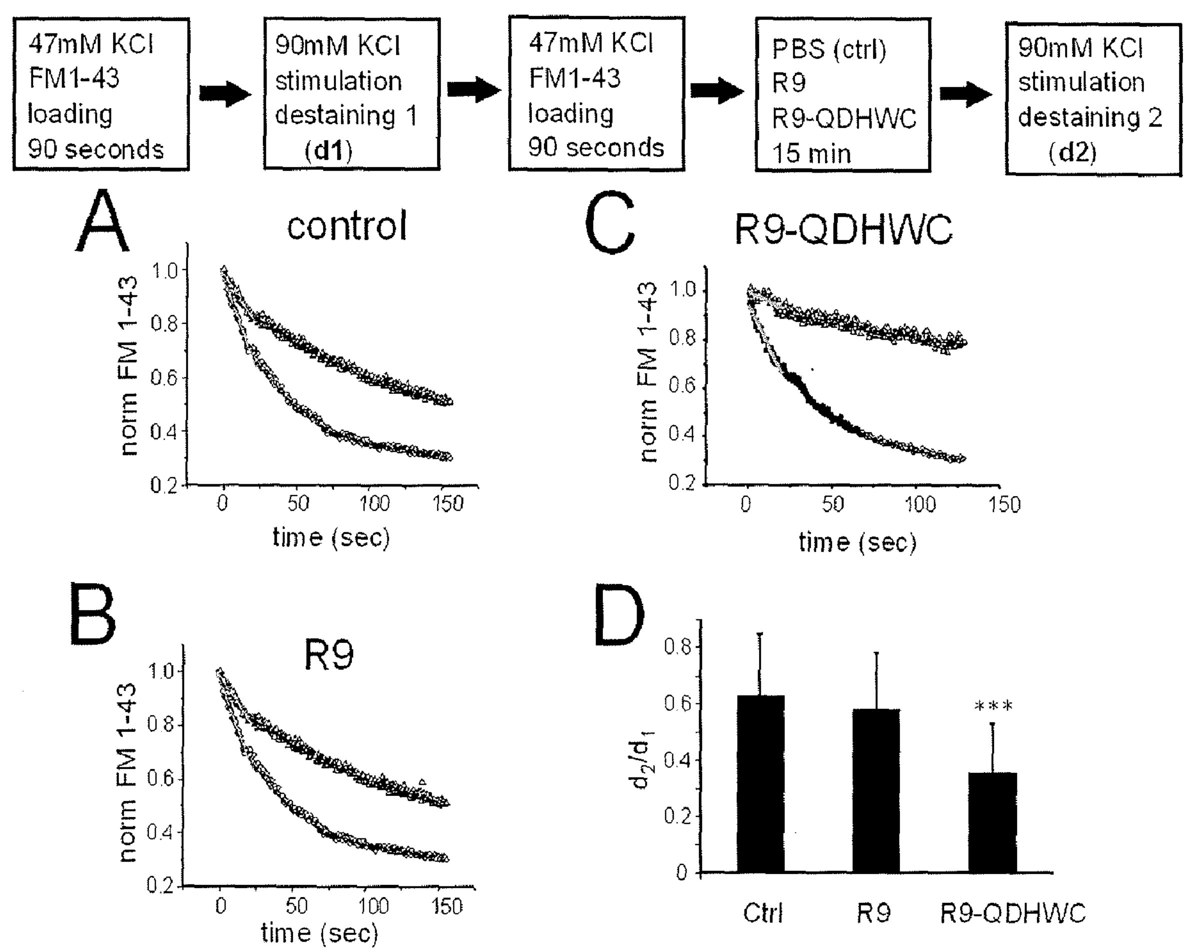
FIGS. 3A-D—Effects of R9-QDHWC peptides on synaptic function. Double-staining protocol is shown on the top. Results of first and second destaining are shown for representative puncta for control neurons (FIG. 3A), for neurons loaded with R9 peptide (FIG. 3B) and for neurons loaded with R9-QDHWC peptide (FIG. 3C). An average d2/d1 ratios are compared for all 3 groups of neurons (FIG. 3D).

An FM1-43 imaging was used to study synaptic effects of R9-QDHWC competitive peptide that corresponds to Mint-PDZ binding site on $Ca_v2.2$ subunit. In these experiments we adapted double-staining protocol from (Reuter, 1995). First the mature hippocampal neuronal cultures were stained with FM1-43 dye for 90 sec in the presence of 47 mM KCl (FIG. 3, top). Following staining and washout of the dye (10 min) the neurons were stimulated by 90 mM KCl and the initial rate of destaining (d1) was measured at each puncta (FIG. 3, top). After completion of the first destaining protocol, the same neuronal culture was re-stained with FM1-43 for 90 sec in the presence of 47 mM KCl. Following re-staining and washout of the dye (10 min), neurons were incubated with 50 μM of R9-QDHWC or R9 peptides for 15 min. The control group of neurons was incubated for 15 min with addition of PBS. Following loading with R9 peptides, neurons were washed for 10 min and subjected to 90 mM KCl stimulation. The initial rate of destaining (d2) was once again measured at each puncta (FIG. 3, top).

To compare the results obtained during first and second destaining protocols and to minimize puncta-to-puncta variability, the inventors calculated the d2/d1 ratios for each puncta. They found that, for control and R9-loaded neurons, the average d2/d1 ratio was equal to 0.6±0.2 (n=30) and 0.55±0.15 (n=28), respectively (FIGS. 3A, 3B, 3D), but for R9-QDHWC loaded neurons the ratio was reduced to 0.32±0.18 (n=35) (FIGS. 3C, 3D). Thus, loading of hippocampal neurons with R9-QDHWC peptide resulted in specific impairment of synaptic function in our experiments.

Figure 4:
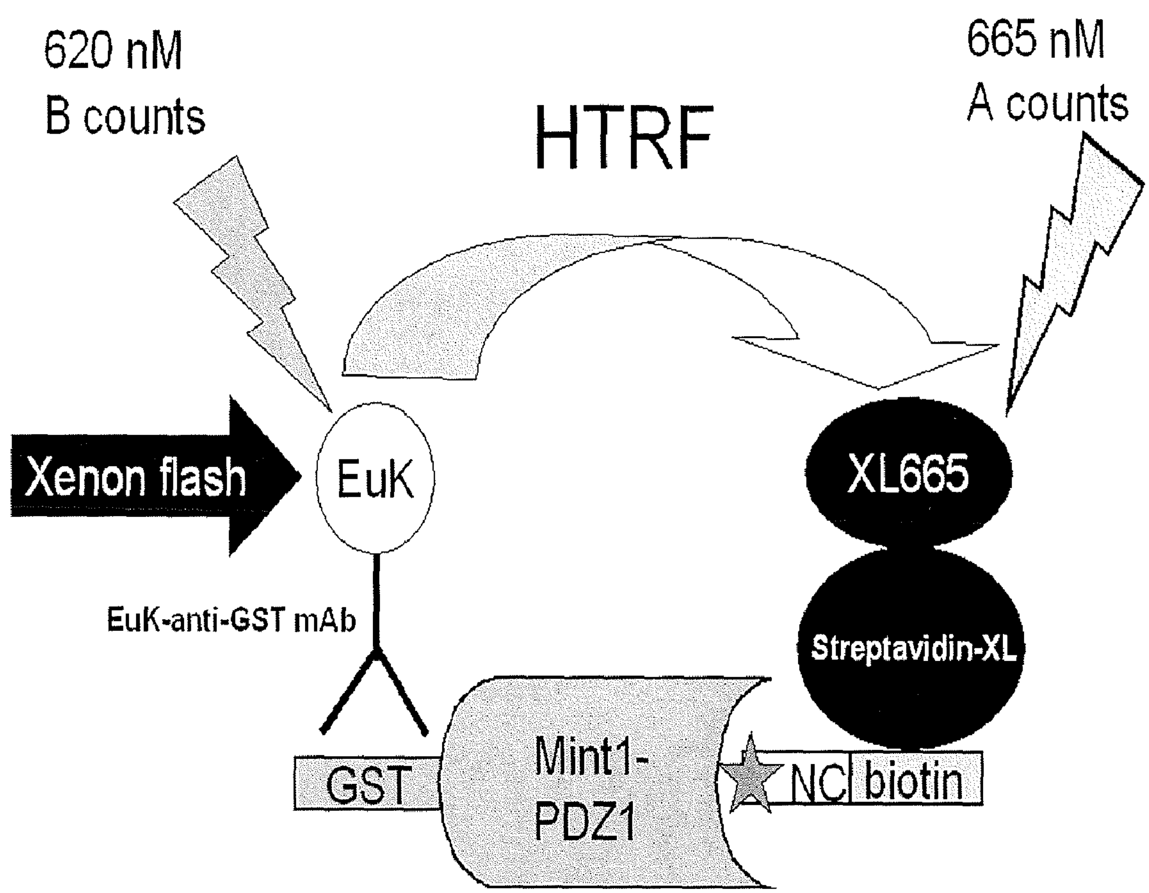
FIG. 4—Principle of HTRF-based HTS screen for blockers of bio-NC peptide association with GST-Mint1-PDZ1 domain.

The homogenious time-resolved fluorescence resonance energy transfer (HTRF) experiments are based on the FRET energy transfer between caged donor fluorophore with a delayed emission and a neighboring acceptor fluorophore (FIG. 4). Excitation of a donor fluorophore by a Xenon flash lamp results in prompt fluorescence (FIG. 4). Photons emmited during delayed emission stage are absorbed by an acceptor and result in HTRF signal. Bio-NC peptide (1000 nM) and GST-Mint1-PDZ1/2 protein (1000 nM) were mixed in HTRF buffer (0.2% BSA in PBS, 100 mM KF) and incubated for 90 min. For donor labeling, $Eu^{3+}$ cryptate (EuK) conjugated anti-GST monoclonal antibodies (CIS Bio International, 61GSTKLA) were added (10 nM). For acceptor labeling, Streptavidin-XL (Streptavidin conjugated to XL665, 610SAXLA from CIS Bio International) were added (100 nM). The reaction mixture was incubated for 60 more minutes. As a negative control 1000 nM of Biotin was used in reaction instead of Bio-NC peptide. The reaction mixtures were aliquoted 50 μl per well in black 384 well plates (Costar) for HTRF measurements.

The HTRF measurements were taken using Perkin Elmers Envision available at UT Southwestern HTS facility. Parameters: Excitation at 320 nm. Detection—Channel 1: 665 nm; Channel 2: 590 nm. Delay 50 μs. Time between flashes: 2000 μs. Number of flashes: 200/well. The HTRF ratio of 665 nm/620 nm (channel1/channel2).

Figure 5:
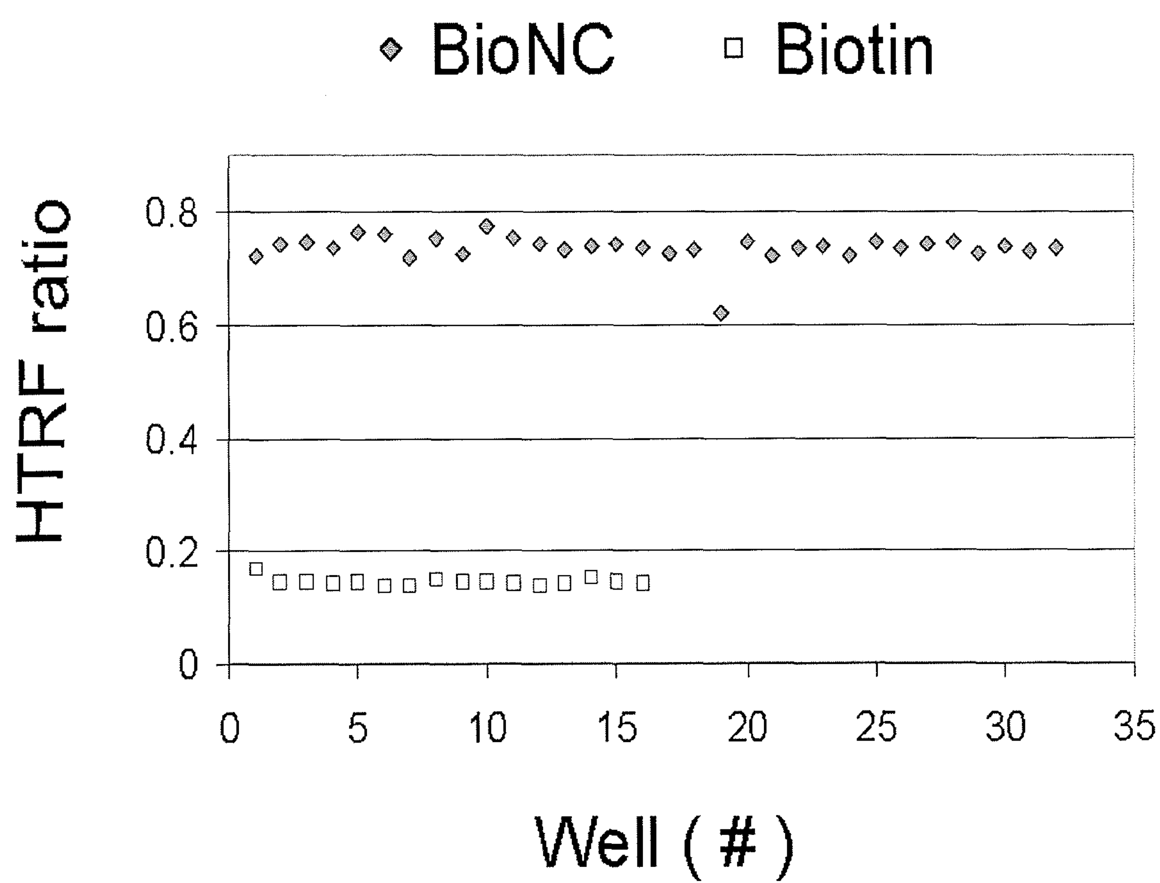
FIG. 5—HTRF data using bio-NC and GST-Mint1-PDZ1. Biotin is a control.

The inventors determined that HTRF ratio is equal to 0.06 for bio-NC/GST-Mint1-PDZ-1/2 pair (FIG. 5). In control experiments, they determined that HTRF ratio is less than 0.04 for Biotin/GST-Mint1-PDZ-1/2 pair (FIG. 5). Thus, the signal/background ratio in present conditions was 1.7 (FIG. 5). The data are highly reproducible (FIG. 5), but further optimization is required to improve S/B ratio for HTS screen.

The initial step in the AlphaScreen signal amplification strategy (Perkin Elemers) is the conversion of ambient oxygen to the singlet state by a photosensitizer in the Donor bead upon illumination at 680 nm (FIG. 6). The Acceptor beads contain a thioxene derivative that reacts with the singlet oxygen to generate chemiluminescence at 370 nm. Energy transfer to fluorescent acceptors in the same beads shifts the emission wavelength to 520-620 nm. The half-life of the decay reaction is 0.3 sec, which makes the AlphaScreen fluorescence signal very long lived and allows the technology to operate in time-resolved mode. The short lifetime of singlet oxygen in aqueous solution (~4 μsec) allows diffusion over a distance up to ~200 nm (FIG. 6).

In the inventors' experiments, bio-NC peptide (63, 189, 1000 nM) and GST-Mint1-PDZ1/2 protein (63, 189, 1000 nM) were mixed in ALPHA buffer (Hepes 25 mM, pH 7.2; NaCl 100 mM; BSA 0.1%) and incubated for 10 h. Anti-GST acceptor beads (Perkin-Elmer) and Streptavidin donor beads (Perkin-Elmer) were added. The reaction mixture was incubated for 60 more minutes. As a negative control (63, 189, 1000 nM) of Biotin was used in reaction instead of Bio-NC peptide. The reaction mixtures were aliquoted 50 μl per well in black 384 well plates (Costar) for ALPHA measurements.

The ALPHA measurements were taken using Perkin Elmers Envision available at UT Southwestern HTS facility. Parameters: Excitation at 680 nm. Detection −570 nm. Excitation time: 180 ms. Total measurement time: 550 ms.

Figure 7:
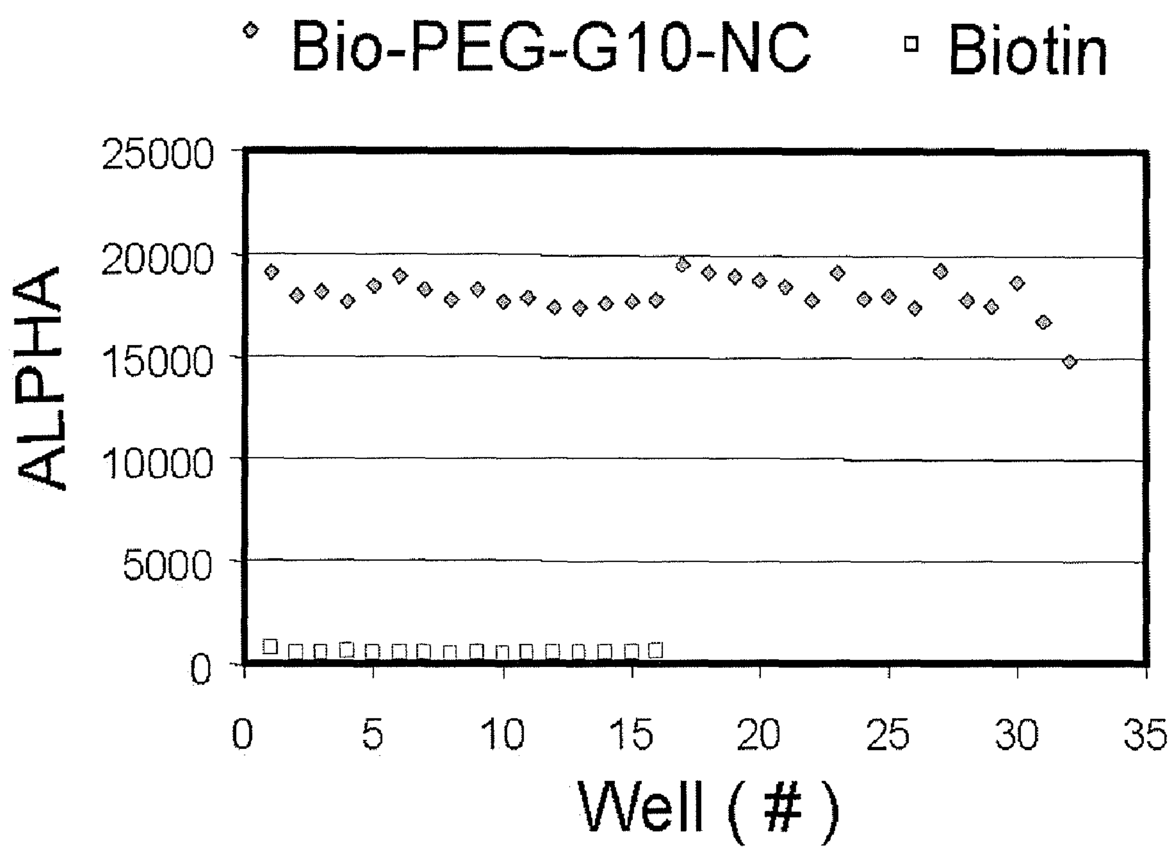
FIG. 7—ALPHA data using bio-NC and GST-Mint1-PDZ1. Biotin is a control.

The inventors determined that ALPHA signal is equal to 22,000 for bio-NC/GST-Mint1-PDZ-1/2 pair (FIG. 7, 189 nM concentration). In control experiments, they determined that ALPHA signal is less than 1,500 for Biotin/GST-Mint1-PDZ-1/2 pair (FIG. 7). Thus, the signal/background ratio in this conditions is 14 (FIG. 7). The data are highly reproducible (FIG. 7).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 5,429,921
U.S. Pat. No. 5,440,013
U.S. Pat. No. 5,446,128
U.S. Pat. No. 5,475,085
U.S. Pat. No. 5,618,914
U.S. Pat. No. 5,670,155
U.S. Pat. No. 5,672,681
U.S. Pat. No. 5,674,976
U.S. Pat. No. 5,710,245
U.S. Pat. No. 5,792,846
U.S. Pat. No. 5,840,833
U.S. Pat. No. 5,846,757
U.S. Pat. No. 5,851,824
U.S. Pat. No. 5,859,184
U.S. Pat. No. 5,929,237
U.S. Pat. No. 6,096,514
U.S. Pat. No. 6,140,485
U.S. Pat. No. 6,229,000
U.S. Pat. No. 6,353,091
U.S. Pat. No. 6,528,630
U.S. Pat. No. 6,653,097
Bahls et al., *J. Neurobiol.,* 35:198-208, 1998.
Baichwal and Sugden, *In: Gene Transfer*, Kucherlapati (Ed.), NY, Plenum Press, 117-148, 1986.
Bakke et al., *Cell,* 63(4):707-716, 1990.
Barany and Merrifield, In: *The Peptides*, Gross and Meienhofer (Eds.), Academic Press, NY, 1-284, 1979.
Becker-Hapak et al., *Methods,* 24:247-256, 2001.
Benvenisty and Neshif, *Proc. Natl. Acad. Sci. USA,* 83(24): 9551-9555, 1986.
Bezprozvanny and Maximov, *FEB Lett.* 509:457-462, 2001.
Butz et al., *Cell,* 94:773-782, 1998.
Capaldi et al., *Biochem. Biophys. Res. Comm.,* 74(2):425-433, 1977.
Carter and Flotte, *Curr. Top Microbiol. Immunol.,* 218:119-144, 1996.
Chattejee, et al., *Ann. N.Y. Acad. Sci.,* 770:79-90, 1995.
Chen and Okayama, *Mol. Cell Biol.,* 7(8):2745-2752, 1987.
Coffin, In: *Virology*, Fields et al. (Eds.), Raven Press, NY, 1437-1500, 1990.
Coupar et al., *Gene,* 68:1-10, 1988.
Craven and Bredt, *Cell,* 93:495-498, 1998.
Denicourt and Dowdy, *Trends Pharmacol. Sci.,* 24:216-218, 2003.
Dubensky et al., *Proc. Natl. Acad. Sci. USA,* 81:7529-7533, 1984.
Dunlap et al., *Trends Neurosci.,* 18:89-98, 1995.

EPO 0273085
Ertel et al., *Neuron.*, 25:533-535, 2000.
Fanning and Anderson, *Curr. Biol.*, 6:1385-1388, 1996.
Fechheimer, et al., *Proc Natl. Acad. Sci. USA*, 84:8463-8467, 1987.
Ferkol et al., *FASEB J.*, 7:1081-1091, 1993.
Ferrari et al., *J. Virol.*, 70(5):3227-3234, 1996.
Fisher et al., *Hum. Gene Ther.*, 7(17):2079-2087, 1996.
Fletcher et al., *Cell*, 87:607-617, 1996.
Flotte and Carter, *Gene Ther.* 2(6):357-362, 1995.
Flotte et al., *Proc. Natl. Acad. Sci. USA*, 90(22):10613-10617, 1993.
Fraley et al., *Proc. Natl. Acad. Sci. USA*, 76:3348-3352, 1979.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gohil et al., *Brain Res.*, 653:258-266, 1994.
Goodman et al., *Blood*, 84(5):1492-1500, 1994.
Gopal, *Mol. Cell Biol.*, 5:1188-1190, 1985.
Graham and Van Der Eb, *Virology*, 52:456-467, 1973.
Harland and Weintraub, *J. Cell Biol.*, 101(3):1094-1099, 1985.
Harlow et al., *Mol. Cell Biol.*, 5(7):1601-1610, 1985.
Hatakeyama et al., *Neuroreport.*, 12:2423-2427, 2001.
Hay et al., *J. Molec. Biology*, 175:493-510, 1984.
Hearing and Shenk, *J. Molec. Biology*, 167:809-822, 1983.
Hearing et al., *J. Virology*, 67:2555-2558, 1987.
Hibino et al., *Neuron.*, 34:411-423, 2002.
Ho et al., *Proc. Natl. Acad. Sci. USA*, 100:1409-1414, 2003.
Irie et al., *Science*, 277:1511-1515, 1997.
Johannesson et al. *J. Med. Chem.*, 1999 Nov. 4; 42(22):4524-37, 1999.
Johnson et al., *In: Biotechnology And Pharmacy*, Pezzuto et al. (Eds.), Chapman and Hall, NY, 1993.
Kaneda et al., *Science*, 243:375-378, 1989.
Kaneko et al., *J. Neurosci.*, 22:82-92, 2002.
Kaplitt et al., *Methods*, 10(3):343-350, 1996.
Kaplitt et al., *Nat Genet.*, 8(2):148-54, 1994.
Kato et al, *J. Biol. Chem.*, 266:3361-3364, 1991.
Kerr et al., *Eur. J. Pharmacol.*, 146:181-183, 1988.
Kessler et al., *Proc. Natl. Acad. Sci. USA*, 93(24):14082-14087, 1996.
Kim et al., *Mol. Cell Neurosci.*, 18:235-245, 2001.
Klein et al., *Nature*, 327:70-73, 1987.
Koeberl et al., *Proc. Natl. Acad. Sci. USA*, 94(4):1426-1431, 1997.
Kornau et al., *Curr. Opin. Neurobiol.*, 7:368-373, 1997.
Kubota et al., *Biochem. Biophys. Res. Commun.*, 162(3):963-970, 1989.
Kyte and Doolittle, *J. Mol. Biol.*, 157(1):105-132, 1982.
Lanford et al., *Cell*, 46(4):575-582, 1986.
Letourneur et al., Cell, 69(7):1143-1157, 1992.
Levrero et al., *Gene*, 101:195-202, 1991.
Llinas et al., *Biophys. J.*, 33:323-351, 1981.
Lu and Dunlap, *J. Biol. Chem.*, 274:34566-34575, 1999.
Malmberg and Yaksh, *J. Neurosci.*, 14:4882-4890, 1994.
Malmberg and Yaksh, *Pain*, 60:83-90, 1995.
Mann et al., *Cell*, 33:153-159, 1983.
Maximov and Bezprozvanny, *J. Neurosci.*, 22:6939-6952, 2002.
Maximov et al., *J. Biol. Chem.*, 274:24453-24456, 1999.
McCleskey and Gold, *Annu. Rev. Physiol.*, 61:835-856, 1999.
McCown et al., *Brain Res*, 713(1-2):99-107, 1996.
Merrifield, *Science*, 232(4748):341-347, 1986.
Missler et al., *Nature*, 424:939-948, 2003.
Mizukami et al., *Virology*, 217(1):124-130, 1996.
Mori et al., *Nature*, 350:398-402, 1991.
Munro et al., *Cell*, 48(5):899-907, 1987.
Nguyen and Sudhof, *J. Biol. Chem.*, 272:26032-26039, 1997.
Nicolas and Rubenstein, In: *Vectors: A survey of molecular cloning vectors and their uses*, Rodriguez and Denhardt (Eds.), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Paskind et al., *Virology*, 67:242-248, 1975.
PCT Appln. WO 84/03564
Penn and Paice, *Pain*, 85:291-296, 2000.
Perales et al., *Proc. Natl. Acad. Sci. USA*, 91:4086-4090, 1994.
Ping et al., *Microcirculation*, 3(2):225-228, 1996.
Potter et al., *Proc. Natl. Acad. Sci. USA*, 81:7161-7165, 1984.
Radler et al., *Science*, 275:810-814, 1997.
Remington's Pharmaceutical Sciences, 18th Ed. Mack Printing Company, 1990.
Renan, *Radiother. Oncol.*, 19:197-218, 1990.
Reuter, *Neuron.*, 14:773-779, 1995.
Ridgeway, *In: Vectors: A survey of molecular cloning vectors and their uses*, Rodriguez and Denhardt (Eds.), Stoneham: Butterworth, 467-492, 1988.
Rippe et al., *Mol. Cell Biol.*, 10:689-695, 1990.
Roux et al., *Proc. Natl. Acad. Sci. USA*, 86:9079-9083, 1989.
Saegusa et al., *Embo J.*, 20:2349-2356, 2001.
Samulski et al., *J. Virol.*, 61(10):3096-3101, 1987.
Schwarze et al., *Trends Cell Biol.*, 10:290-295, 2000.
Siomi et al., *Cell*, 55(2):197-209, 1988.
Song et al., *Proc. Natl. Acad. Sci. USA*, 96:1100-1105, 1999.
Stanton et al., *Proc. Natl. Acad. Sci. USA*, 83(6):1772-1776, 1986.
Stewart and Young, In: *Solid Phase Peptide Synthesis*, 2d. ed., Pierce Chemical Co., 1984.
Takahashi and Momiyama, *Nature*, 366:156-158, 1993.
Tam et al., *J. Am. Chem. Soc.*, 105:6442, 1983.
Temin, *In: Gene Transfer*, Kucherlapati (Ed.), NY, Plenum Press, 149-188, 1986.
Tibbetts *Cell*, 12:243-249, 1977.
Timmermann et al., *J. Neurosci. Res.*, 67:48-61, 2002.
Tsien et al., *Trends Pharm. Sci.*, 12:349-354, 1991.
Tur-Kaspa et al., *Mol. Cell Biol.*, 6:716-718, 1986.
Vita et al., *Biopolymers*, 47:93-100, 1998.
Wagner et al., *Proc. Natl. Acad. Sci. USA* 87(9):3410-3414, 1990.
Walker et al., *J. Biol. Chem.*, 273:2361-2367, 1998.
Watt et al., *Proc. Natl. Acad. Sci.*, 83(2):3166-3170, 1986.
Weisshoff et al., *Eur. J. Biochem.*, 259(3):776-788, 1999.
Wender et al., *Proc. Natl. Acad. Sci. USA*, 97:13003-13008, 2000.
Westenbroek et al., *J. Neurosci.*, 18:6319-6330, 1998.
Wheeler et al., *Science*, 264:107-111, 1994.
Whitfield et al., *Anal. Biochem.*, 322:170-178, 2003.
Williams et al., *Science*, 257:389-395, 1992.
Wittemann et al., *J. Biol. Chem.*, 275:37807-37814, 2000.
Wong et al., *Gene*, 10:87-94, 1980.
Wu and Wu, *Adv. Drug Delivery Rev.*, 12:159-167, 1993.
Wu and Wu, *Biochemistry*, 27:887-892, 1988.
Wu and Wu, *J. Biol. Chem.*, 262:4429-4432, 1987.
Xiao, et al., *J. Virol.*, 70:8098-8108, 1996.
Yaksh, *Trends Pharmacol. Sci.*, 20:329-337, 1999.
Yang et al., *Proc. Natl. Acad. Sci. USA*, 87:9568-9572, 1990.
Yellon et al., *Cardiovasc Res.*, 26(10):983-987, 1992.
Zhang et al., *J. Biomol. Screen*, 4:67-73, 1999.
Zhuchenko et al., *Nat. Genet.*, 15:62-69, 1997.

What is claimed is:

1. A nucleic acid encoding peptide of 4 to 12 residues comprising the sequence DHWC (SEQ ID NO:1) or conservative variants thereof operably linked to a promoter.

2. The nucleic acid of claim 1, wherein said promoter is tissue specific or constitutive.

3. The nucleic acid of claim 1, wherein said promoter is selected from the group consisting of CMV IE, RSV, and SV40 large T.

4. The nucleic acid of claim 1, wherein said nucleic acid further comprises a polyadenylation signal.

5. The nucleic acid of claim 1, wherein said nucleic acid is located in a viral vector.

6. The nucleic acid of claim 5, wherein said viral vector is selected from the group consisting of retrovirus, adenovirus, adeno-associated virus, vaccinia virus, herpesvirus and polyoma virus.

7. The nucleic acid of claim 1, wherein said nucleic acid is comprised in a non-viral vector.

8. The nucleic acid of claim 7, wherein said non-viral vector is comprised in a lipid vehicle.

9. The nucleic acid of claim 8, wherein said lipid vehicle is a liposome.

10. The nucleic acid of claim 1, wherein said nucleic acid further encodes a permeant protein delivery motif fused to SEQ ID NO:1.

11. A method of treating pain in an animal comprising administering to said animal a nucleic acid encoding peptide of 4 to 12 residues comprising the sequence DHWC (SEQ ID NO:1) or conservative variants thereof operably linked to a promoter, said nucleic acid dispersed in a pharmaceutically acceptable buffer, diluent or excipient.

12. The method of claim 11, wherein said nucleic acid is located in a viral vector.

13. The method of claim 12, wherein said viral vector is selected from the group consisting of retrovirus, adenovirus, adeno-associated virus, vaccinia virus, herpesvirus and polyoma virus.

14. The method of claim 11, wherein said nucleic acid is comprised in a non-viral vector.

15. The method of claim 11, wherein the pain to be treated is selected from the group consisting of neuropathic pain, inflammatory pain and pain secondary to cancer.

16. The method of claim 11, further comprising administering a second anti-pain agent to said animal.

17. The nucleic acid of claim 1, wherein said nucleic acid encodes a peptide comprising the sequence of QDHWC (SEQ ID NO:2), DQDHWC (SEQ ID NO:3), PDQDHWC (SEQ ID NO:4), HPDQDHWC (SEQ ID NO:5), HHPDQDHWC (SEQ ID NO:6), YHHPDQDHWC (SEQ ID NO:7), SYHHPDQDHWC (SEQ ID NO:8) or HSYHHPDQDHWC (SEQ ID NO:9).

* * * * *

UNITED STATES PATENT AND TRADEMARK OFFICE

CERTIFICATE OF CORRECTION

PATENT NO. : 7,829,688 B2
APPLICATION NO. : 12/190459
DATED : November 9, 2010
INVENTOR(S) : Mary Garry et al.

It is certified that error appears in the above-identified patent and that said Letters Patent is hereby corrected as shown below:

In column 1, line 10, delete "Grant No. P50-CA70907" and insert --Grant No. NS039552-- therefor.

In column 1, lines 12-13, delete "The government owns rights in the present invention pursuant to grant number NS039552 from the NINDS.".

Signed and Sealed this
Twenty-second Day of February, 2011

David J. Kappos
*Director of the United States Patent and Trademark Office*

SEQUENCE LISTING

<160> NUMBER OF SEQ ID NOS: 13

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 1

Asp His Trp Cys
1

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 2

Gln Asp His Trp Cys
1 5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 3

Asp Gln Asp His Trp Cys
1 5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 4

Pro Asp Gln Asp His Trp Cys
1 5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 5

His Pro Asp Gln Asp His Trp Cys
1 5

<210> SEQ ID NO 6
<211> LENGTH: 9
<212> TYPE: PRT
<213> ORGANISM: Artificial Sequence

```
<220> FEATURE:
<223> OTHER INFORMATION: Description of Artificial Sequence:  Synthetic
      Peptide

<400> SEQUENCE: 6

His His Pro Asp Gln Asp His Trp Cys
 1               5


<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 7

Tyr His His Pro Asp Gln Asp His Trp Cys
 1               5                   10


<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 8

Ser Tyr His His Pro Asp Gln Asp His Trp Cys
 1               5                   10


<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 9

His Ser Tyr His His Pro Asp Gln Asp His Trp Cys
 1               5                   10


<210> SEQ ID NO 10
<211> LENGTH: 7364
<212> TYPE: DNA
<213> ORGANISM: Homo sapiens
<220> FEATURE:
<221> NAME/KEY: CDS
<222> LOCATION: (146)..(7165)

<400> SEQUENCE: 10

gcggcggcgg ctgcggcggt ggggccgggc gaggtccgct gcggtcccgg cggctccgtg     60

gctgctccgc tctgagcgcc tggcgcgccc cgcgccctcc ctgccggggc cgctgggccg    120

gggatgcacg cggggcccgg gagcc atg gtc cgc ttc ggg gac gag ctg ggc      172
                            Met Val Arg Phe Gly Asp Glu Leu Gly
                              1               5

ggc cgc tat gga ggc ccc ggc ggc gga gag cgg gcc cgg ggc ggc ggg      220
Gly Arg Tyr Gly Gly Pro Gly Gly Gly Glu Arg Ala Arg Gly Gly Gly
 10                  15                  20                  25

gcc ggc ggg gcg ggg ggc ccg ggt ccc ggg ggg ctg cag ccc ggc cag      268
Ala Gly Gly Ala Gly Gly Pro Gly Pro Gly Gly Leu Gln Pro Gly Gln
                 30                  35                  40

cgg gtc ctc tac aag caa tcg atc gcg cag cgc gcg cgg acc atg gcg      316
```

-continued

```
Arg Val Leu Tyr Lys Gln Ser Ile Ala Gln Arg Ala Arg Thr Met Ala
            45                  50                  55

ctg tac aac ccc atc ccg gtc aag cag aac tgc ttc acc gtc aac cgc      364
Leu Tyr Asn Pro Ile Pro Val Lys Gln Asn Cys Phe Thr Val Asn Arg
        60                  65                  70

tcg ctc ttc gtc ttc agc gag gac aac gtc gtc cgc aaa tac gcg aag      412
Ser Leu Phe Val Phe Ser Glu Asp Asn Val Val Arg Lys Tyr Ala Lys
    75                  80                  85

cgc atc acc gag tgg cct cca ttc gag tat atg atc ctg gcc acc atc      460
Arg Ile Thr Glu Trp Pro Pro Phe Glu Tyr Met Ile Leu Ala Thr Ile
 90                  95                 100                 105

atc gcc aac tgc atc gtg ctg gcc ctg gag cag cac ctc cct gat ggg      508
Ile Ala Asn Cys Ile Val Leu Ala Leu Glu Gln His Leu Pro Asp Gly
                110                 115                 120

gac aaa acg ccc atg tcc gag cgg ctg gac gac acg gag ccc tat ttc      556
Asp Lys Thr Pro Met Ser Glu Arg Leu Asp Asp Thr Glu Pro Tyr Phe
            125                 130                 135

atc ggg atc ttt tgc ttc gag gca ggg atc aaa atc atc gct ctg ggc      604
Ile Gly Ile Phe Cys Phe Glu Ala Gly Ile Lys Ile Ile Ala Leu Gly
        140                 145                 150

ttt gtc ttc cac aag ggc tct tac ctg cgg aac ggc tgg aac gtc atg      652
Phe Val Phe His Lys Gly Ser Tyr Leu Arg Asn Gly Trp Asn Val Met
    155                 160                 165

gac ttc gtg gtc gtc ctc aca ggg atc ctt gcc acg gct gga act gac      700
Asp Phe Val Val Val Leu Thr Gly Ile Leu Ala Thr Ala Gly Thr Asp
170                 175                 180                 185

ttc gac ctg cga aca ctg agg gct gtg cgt gtg ctg agg ccc ctg aag      748
Phe Asp Leu Arg Thr Leu Arg Ala Val Arg Val Leu Arg Pro Leu Lys
                190                 195                 200

ctg gtg tct ggg att cca agt ttg cag gtg gtg ctc aag tcc atc atg      796
Leu Val Ser Gly Ile Pro Ser Leu Gln Val Val Leu Lys Ser Ile Met
            205                 210                 215

aag gcc atg gtt cca ctc ctg cag att ggg ctg ctt ctc ttc ttt gcc      844
Lys Ala Met Val Pro Leu Leu Gln Ile Gly Leu Leu Leu Phe Phe Ala
        220                 225                 230

atc ctc atg ttt gcc atc att ggc ctg gag ttc tac atg ggc aag ttc      892
Ile Leu Met Phe Ala Ile Ile Gly Leu Glu Phe Tyr Met Gly Lys Phe
    235                 240                 245

cac aag gcc tgt ttc ccc aac agc aca gat gcg gag ccc gtg ggt gac      940
His Lys Ala Cys Phe Pro Asn Ser Thr Asp Ala Glu Pro Val Gly Asp
250                 255                 260                 265

ttc ccc tgt ggc aag gag gcc cca gcc cgg ctg tgc gag ggc gac act      988
Phe Pro Cys Gly Lys Glu Ala Pro Ala Arg Leu Cys Glu Gly Asp Thr
                270                 275                 280

gag tgc cgg gag tac tgg cca gga ccc aac ttt ggc atc acc aac ttt     1036
Glu Cys Arg Glu Tyr Trp Pro Gly Pro Asn Phe Gly Ile Thr Asn Phe
            285                 290                 295

gac aat atc ctg ttt gcc atc ttg acg gtg ttc cag tgc atc acc atg     1084
Asp Asn Ile Leu Phe Ala Ile Leu Thr Val Phe Gln Cys Ile Thr Met
        300                 305                 310

gag ggc tgg act gac atc ctc tat aat aca aac gat gcg gcc ggc aac     1132
Glu Gly Trp Thr Asp Ile Leu Tyr Asn Thr Asn Asp Ala Ala Gly Asn
    315                 320                 325

acc tgg aac tgg ctc tac ttc atc cct ctc atc atc atc ggc tcc ttc     1180
Thr Trp Asn Trp Leu Tyr Phe Ile Pro Leu Ile Ile Ile Gly Ser Phe
330                 335                 340                 345

ttc atg ctc aac ctg gtg ctg ggc gtg ctc tcg ggg gag ttt gcc aag     1228
Phe Met Leu Asn Leu Val Leu Gly Val Leu Ser Gly Glu Phe Ala Lys
                350                 355                 360
```

-continued

```
gag cga gag agg gtg gag aac cgc cgc gcc ttc ctg aag ctg cgc cgg     1276
Glu Arg Glu Arg Val Glu Asn Arg Arg Ala Phe Leu Lys Leu Arg Arg
            365                 370                 375

cag cag cag atc gag cga gag ctc aac ggg tac ctg gag tgg atc ttc     1324
Gln Gln Gln Ile Glu Arg Glu Leu Asn Gly Tyr Leu Glu Trp Ile Phe
        380                 385                 390

aag gcg gag gaa gtc atg ctg gcc gag gag gac agg aat gca gag gag     1372
Lys Ala Glu Glu Val Met Leu Ala Glu Glu Asp Arg Asn Ala Glu Glu
    395                 400                 405

aag tcc cct ttg gac gtg ctg aag aga gcg gcc acc aag aag agc aga     1420
Lys Ser Pro Leu Asp Val Leu Lys Arg Ala Ala Thr Lys Lys Ser Arg
410                 415                 420                 425

aat gac ctg atc cac gca gag gag gga gag gac cgg ttt gca gat ctc     1468
Asn Asp Leu Ile His Ala Glu Glu Gly Glu Asp Arg Phe Ala Asp Leu
                430                 435                 440

tgt gct gtt gga tcc ccc ttc gcc cgc gcc agc ctc aag agc ggg aag     1516
Cys Ala Val Gly Ser Pro Phe Ala Arg Ala Ser Leu Lys Ser Gly Lys
            445                 450                 455

aca gag agc tcg tca tac ttc cgg agg aag gag aag atg ttc cgg ttt     1564
Thr Glu Ser Ser Ser Tyr Phe Arg Arg Lys Glu Lys Met Phe Arg Phe
        460                 465                 470

ttt atc cgg cgc atg gtg aag gct cag agc ttc tac tgg gtg gtg ctg     1612
Phe Ile Arg Arg Met Val Lys Ala Gln Ser Phe Tyr Trp Val Val Leu
    475                 480                 485

tgc gtg gtg gcc ctg aac aca ctg tgt gtg gcc atg gtg cat tac aac     1660
Cys Val Val Ala Leu Asn Thr Leu Cys Val Ala Met Val His Tyr Asn
490                 495                 500                 505

cag ccg cgg cgg ctt acc acg acc ctg tat ttt gca gag ttt gtt ttc     1708
Gln Pro Arg Arg Leu Thr Thr Thr Leu Tyr Phe Ala Glu Phe Val Phe
                510                 515                 520

ctg ggt ctc ttc ctc aca gag atg tcc ctg aag atg tat ggc ctg ggg     1756
Leu Gly Leu Phe Leu Thr Glu Met Ser Leu Lys Met Tyr Gly Leu Gly
            525                 530                 535

ccc aga agc tac ttc cgg tcc tcc ttc aac tgc ttc gac ttt ggg gtc     1804
Pro Arg Ser Tyr Phe Arg Ser Ser Phe Asn Cys Phe Asp Phe Gly Val
        540                 545                 550

atc gtg ggg agc gtc ttt gaa gtg gtc tgg gcg gcc atc aag ccg gga     1852
Ile Val Gly Ser Val Phe Glu Val Val Trp Ala Ala Ile Lys Pro Gly
    555                 560                 565

agc tcc ttt ggg atc agt gtg ctg cgg gcc ctc cgc ctg ctg agg atc     1900
Ser Ser Phe Gly Ile Ser Val Leu Arg Ala Leu Arg Leu Leu Arg Ile
570                 575                 580                 585

ttc aaa gtc acg aag tac tgg agc tcc ctg cgg aac ctg gtg gtg tcc     1948
Phe Lys Val Thr Lys Tyr Trp Ser Ser Leu Arg Asn Leu Val Val Ser
                590                 595                 600

ctg ctg aac tcc atg aag tcc atc atc agc ctg ctc ttc ttg ctc ttc     1996
Leu Leu Asn Ser Met Lys Ser Ile Ile Ser Leu Leu Phe Leu Leu Phe
            605                 610                 615

ctg ttc att gtg gtc ttc gcc ctg ctg ggg atg cag ctg ttt ggg gga     2044
Leu Phe Ile Val Val Phe Ala Leu Leu Gly Met Gln Leu Phe Gly Gly
        620                 625                 630

cag ttc aac ttc cag gat gag act ccc aca acc aac ttc gac acc ttc     2092
Gln Phe Asn Phe Gln Asp Glu Thr Pro Thr Thr Asn Phe Asp Thr Phe
    635                 640                 645

cct gcc gcc atc ctc act gtc ttc cag atc ctg acg gga gag gac tgg     2140
Pro Ala Ala Ile Leu Thr Val Phe Gln Ile Leu Thr Gly Glu Asp Trp
650                 655                 660                 665

aat gca gtg atg tat cac ggg atc gaa tcg caa ggc ggc gtc agc aaa     2188
Asn Ala Val Met Tyr His Gly Ile Glu Ser Gln Gly Gly Val Ser Lys
                670                 675                 680
```

```
ggc atg ttc tcg tcc ttt tac ttc att gtc ctg aca ctg ttc gga aac     2236
Gly Met Phe Ser Ser Phe Tyr Phe Ile Val Leu Thr Leu Phe Gly Asn
            685                 690                 695

tac act ctg ctg aat gtc ttt ctg gcc atc gct gtg gac aac ctg gcc     2284
Tyr Thr Leu Leu Asn Val Phe Leu Ala Ile Ala Val Asp Asn Leu Ala
        700                 705                 710

aac gcc caa gag ctg acc aag gat gaa gag gag atg gaa gaa gca gcc     2332
Asn Ala Gln Glu Leu Thr Lys Asp Glu Glu Glu Met Glu Glu Ala Ala
    715                 720                 725

aat cag aag ctt gct ctg caa aag gcc aaa gaa gtg gct gaa gtc agc     2380
Asn Gln Lys Leu Ala Leu Gln Lys Ala Lys Glu Val Ala Glu Val Ser
730                 735                 740                 745

ccc atg tct gcc gcg aac atc tcc atc gcc gcc agg cag cag aac tcg     2428
Pro Met Ser Ala Ala Asn Ile Ser Ile Ala Ala Arg Gln Gln Asn Ser
                750                 755                 760

gcc aag gcg cgc tcg gtg tgg gag cag cgg gcc agc cag cta cgg ctg     2476
Ala Lys Ala Arg Ser Val Trp Glu Gln Arg Ala Ser Gln Leu Arg Leu
            765                 770                 775

cag aac ctg cgg gcc agc tgc gag gcg ctg tac agc gag atg gac ccc     2524
Gln Asn Leu Arg Ala Ser Cys Glu Ala Leu Tyr Ser Glu Met Asp Pro
        780                 785                 790

gag gag cgg ctg cgc ttc gcc act acg cgc cac ctg cgg ccc gac atg     2572
Glu Glu Arg Leu Arg Phe Ala Thr Thr Arg His Leu Arg Pro Asp Met
    795                 800                 805

aag acg cac ctg gac cgg ccg ctg gtg gtg gag ctg ggc cgc gac ggc     2620
Lys Thr His Leu Asp Arg Pro Leu Val Val Glu Leu Gly Arg Asp Gly
810                 815                 820                 825

gcg cgg ggg ccc gtg gga ggc aaa gcc cga cct gag gct gcg gag gcc     2668
Ala Arg Gly Pro Val Gly Gly Lys Ala Arg Pro Glu Ala Ala Glu Ala
                830                 835                 840

ccc gag ggc gtc gac cct ccg cgc agg cac cac cgg cac cgc gac aag     2716
Pro Glu Gly Val Asp Pro Pro Arg Arg His His Arg His Arg Asp Lys
            845                 850                 855

gac aag acc ccc gcg gcg ggg gac cag gac cga gca gag gcc ccg aag     2764
Asp Lys Thr Pro Ala Ala Gly Asp Gln Asp Arg Ala Glu Ala Pro Lys
        860                 865                 870

gcg gag agc ggg gag ccc ggt gcc cgg gag gag cgg ccg cgg ccg cac     2812
Ala Glu Ser Gly Glu Pro Gly Ala Arg Glu Glu Arg Pro Arg Pro His
    875                 880                 885

cgc agc cac agc aag gag gcc gcg ggg ccc ccg gag gcg cgg agc gag     2860
Arg Ser His Ser Lys Glu Ala Ala Gly Pro Pro Glu Ala Arg Ser Glu
890                 895                 900                 905

cgc ggc cga ggc cca ggc ccc gag ggc ggc cgg cgg cac cac cgg cgc     2908
Arg Gly Arg Gly Pro Gly Pro Glu Gly Gly Arg Arg His His Arg Arg
                910                 915                 920

ggc tcc ccg gag gag gcg gcc gag cgg gag ccc cga cgc cac cgc gcg     2956
Gly Ser Pro Glu Glu Ala Ala Glu Arg Glu Pro Arg Arg His Arg Ala
            925                 930                 935

cac cgg cac cag gat ccg agc aag gag tgc gcc ggc gcc aag ggc gag     3004
His Arg His Gln Asp Pro Ser Lys Glu Cys Ala Gly Ala Lys Gly Glu
        940                 945                 950

cgg cgc gcg cgg cac cgc ggc ggc ccc cga gcg ggg ccc cgg gag gcg     3052
Arg Arg Ala Arg His Arg Gly Gly Pro Arg Ala Gly Pro Arg Glu Ala
    955                 960                 965

gag agc ggg gag gag ccg gcg cgg cgg cac cgg gcc cgg cac aag gcg     3100
Glu Ser Gly Glu Glu Pro Ala Arg Arg His Arg Ala Arg His Lys Ala
970                 975                 980                 985

cag cct gct cac gag gct gtg gag aag gag acc acg gag aag gag gcc     3148
Gln Pro Ala His Glu Ala Val Glu Lys Glu Thr Thr Glu Lys Glu Ala
```

-continued

```
            990                 995                 1000

acg gag aag gag gct gag ata gtg gaa gcc gac aag gaa aag gag ctc      3196
Thr Glu Lys Glu Ala Glu Ile Val Glu Ala Asp Lys Glu Lys Glu Leu
            1005                1010                1015

cgg aac cac cag ccc cgg gag cca cac tgt gac ctg gag acc agt ggg      3244
Arg Asn His Gln Pro Arg Glu Pro His Cys Asp Leu Glu Thr Ser Gly
        1020                1025                1030

act gtg act gtg ggt ccc atg cac aca ctg ccc agc acc tgt ctc cag      3292
Thr Val Thr Val Gly Pro Met His Thr Leu Pro Ser Thr Cys Leu Gln
    1035                1040                1045

aag gtg gag gaa cag cca gag gat gca gac aat cag cgg aac gtc act      3340
Lys Val Glu Glu Gln Pro Glu Asp Ala Asp Asn Gln Arg Asn Val Thr
1050                1055                1060                1065

cgc atg ggc agt cag ccc cca gac ccg aac act att gta cat atc cca      3388
Arg Met Gly Ser Gln Pro Pro Asp Pro Asn Thr Ile Val His Ile Pro
            1070                1075                1080

gtg atg ctg acg ggc cct ctt ggg gaa gcc acg gtc gtt ccc agt ggt      3436
Val Met Leu Thr Gly Pro Leu Gly Glu Ala Thr Val Val Pro Ser Gly
            1085                1090                1095

aac gtg gac ctg gaa agc caa gca gag ggg aag aag gag gtg gaa gcg      3484
Asn Val Asp Leu Glu Ser Gln Ala Glu Gly Lys Lys Glu Val Glu Ala
        1100                1105                1110

gat gac gtg atg agg agc ggc ccc cgg cct atc gtc cca tac agc tcc      3532
Asp Asp Val Met Arg Ser Gly Pro Arg Pro Ile Val Pro Tyr Ser Ser
    1115                1120                1125

atg ttc tgt tta agc ccc acc aac ctg ctc cgc cgc ttc tgc cac tac      3580
Met Phe Cys Leu Ser Pro Thr Asn Leu Leu Arg Arg Phe Cys His Tyr
1130                1135                1140                1145

atc gtg acc atg agg tac ttc gag gtg gtc att ctc gtg gtc atc gcc      3628
Ile Val Thr Met Arg Tyr Phe Glu Val Val Ile Leu Val Val Ile Ala
            1150                1155                1160

ttg agc agc atc gcc ctg gct gct gag gac cca gtg cgc aca gac tcg      3676
Leu Ser Ser Ile Ala Leu Ala Ala Glu Asp Pro Val Arg Thr Asp Ser
            1165                1170                1175

ccc agg aac aac gct ctg aaa tac ctg gat tac att ttc act ggt gtc      3724
Pro Arg Asn Asn Ala Leu Lys Tyr Leu Asp Tyr Ile Phe Thr Gly Val
        1180                1185                1190

ttt acc ttt gag atg gtg ata aag atg atc gac ttg gga ctg ctg ctt      3772
Phe Thr Phe Glu Met Val Ile Lys Met Ile Asp Leu Gly Leu Leu Leu
    1195                1200                1205

cac cct gga gcc tat ttc cgg gac ttg tgg aac att ctg gac ttc att      3820
His Pro Gly Ala Tyr Phe Arg Asp Leu Trp Asn Ile Leu Asp Phe Ile
1210                1215                1220                1225

gtg gtc agt ggc gcc ctg gtg gcg ttt gct ttc tca gga tcc aaa ggg      3868
Val Val Ser Gly Ala Leu Val Ala Phe Ala Phe Ser Gly Ser Lys Gly
            1230                1235                1240

aaa gac atc aat acc atc aag tct ctg aga gtc ctt cgt gtc ctg cgg      3916
Lys Asp Ile Asn Thr Ile Lys Ser Leu Arg Val Leu Arg Val Leu Arg
            1245                1250                1255

ccc ctc aag acc atc aaa cgg ctg ccc aag ctc aag gct gtg ttt gac      3964
Pro Leu Lys Thr Ile Lys Arg Leu Pro Lys Leu Lys Ala Val Phe Asp
        1260                1265                1270

tgt gtg gtg aac tcc ctg aag aat gtc ctc aac atc ttg att gtc tac      4012
Cys Val Val Asn Ser Leu Lys Asn Val Leu Asn Ile Leu Ile Val Tyr
    1275                1280                1285

atg ctc ttc atg ttc ata ttt gcc gtc att gcg gtg cag ctc ttc aaa      4060
Met Leu Phe Met Phe Ile Phe Ala Val Ile Ala Val Gln Leu Phe Lys
1290                1295                1300                1305

ggg aag ttt ttc tac tgc aca gat gaa tcc aag gag ctg gag agg gac      4108
```

-continued

```
Gly Lys Phe Phe Tyr Cys Thr Asp Glu Ser Lys Glu Leu Glu Arg Asp
                1310                1315                1320

tgc agg ggt cag tat ttg gat tat gag aag gag gaa gtg gaa gct cag      4156
Cys Arg Gly Gln Tyr Leu Asp Tyr Glu Lys Glu Glu Val Glu Ala Gln
            1325                1330                1335

ccc agg cag tgg aag aaa tac gac ttt cac tac gac aat gtg ctc tgg      4204
Pro Arg Gln Trp Lys Lys Tyr Asp Phe His Tyr Asp Asn Val Leu Trp
        1340                1345                1350

gct ctg ctg acg ctg ttc aca gtg tcc acg gga gaa ggc tgg ccc atg      4252
Ala Leu Leu Thr Leu Phe Thr Val Ser Thr Gly Glu Gly Trp Pro Met
    1355                1360                1365

gtg ctg aaa cac tcc gtg gat gcc acc tat gag gag cag ggt cca agc      4300
Val Leu Lys His Ser Val Asp Ala Thr Tyr Glu Glu Gln Gly Pro Ser
1370                1375                1380                1385

cct ggg tac cgc atg gag ctg tcc atc ttc tac gtg gtc tac ttt gtg      4348
Pro Gly Tyr Arg Met Glu Leu Ser Ile Phe Tyr Val Val Tyr Phe Val
                1390                1395                1400

gtc ttt ccc ttc ttc ttc gtc aac atc ttt gtg gct ttg atc atc atc      4396
Val Phe Pro Phe Phe Phe Val Asn Ile Phe Val Ala Leu Ile Ile Ile
            1405                1410                1415

acc ttc cag gag cag ggg gac aag gtg atg tct gaa tgc agc ctg gag      4444
Thr Phe Gln Glu Gln Gly Asp Lys Val Met Ser Glu Cys Ser Leu Glu
        1420                1425                1430

aag aac gag agg gct tgc att gac ttc gcc atc agc gcc aaa ccc ctg      4492
Lys Asn Glu Arg Ala Cys Ile Asp Phe Ala Ile Ser Ala Lys Pro Leu
    1435                1440                1445

aca cgg tac atg ccc caa aac cgg cag tcg ttc cag tat aag acg tgg      4540
Thr Arg Tyr Met Pro Gln Asn Arg Gln Ser Phe Gln Tyr Lys Thr Trp
1450                1455                1460                1465

aca ttt gtg gtc tcc ccg ccc ttt gaa tac ttc atc atg gcc atg ata      4588
Thr Phe Val Val Ser Pro Pro Phe Glu Tyr Phe Ile Met Ala Met Ile
                1470                1475                1480

gcc ctc aac act gtg gtg ctg atg atg aag ttc tat gat gca ccc tat      4636
Ala Leu Asn Thr Val Val Leu Met Met Lys Phe Tyr Asp Ala Pro Tyr
            1485                1490                1495

gag tac gag ctg atg ctg aaa tgc ctg aac atc gtg ttc aca tcc atg      4684
Glu Tyr Glu Leu Met Leu Lys Cys Leu Asn Ile Val Phe Thr Ser Met
        1500                1505                1510

ttc tcc atg gaa tgc gtg ctg aag atc atc gcc ttt ggg gtg ctg aac      4732
Phe Ser Met Glu Cys Val Leu Lys Ile Ile Ala Phe Gly Val Leu Asn
    1515                1520                1525

tat ttc aga gat gcc tgg aat gtc ttt gac ttt gtc act gtg ttg gga      4780
Tyr Phe Arg Asp Ala Trp Asn Val Phe Asp Phe Val Thr Val Leu Gly
1530                1535                1540                1545

agt att act gat att tta gta aca gag att gcg gaa acg aac aat ttc      4828
Ser Ile Thr Asp Ile Leu Val Thr Glu Ile Ala Glu Thr Asn Asn Phe
                1550                1555                1560

atc aac ctc agc ttc ctc cgc ctc ttt cga gct gcg cgg ctg atc aag      4876
Ile Asn Leu Ser Phe Leu Arg Leu Phe Arg Ala Ala Arg Leu Ile Lys
            1565                1570                1575

ctg ctc cgc cag ggc tac acc atc cgc atc ctg ctg tgg acc ttt gtc      4924
Leu Leu Arg Gln Gly Tyr Thr Ile Arg Ile Leu Leu Trp Thr Phe Val
        1580                1585                1590

cag tcc ttc aag gcc ctg ccc tac gtg tgt ctg ctc att gcc atg ctg      4972
Gln Ser Phe Lys Ala Leu Pro Tyr Val Cys Leu Leu Ile Ala Met Leu
    1595                1600                1605

ttc ttc atc tac gcc atc atc ggc atg cag gtg ttt ggg aat att gcc      5020
Phe Phe Ile Tyr Ala Ile Ile Gly Met Gln Val Phe Gly Asn Ile Ala
1610                1615                1620                1625
```

-continued

```
ctg gat gat gac acc agc atc aac cgc cac aac aac ttc cgg acg ttt      5068
Leu Asp Asp Asp Thr Ser Ile Asn Arg His Asn Asn Phe Arg Thr Phe
                1630                1635                1640

ttg caa gcc ctg atg ctg ctg ttc agg agc gcc acg ggg gag gcc tgg      5116
Leu Gln Ala Leu Met Leu Leu Phe Arg Ser Ala Thr Gly Glu Ala Trp
            1645                1650                1655

cac gag atc atg ctg tcc tgc ctg agc aac cag gcc tgt gat gag cag      5164
His Glu Ile Met Leu Ser Cys Leu Ser Asn Gln Ala Cys Asp Glu Gln
        1660                1665                1670

gcc aat gcc acc gag tgt gga agt gac ttt gcc tac ttc tac ttc gtc      5212
Ala Asn Ala Thr Glu Cys Gly Ser Asp Phe Ala Tyr Phe Tyr Phe Val
    1675                1680                1685

tcc ttc atc ttc ctg tgc tcc ttt ctg atg ttg aac ctc ttt gtg gct      5260
Ser Phe Ile Phe Leu Cys Ser Phe Leu Met Leu Asn Leu Phe Val Ala
1690                1695                1700                1705

gtg atc atg gac aat ttt gag tac ctc acg cgg gac tct tcc atc cta      5308
Val Ile Met Asp Asn Phe Glu Tyr Leu Thr Arg Asp Ser Ser Ile Leu
                1710                1715                1720

ggt cct cac cac ttg gat gag ttc atc cgg gtc tgg gct gaa tac gac      5356
Gly Pro His His Leu Asp Glu Phe Ile Arg Val Trp Ala Glu Tyr Asp
            1725                1730                1735

ccg gct gcg tgt ggg cgc atc agt tac aat gac atg ttt gag atg ctg      5404
Pro Ala Ala Cys Gly Arg Ile Ser Tyr Asn Asp Met Phe Glu Met Leu
        1740                1745                1750

aaa cac atg tcc ccg cct ctg ggg ctg ggg aag aaa tgc cct gct cga      5452
Lys His Met Ser Pro Pro Leu Gly Leu Gly Lys Lys Cys Pro Ala Arg
    1755                1760                1765

gtt gct tac aag cgc ctg gtt cgc atg aac atg ccc atc tcc aac gag      5500
Val Ala Tyr Lys Arg Leu Val Arg Met Asn Met Pro Ile Ser Asn Glu
1770                1775                1780                1785

gac atg act gtt cac ttc acg tcc acg ctg atg gcc ctc atc cgg acg      5548
Asp Met Thr Val His Phe Thr Ser Thr Leu Met Ala Leu Ile Arg Thr
                1790                1795                1800

gca ctg gag atc aag ctg gcc cca gct ggg aca aag cag cat cag tgt      5596
Ala Leu Glu Ile Lys Leu Ala Pro Ala Gly Thr Lys Gln His Gln Cys
            1805                1810                1815

gac gcg gag ttg agg aag gag att tcc gtt gtg tgg gcc aat ctg ccc      5644
Asp Ala Glu Leu Arg Lys Glu Ile Ser Val Val Trp Ala Asn Leu Pro
        1820                1825                1830

cag aag act ttg gac ttg ctg gta cca ccc cat aag cct gat gag atg      5692
Gln Lys Thr Leu Asp Leu Leu Val Pro Pro His Lys Pro Asp Glu Met
    1835                1840                1845

aca gtg ggg aag gtt tat gca gct ctg atg ata ttt gac ttc tac aag      5740
Thr Val Gly Lys Val Tyr Ala Ala Leu Met Ile Phe Asp Phe Tyr Lys
1850                1855                1860                1865

cag aac aaa acc acc aga gac cag atg cag cag gct cct gga ggc ctc      5788
Gln Asn Lys Thr Thr Arg Asp Gln Met Gln Gln Ala Pro Gly Gly Leu
                1870                1875                1880

tcc cag atg ggt cct gtg tcc ctg ttc cac cct ctg aag gcc acc ctg      5836
Ser Gln Met Gly Pro Val Ser Leu Phe His Pro Leu Lys Ala Thr Leu
            1885                1890                1895

gag cag aca cag ccg gct gtg ctc cga gga gcc cgg gtt ttc ctt cga      5884
Glu Gln Thr Gln Pro Ala Val Leu Arg Gly Ala Arg Val Phe Leu Arg
        1900                1905                1910

cag aag agt tcc acc tcc ctc agc aat ggc ggg gcc ata caa aac caa      5932
Gln Lys Ser Ser Thr Ser Leu Ser Asn Gly Gly Ala Ile Gln Asn Gln
    1915                1920                1925

gag agt ggc atc aaa gag tct gtc tcc tgg ggc act caa agg acc cag      5980
Glu Ser Gly Ile Lys Glu Ser Val Ser Trp Gly Thr Gln Arg Thr Gln
1930                1935                1940                1945
```

-continued

```
gat gca ccc cat gag gcc agg cca ccc ctg gag cgt ggc cac tcc aca     6028
Asp Ala Pro His Glu Ala Arg Pro Pro Leu Glu Arg Gly His Ser Thr
                1950                1955                1960

gag atc cct gtg ggg cgg tca gga gca ctg gct gtg gac gtt cag atg     6076
Glu Ile Pro Val Gly Arg Ser Gly Ala Leu Ala Val Asp Val Gln Met
            1965                1970                1975

cag agc ata acc cgg agg ggc cct gat ggg gag ccc cag cct ggg ctg     6124
Gln Ser Ile Thr Arg Arg Gly Pro Asp Gly Glu Pro Gln Pro Gly Leu
        1980                1985                1990

gag agc cag ggt cga gcg gcc tcc atg ccc cgc ctt gcg gcc gag act     6172
Glu Ser Gln Gly Arg Ala Ala Ser Met Pro Arg Leu Ala Ala Glu Thr
    1995                2000                2005

cag ccc gtc aca gat gcc agc ccc atg aag cgc tcc atc tcc acg ctg     6220
Gln Pro Val Thr Asp Ala Ser Pro Met Lys Arg Ser Ile Ser Thr Leu
2010                2015                2020                2025

gcc cag cgg ccc cgt ggg act cat ctt tgc agc acc acc ccg gac cgc     6268
Ala Gln Arg Pro Arg Gly Thr His Leu Cys Ser Thr Thr Pro Asp Arg
                2030                2035                2040

cca ccc cct agc cag gcg tcg tcg cac cac cac cac cac cgc tgc cac     6316
Pro Pro Pro Ser Gln Ala Ser Ser His His His His His Arg Cys His
            2045                2050                2055

cgc cgc agg gac agg aag cag agg tcc ctg gag aag ggg ccc agc ctg     6364
Arg Arg Arg Asp Arg Lys Gln Arg Ser Leu Glu Lys Gly Pro Ser Leu
        2060                2065                2070

tct gcc gat atg gat ggc gca cca agc agt gct gtg ggg ccg ggg ctg     6412
Ser Ala Asp Met Asp Gly Ala Pro Ser Ser Ala Val Gly Pro Gly Leu
    2075                2080                2085

ccc ccg gga gag ggg cct aca ggc tgc cgg cgg gaa cga gag cgc cgg     6460
Pro Pro Gly Glu Gly Pro Thr Gly Cys Arg Arg Glu Arg Glu Arg Arg
2090                2095                2100                2105

cag gag cgg ggc cgg tcc cag gag cgg agg cag ccc tca tcc tcc tcc     6508
Gln Glu Arg Gly Arg Ser Gln Glu Arg Arg Gln Pro Ser Ser Ser Ser
                2110                2115                2120

tcg gag aag cag cgc ttc tac tcc tgc gac cgc ttt ggg ggc cgt gag     6556
Ser Glu Lys Gln Arg Phe Tyr Ser Cys Asp Arg Phe Gly Gly Arg Glu
            2125                2130                2135

ccc ccg aag ccc aag ccc tcc ctc agc agc cac cca acg tcg cca aca     6604
Pro Pro Lys Pro Lys Pro Ser Leu Ser Ser His Pro Thr Ser Pro Thr
        2140                2145                2150

gct ggc cag gag ccg gga ccc cac cca cag ggc agt ggt tcc gtg aat     6652
Ala Gly Gln Glu Pro Gly Pro His Pro Gln Gly Ser Gly Ser Val Asn
    2155                2160                2165

ggg agc ccc ttg ctg tca aca tct ggt gct agc acc ccc ggc cgc ggt     6700
Gly Ser Pro Leu Leu Ser Thr Ser Gly Ala Ser Thr Pro Gly Arg Gly
2170                2175                2180                2185

ggg cgg agg cag ctc ccc cag acg ccc ctg act ccc cgc ccc agc atc     6748
Gly Arg Arg Gln Leu Pro Gln Thr Pro Leu Thr Pro Arg Pro Ser Ile
                2190                2195                2200

acc tac aag acg gcc aac tcc tca ccc atc cac ttc gcc ggg gct cag     6796
Thr Tyr Lys Thr Ala Asn Ser Ser Pro Ile His Phe Ala Gly Ala Gln
            2205                2210                2215

acc agc ctc cct gcc ttc tcc cca ggc cgg ctc agc cgt ggg ctt tcc     6844
Thr Ser Leu Pro Ala Phe Ser Pro Gly Arg Leu Ser Arg Gly Leu Ser
        2220                2225                2230

gaa cac aac gcc ctg ctg cag aga gac ccc ctc agc cag ccc ctg gcc     6892
Glu His Asn Ala Leu Leu Gln Arg Asp Pro Leu Ser Gln Pro Leu Ala
    2235                2240                2245

cct ggc tct cga att ggc tct gac cct tac ctg ggg cag cgt ctg gac     6940
Pro Gly Ser Arg Ile Gly Ser Asp Pro Tyr Leu Gly Gln Arg Leu Asp
```

```
2250                2255                2260                2265

agt gag gcc tct gtc cac gcc ctg cct gag gac acg ctc act ttc gag     6988
Ser Glu Ala Ser Val His Ala Leu Pro Glu Asp Thr Leu Thr Phe Glu
                2270                2275                2280

gag gct gtg gcc acc aac tcg ggc cgc tcc tcc agg act tcc tac gtg     7036
Glu Ala Val Ala Thr Asn Ser Gly Arg Ser Ser Arg Thr Ser Tyr Val
            2285                2290                2295

tcc tcc ctg acc tcc cag tct cac cct ctc cgc cgc gtg ccc aac ggt     7084
Ser Ser Leu Thr Ser Gln Ser His Pro Leu Arg Arg Val Pro Asn Gly
        2300                2305                2310

tac cac tgc acc ctg gga ctc agc tcg ggt ggc cga gca cgg cac agc     7132
Tyr His Cys Thr Leu Gly Leu Ser Ser Gly Gly Arg Ala Arg His Ser
    2315                2320                2325

tac cac cac cct gac caa gac cac tgg tgc tag ctgcaccgtg accgctcaga   7185
Tyr His His Pro Asp Gln Asp His Trp Cys
2330                2335                2340

cgcctgcatg cagcaggcgt gtgttccagt ggatgagttt tatcatccac acggggcagt   7245

cggccctcgg gggaggcctt gcccaccttg gtgaggctcc tgtggcccct ccctccccct   7305

cctcccctct tttactctag acgacgaata aagccctgtt gcttgagtgt acgtaccgc    7364


<210> SEQ ID NO 11
<211> LENGTH: 2339
<212> TYPE: PRT
<213> ORGANISM: Homo sapiens

<400> SEQUENCE: 11

Met Val Arg Phe Gly Asp Glu Leu Gly Gly Arg Tyr Gly Gly Pro Gly
 1               5                  10                  15

Gly Gly Glu Arg Ala Arg Gly Gly Gly Ala Gly Gly Ala Gly Gly Pro
            20                  25                  30

Gly Pro Gly Gly Leu Gln Pro Gly Gln Arg Val Leu Tyr Lys Gln Ser
        35                  40                  45

Ile Ala Gln Arg Ala Arg Thr Met Ala Leu Tyr Asn Pro Ile Pro Val
    50                  55                  60

Lys Gln Asn Cys Phe Thr Val Asn Arg Ser Leu Phe Val Phe Ser Glu
65                  70                  75                  80

Asp Asn Val Val Arg Lys Tyr Ala Lys Arg Ile Thr Glu Trp Pro Pro
                85                  90                  95

Phe Glu Tyr Met Ile Leu Ala Thr Ile Ile Ala Asn Cys Ile Val Leu
            100                 105                 110

Ala Leu Glu Gln His Leu Pro Asp Gly Asp Lys Thr Pro Met Ser Glu
        115                 120                 125

Arg Leu Asp Asp Thr Glu Pro Tyr Phe Ile Gly Ile Phe Cys Phe Glu
    130                 135                 140

Ala Gly Ile Lys Ile Ile Ala Leu Gly Phe Val Phe His Lys Gly Ser
145                 150                 155                 160

Tyr Leu Arg Asn Gly Trp Asn Val Met Asp Phe Val Val Val Leu Thr
                165                 170                 175

Gly Ile Leu Ala Thr Ala Gly Thr Asp Phe Asp Leu Arg Thr Leu Arg
            180                 185                 190

Ala Val Arg Val Leu Arg Pro Leu Lys Leu Val Ser Gly Ile Pro Ser
        195                 200                 205

Leu Gln Val Val Leu Lys Ser Ile Met Lys Ala Met Val Pro Leu Leu
    210                 215                 220

Gln Ile Gly Leu Leu Leu Phe Phe Ala Ile Leu Met Phe Ala Ile Ile
```

-continued

```
225                 230                 235                 240

Gly Leu Glu Phe Tyr Met Gly Lys Phe His Lys Ala Cys Phe Pro Asn
                245                 250                 255

Ser Thr Asp Ala Glu Pro Val Gly Asp Phe Pro Cys Gly Lys Glu Ala
            260                 265                 270

Pro Ala Arg Leu Cys Glu Gly Asp Thr Glu Cys Arg Glu Tyr Trp Pro
        275                 280                 285

Gly Pro Asn Phe Gly Ile Thr Asn Phe Asp Asn Ile Leu Phe Ala Ile
    290                 295                 300

Leu Thr Val Phe Gln Cys Ile Thr Met Glu Gly Trp Thr Asp Ile Leu
305                 310                 315                 320

Tyr Asn Thr Asn Asp Ala Ala Gly Asn Thr Trp Asn Trp Leu Tyr Phe
                325                 330                 335

Ile Pro Leu Ile Ile Ile Gly Ser Phe Phe Met Leu Asn Leu Val Leu
            340                 345                 350

Gly Val Leu Ser Gly Glu Phe Ala Lys Glu Arg Glu Arg Val Glu Asn
        355                 360                 365

Arg Arg Ala Phe Leu Lys Leu Arg Arg Gln Gln Gln Ile Glu Arg Glu
    370                 375                 380

Leu Asn Gly Tyr Leu Glu Trp Ile Phe Lys Ala Glu Glu Val Met Leu
385                 390                 395                 400

Ala Glu Glu Asp Arg Asn Ala Glu Glu Lys Ser Pro Leu Asp Val Leu
                405                 410                 415

Lys Arg Ala Ala Thr Lys Lys Ser Arg Asn Asp Leu Ile His Ala Glu
            420                 425                 430

Glu Gly Glu Asp Arg Phe Ala Asp Leu Cys Ala Val Gly Ser Pro Phe
        435                 440                 445

Ala Arg Ala Ser Leu Lys Ser Gly Lys Thr Glu Ser Ser Ser Tyr Phe
    450                 455                 460

Arg Arg Lys Glu Lys Met Phe Arg Phe Phe Ile Arg Arg Met Val Lys
465                 470                 475                 480

Ala Gln Ser Phe Tyr Trp Val Val Leu Cys Val Val Ala Leu Asn Thr
                485                 490                 495

Leu Cys Val Ala Met Val His Tyr Asn Gln Pro Arg Arg Leu Thr Thr
            500                 505                 510

Thr Leu Tyr Phe Ala Glu Phe Val Phe Leu Gly Leu Phe Leu Thr Glu
        515                 520                 525

Met Ser Leu Lys Met Tyr Gly Leu Gly Pro Arg Ser Tyr Phe Arg Ser
    530                 535                 540

Ser Phe Asn Cys Phe Asp Phe Gly Val Ile Val Gly Ser Val Phe Glu
545                 550                 555                 560

Val Val Trp Ala Ala Ile Lys Pro Gly Ser Ser Phe Gly Ile Ser Val
                565                 570                 575

Leu Arg Ala Leu Arg Leu Leu Arg Ile Phe Lys Val Thr Lys Tyr Trp
            580                 585                 590

Ser Ser Leu Arg Asn Leu Val Val Ser Leu Leu Asn Ser Met Lys Ser
        595                 600                 605

Ile Ile Ser Leu Leu Phe Leu Leu Phe Leu Phe Ile Val Val Phe Ala
    610                 615                 620

Leu Leu Gly Met Gln Leu Phe Gly Gly Gln Phe Asn Phe Gln Asp Glu
625                 630                 635                 640

Thr Pro Thr Thr Asn Phe Asp Thr Phe Pro Ala Ala Ile Leu Thr Val
                645                 650                 655
```

```
Phe Gln Ile Leu Thr Gly Glu Asp Trp Asn Ala Val Met Tyr His Gly
            660                 665                 670

Ile Glu Ser Gln Gly Gly Val Ser Lys Gly Met Phe Ser Ser Phe Tyr
        675                 680                 685

Phe Ile Val Leu Thr Leu Phe Gly Asn Tyr Thr Leu Leu Asn Val Phe
    690                 695                 700

Leu Ala Ile Ala Val Asp Asn Leu Ala Asn Ala Gln Glu Leu Thr Lys
705                 710                 715                 720

Asp Glu Glu Glu Met Glu Glu Ala Ala Asn Gln Lys Leu Ala Leu Gln
                725                 730                 735

Lys Ala Lys Glu Val Ala Glu Val Ser Pro Met Ser Ala Ala Asn Ile
            740                 745                 750

Ser Ile Ala Ala Arg Gln Gln Asn Ser Ala Lys Ala Arg Ser Val Trp
        755                 760                 765

Glu Gln Arg Ala Ser Gln Leu Arg Leu Gln Asn Leu Arg Ala Ser Cys
    770                 775                 780

Glu Ala Leu Tyr Ser Glu Met Asp Pro Glu Glu Arg Leu Arg Phe Ala
785                 790                 795                 800

Thr Thr Arg His Leu Arg Pro Asp Met Lys Thr His Leu Asp Arg Pro
                805                 810                 815

Leu Val Val Glu Leu Gly Arg Asp Gly Ala Arg Gly Pro Val Gly Gly
            820                 825                 830

Lys Ala Arg Pro Glu Ala Ala Glu Ala Pro Glu Gly Val Asp Pro Pro
        835                 840                 845

Arg Arg His His Arg His Arg Asp Lys Asp Lys Thr Pro Ala Ala Gly
    850                 855                 860

Asp Gln Asp Arg Ala Glu Ala Pro Lys Ala Glu Ser Gly Glu Pro Gly
865                 870                 875                 880

Ala Arg Glu Glu Arg Pro Arg Pro His Arg Ser His Ser Lys Glu Ala
                885                 890                 895

Ala Gly Pro Pro Glu Ala Arg Ser Glu Arg Gly Arg Gly Pro Gly Pro
            900                 905                 910

Glu Gly Gly Arg Arg His His Arg Arg Gly Ser Pro Glu Glu Ala Ala
        915                 920                 925

Glu Arg Glu Pro Arg Arg His Arg Ala His Arg His Gln Asp Pro Ser
    930                 935                 940

Lys Glu Cys Ala Gly Ala Lys Gly Glu Arg Arg Ala Arg His Arg Gly
945                 950                 955                 960

Gly Pro Arg Ala Gly Pro Arg Glu Ala Glu Ser Gly Glu Glu Pro Ala
                965                 970                 975

Arg Arg His Arg Ala Arg His Lys Ala Gln Pro Ala His Glu Ala Val
            980                 985                 990

Glu Lys Glu Thr Thr Glu Lys Glu Ala Thr Glu Lys Glu Ala Glu Ile
        995                 1000                1005

Val Glu Ala Asp Lys Glu Lys Glu Leu Arg Asn His Gln Pro Arg Glu
    1010                1015                1020

Pro His Cys Asp Leu Glu Thr Ser Gly Thr Val Thr Val Gly Pro Met
1025                1030                1035                1040

His Thr Leu Pro Ser Thr Cys Leu Gln Lys Val Glu Glu Gln Pro Glu
                1045                1050                1055

Asp Ala Asp Asn Gln Arg Asn Val Thr Arg Met Gly Ser Gln Pro Pro
            1060                1065                1070
```

-continued

```
Asp Pro Asn Thr Ile Val His Ile Pro Val Met Leu Thr Gly Pro Leu
        1075                1080                1085

Gly Glu Ala Thr Val Val Pro Ser Gly Asn Val Asp Leu Glu Ser Gln
    1090                1095                1100

Ala Glu Gly Lys Lys Glu Val Glu Ala Asp Asp Val Met Arg Ser Gly
1105                1110                1115                1120

Pro Arg Pro Ile Val Pro Tyr Ser Ser Met Phe Cys Leu Ser Pro Thr
                1125                1130                1135

Asn Leu Leu Arg Arg Phe Cys His Tyr Ile Val Thr Met Arg Tyr Phe
            1140                1145                1150

Glu Val Val Ile Leu Val Val Ile Ala Leu Ser Ser Ile Ala Leu Ala
        1155                1160                1165

Ala Glu Asp Pro Val Arg Thr Asp Ser Pro Arg Asn Asn Ala Leu Lys
    1170                1175                1180

Tyr Leu Asp Tyr Ile Phe Thr Gly Val Phe Thr Phe Glu Met Val Ile
1185                1190                1195                1200

Lys Met Ile Asp Leu Gly Leu Leu Leu His Pro Gly Ala Tyr Phe Arg
                1205                1210                1215

Asp Leu Trp Asn Ile Leu Asp Phe Ile Val Val Ser Gly Ala Leu Val
            1220                1225                1230

Ala Phe Ala Phe Ser Gly Ser Lys Gly Lys Asp Ile Asn Thr Ile Lys
        1235                1240                1245

Ser Leu Arg Val Leu Arg Val Leu Arg Pro Leu Lys Thr Ile Lys Arg
    1250                1255                1260

Leu Pro Lys Leu Lys Ala Val Phe Asp Cys Val Val Asn Ser Leu Lys
1265                1270                1275                1280

Asn Val Leu Asn Ile Leu Ile Val Tyr Met Leu Phe Met Phe Ile Phe
                1285                1290                1295

Ala Val Ile Ala Val Gln Leu Phe Lys Gly Lys Phe Phe Tyr Cys Thr
            1300                1305                1310

Asp Glu Ser Lys Glu Leu Glu Arg Asp Cys Arg Gly Gln Tyr Leu Asp
        1315                1320                1325

Tyr Glu Lys Glu Glu Val Glu Ala Gln Pro Arg Gln Trp Lys Lys Tyr
    1330                1335                1340

Asp Phe His Tyr Asp Asn Val Leu Trp Ala Leu Leu Thr Leu Phe Thr
1345                1350                1355                1360

Val Ser Thr Gly Glu Gly Trp Pro Met Val Leu Lys His Ser Val Asp
                1365                1370                1375

Ala Thr Tyr Glu Glu Gln Gly Pro Ser Pro Gly Tyr Arg Met Glu Leu
            1380                1385                1390

Ser Ile Phe Tyr Val Val Tyr Phe Val Val Phe Pro Phe Phe Phe Val
        1395                1400                1405

Asn Ile Phe Val Ala Leu Ile Ile Ile Thr Phe Gln Glu Gln Gly Asp
    1410                1415                1420

Lys Val Met Ser Glu Cys Ser Leu Glu Lys Asn Glu Arg Ala Cys Ile
1425                1430                1435                1440

Asp Phe Ala Ile Ser Ala Lys Pro Leu Thr Arg Tyr Met Pro Gln Asn
                1445                1450                1455

Arg Gln Ser Phe Gln Tyr Lys Thr Trp Thr Phe Val Val Ser Pro Pro
            1460                1465                1470

Phe Glu Tyr Phe Ile Met Ala Met Ile Ala Leu Asn Thr Val Val Leu
        1475                1480                1485

Met Met Lys Phe Tyr Asp Ala Pro Tyr Glu Tyr Glu Leu Met Leu Lys
```

```
    1490                1495                1500

Cys Leu Asn Ile Val Phe Thr Ser Met Phe Ser Met Glu Cys Val Leu
1505                1510                1515                1520

Lys Ile Ile Ala Phe Gly Val Leu Asn Tyr Phe Arg Asp Ala Trp Asn
                1525                1530                1535

Val Phe Asp Phe Val Thr Val Leu Gly Ser Ile Thr Asp Ile Leu Val
            1540                1545                1550

Thr Glu Ile Ala Glu Thr Asn Asn Phe Ile Asn Leu Ser Phe Leu Arg
        1555                1560                1565

Leu Phe Arg Ala Ala Arg Leu Ile Lys Leu Leu Arg Gln Gly Tyr Thr
    1570                1575                1580

Ile Arg Ile Leu Leu Trp Thr Phe Val Gln Ser Phe Lys Ala Leu Pro
1585                1590                1595                1600

Tyr Val Cys Leu Leu Ile Ala Met Leu Phe Phe Ile Tyr Ala Ile Ile
                1605                1610                1615

Gly Met Gln Val Phe Gly Asn Ile Ala Leu Asp Asp Asp Thr Ser Ile
            1620                1625                1630

Asn Arg His Asn Asn Phe Arg Thr Phe Leu Gln Ala Leu Met Leu Leu
        1635                1640                1645

Phe Arg Ser Ala Thr Gly Glu Ala Trp His Glu Ile Met Leu Ser Cys
    1650                1655                1660

Leu Ser Asn Gln Ala Cys Asp Glu Gln Ala Asn Ala Thr Glu Cys Gly
1665                1670                1675                1680

Ser Asp Phe Ala Tyr Phe Tyr Phe Val Ser Phe Ile Phe Leu Cys Ser
                1685                1690                1695

Phe Leu Met Leu Asn Leu Phe Val Ala Val Ile Met Asp Asn Phe Glu
            1700                1705                1710

Tyr Leu Thr Arg Asp Ser Ser Ile Leu Gly Pro His His Leu Asp Glu
        1715                1720                1725

Phe Ile Arg Val Trp Ala Glu Tyr Asp Pro Ala Ala Cys Gly Arg Ile
    1730                1735                1740

Ser Tyr Asn Asp Met Phe Glu Met Leu Lys His Met Ser Pro Pro Leu
1745                1750                1755                1760

Gly Leu Gly Lys Lys Cys Pro Ala Arg Val Ala Tyr Lys Arg Leu Val
                1765                1770                1775

Arg Met Asn Met Pro Ile Ser Asn Glu Asp Met Thr Val His Phe Thr
            1780                1785                1790

Ser Thr Leu Met Ala Leu Ile Arg Thr Ala Leu Glu Ile Lys Leu Ala
        1795                1800                1805

Pro Ala Gly Thr Lys Gln His Gln Cys Asp Ala Glu Leu Arg Lys Glu
    1810                1815                1820

Ile Ser Val Val Trp Ala Asn Leu Pro Gln Lys Thr Leu Asp Leu Leu
1825                1830                1835                1840

Val Pro Pro His Lys Pro Asp Glu Met Thr Val Gly Lys Val Tyr Ala
                1845                1850                1855

Ala Leu Met Ile Phe Asp Phe Tyr Lys Gln Asn Lys Thr Thr Arg Asp
            1860                1865                1870

Gln Met Gln Gln Ala Pro Gly Gly Leu Ser Gln Met Gly Pro Val Ser
        1875                1880                1885

Leu Phe His Pro Leu Lys Ala Thr Leu Glu Gln Thr Gln Pro Ala Val
    1890                1895                1900

Leu Arg Gly Ala Arg Val Phe Leu Arg Gln Lys Ser Ser Thr Ser Leu
1905                1910                1915                1920
```

-continued

```
Ser Asn Gly Gly Ala Ile Gln Asn Gln Glu Ser Gly Ile Lys Glu Ser
                1925                1930                1935

Val Ser Trp Gly Thr Gln Arg Thr Gln Asp Ala Pro His Glu Ala Arg
            1940                1945                1950

Pro Pro Leu Glu Arg Gly His Ser Thr Glu Ile Pro Val Gly Arg Ser
        1955                1960                1965

Gly Ala Leu Ala Val Asp Val Gln Met Gln Ser Ile Thr Arg Arg Gly
    1970                1975                1980

Pro Asp Gly Glu Pro Gln Pro Gly Leu Glu Ser Gln Gly Arg Ala Ala
1985                1990                1995                2000

Ser Met Pro Arg Leu Ala Ala Glu Thr Gln Pro Val Thr Asp Ala Ser
                2005                2010                2015

Pro Met Lys Arg Ser Ile Ser Thr Leu Ala Gln Arg Pro Arg Gly Thr
            2020                2025                2030

His Leu Cys Ser Thr Thr Pro Asp Arg Pro Pro Pro Ser Gln Ala Ser
        2035                2040                2045

Ser His His His His His Arg Cys His Arg Arg Arg Asp Arg Lys Gln
    2050                2055                2060

Arg Ser Leu Glu Lys Gly Pro Ser Leu Ser Ala Asp Met Asp Gly Ala
2065                2070                2075                2080

Pro Ser Ser Ala Val Gly Pro Gly Leu Pro Pro Gly Glu Gly Pro Thr
                2085                2090                2095

Gly Cys Arg Arg Glu Arg Glu Arg Arg Gln Glu Arg Gly Arg Ser Gln
            2100                2105                2110

Glu Arg Arg Gln Pro Ser Ser Ser Ser Ser Glu Lys Gln Arg Phe Tyr
        2115                2120                2125

Ser Cys Asp Arg Phe Gly Gly Arg Glu Pro Pro Lys Pro Lys Pro Ser
    2130                2135                2140

Leu Ser Ser His Pro Thr Ser Pro Thr Ala Gly Gln Glu Pro Gly Pro
2145                2150                2155                2160

His Pro Gln Gly Ser Gly Ser Val Asn Gly Ser Pro Leu Leu Ser Thr
                2165                2170                2175

Ser Gly Ala Ser Thr Pro Gly Arg Gly Gly Arg Arg Gln Leu Pro Gln
            2180                2185                2190

Thr Pro Leu Thr Pro Arg Pro Ser Ile Thr Tyr Lys Thr Ala Asn Ser
        2195                2200                2205

Ser Pro Ile His Phe Ala Gly Ala Gln Thr Ser Leu Pro Ala Phe Ser
    2210                2215                2220

Pro Gly Arg Leu Ser Arg Gly Leu Ser Glu His Asn Ala Leu Leu Gln
2225                2230                2235                2240

Arg Asp Pro Leu Ser Gln Pro Leu Ala Pro Gly Ser Arg Ile Gly Ser
                2245                2250                2255

Asp Pro Tyr Leu Gly Gln Arg Leu Asp Ser Glu Ala Ser Val His Ala
            2260                2265                2270

Leu Pro Glu Asp Thr Leu Thr Phe Glu Glu Ala Val Ala Thr Asn Ser
        2275                2280                2285

Gly Arg Ser Ser Arg Thr Ser Tyr Val Ser Ser Leu Thr Ser Gln Ser
    2290                2295                2300

His Pro Leu Arg Arg Val Pro Asn Gly Tyr His Cys Thr Leu Gly Leu
2305                2310                2315                2320

Ser Ser Gly Gly Arg Ala Arg His Ser Tyr His His Pro Asp Gln Asp
                2325                2330                2335
```

```
His Trp Cys


<210> SEQ ID NO 12
<211> LENGTH: 9695
<212> TYPE: DNA
<213> ORGANISM: Rattus norvegicus
<220> FEATURE:
<221> NAME/KEY: CDS
<222> LOCATION: (92)..(7093)

<400> SEQUENCE: 12

cggcacgagc ggctaggtta ggagcccctg gcgcgccgcg ccctcggtgc cgggccgcgg      60

agccggggat gcgcgcggcg ccccgggagt c atg gtc cgc ttc ggg gac gag        112
                                   Met Val Arg Phe Gly Asp Glu
                                     1               5

cta ggc ggc cgc tat ggg ggc acc ggc ggc ggg gag cgg gct cgg ggc      160
Leu Gly Gly Arg Tyr Gly Gly Thr Gly Gly Gly Glu Arg Ala Arg Gly
         10                  15                  20

ggc ggg gcc ggc ggg gcc ggt ggc ccg ggc cag ggg ggt ctg ccg ccg      208
Gly Gly Ala Gly Gly Ala Gly Gly Pro Gly Gln Gly Gly Leu Pro Pro
     25                  30                  35

ggc cag cgg gtc ctg tac aag cag tcc att gcg caa cgc gca cgg acc      256
Gly Gln Arg Val Leu Tyr Lys Gln Ser Ile Ala Gln Arg Ala Arg Thr
 40                  45                  50                  55

atg gcc ctg tac aac ccc atc cca gtc aag cag aac tgc ttc acc gtc      304
Met Ala Leu Tyr Asn Pro Ile Pro Val Lys Gln Asn Cys Phe Thr Val
                 60                  65                  70

aac cgc tcg ctc ttc gtc ttc agc gag gac aac gtc gtc cgc aaa tat      352
Asn Arg Ser Leu Phe Val Phe Ser Glu Asp Asn Val Val Arg Lys Tyr
             75                  80                  85

gct aag cgc atc acc gaa tgg ccg ccc ttc gaa tat atg atc ctg gcc      400
Ala Lys Arg Ile Thr Glu Trp Pro Pro Phe Glu Tyr Met Ile Leu Ala
         90                  95                 100

acc atc atc gcc aac tgt att gtc ctg gcc ctg gag cag cac ctc cct      448
Thr Ile Ile Ala Asn Cys Ile Val Leu Ala Leu Glu Gln His Leu Pro
    105                 110                 115

gat ggg gac aag act ccc atg tct gaa cga ctg gat gac acg gaa cct      496
Asp Gly Asp Lys Thr Pro Met Ser Glu Arg Leu Asp Asp Thr Glu Pro
120                 125                 130                 135

tac ttc atc ggc atc ttt tgc ttc gag gcg ggc atc aag atc ata gct      544
Tyr Phe Ile Gly Ile Phe Cys Phe Glu Ala Gly Ile Lys Ile Ile Ala
                140                 145                 150

ctg ggc ttc gtg ttc cac aaa ggc tcc tac ctc cgg aat ggc tgg aac      592
Leu Gly Phe Val Phe His Lys Gly Ser Tyr Leu Arg Asn Gly Trp Asn
            155                 160                 165

gtc atg gac ttc gtg gtg gtc ctc aca ggg att ctt gcc aca gct gga      640
Val Met Asp Phe Val Val Val Leu Thr Gly Ile Leu Ala Thr Ala Gly
        170                 175                 180

act gac ttt gat ctg cgc acc ctg agg gct gtg cgt gtg ctt agg ccc      688
Thr Asp Phe Asp Leu Arg Thr Leu Arg Ala Val Arg Val Leu Arg Pro
    185                 190                 195

ctg aag ttg gtg tct gga att cca agc ttg cag gtg gtg ctc aag tcc      736
Leu Lys Leu Val Ser Gly Ile Pro Ser Leu Gln Val Val Leu Lys Ser
200                 205                 210                 215

atc atg aag gcc atg gtc ccg ctg ctg cag atc ggg ctg ctg ctc ttc      784
Ile Met Lys Ala Met Val Pro Leu Leu Gln Ile Gly Leu Leu Leu Phe
                220                 225                 230

ttc gcc atc ctc atg ttc gct atc atc ggc ctc gag ttc tat atg ggc      832
Phe Ala Ile Leu Met Phe Ala Ile Ile Gly Leu Glu Phe Tyr Met Gly
            235                 240                 245
```

-continued

```
aaa ttc cat aag gcc tgc ttc ccc aac agc aca gat gca gag cct gtg      880
Lys Phe His Lys Ala Cys Phe Pro Asn Ser Thr Asp Ala Glu Pro Val
        250                 255                 260

ggt gac ttt cct tgt ggc aag gag gcc cct gct cgt ctg tgt gac agt      928
Gly Asp Phe Pro Cys Gly Lys Glu Ala Pro Ala Arg Leu Cys Asp Ser
    265                 270                 275

gac acc gaa tgc cgg gag tac tgg cca gga ccc aac ttt ggc atc acc      976
Asp Thr Glu Cys Arg Glu Tyr Trp Pro Gly Pro Asn Phe Gly Ile Thr
280                 285                 290                 295

aat ttt gac aac atc ctg ttt gcc atc ttg acc gtg ttc cag tgt atc     1024
Asn Phe Asp Asn Ile Leu Phe Ala Ile Leu Thr Val Phe Gln Cys Ile
                300                 305                 310

acc atg gag ggc tgg act gac atc ctc tac aat aca aat gat gcg gcc     1072
Thr Met Glu Gly Trp Thr Asp Ile Leu Tyr Asn Thr Asn Asp Ala Ala
            315                 320                 325

ggc aac acg tgg aac tgg ttg tac ttc atc ccc ctc atc atc att ggc     1120
Gly Asn Thr Trp Asn Trp Leu Tyr Phe Ile Pro Leu Ile Ile Ile Gly
        330                 335                 340

tcc ttc ttc atg ctc aac ctg gtg ctc ggt gtg ctt tca gga gag ttt     1168
Ser Phe Phe Met Leu Asn Leu Val Leu Gly Val Leu Ser Gly Glu Phe
    345                 350                 355

gcc aaa gag cgg gag cga gtc gag aac cgc cgt gcc ttc ctg aag ctc     1216
Ala Lys Glu Arg Glu Arg Val Glu Asn Arg Arg Ala Phe Leu Lys Leu
360                 365                 370                 375

cgc agg cag cag cag att gag cga gaa ctg aat ggg tac ttg gag tgg     1264
Arg Arg Gln Gln Gln Ile Glu Arg Glu Leu Asn Gly Tyr Leu Glu Trp
                380                 385                 390

atc ttc aag gcg gag gaa gtc atg ttg gca gag gag gac aag aac gca     1312
Ile Phe Lys Ala Glu Glu Val Met Leu Ala Glu Glu Asp Lys Asn Ala
            395                 400                 405

gaa gag aag tcc cct ttg gat gtg ttg aag aga gct gct acc aag aag     1360
Glu Glu Lys Ser Pro Leu Asp Val Leu Lys Arg Ala Ala Thr Lys Lys
        410                 415                 420

agc cga aat gac ctc atc cat gca gaa gag ggg gag gac cgg ttt gta     1408
Ser Arg Asn Asp Leu Ile His Ala Glu Glu Gly Glu Asp Arg Phe Val
    425                 430                 435

gac ctc tgt gct gct ggg tct ccc ttt gct cgt gcc agc ctc aag agt     1456
Asp Leu Cys Ala Ala Gly Ser Pro Phe Ala Arg Ala Ser Leu Lys Ser
440                 445                 450                 455

ggg aag aca gag agc tca tcg tac ttc cgg agg aag gag aag atg ttc     1504
Gly Lys Thr Glu Ser Ser Ser Tyr Phe Arg Arg Lys Glu Lys Met Phe
                460                 465                 470

cgg ttc ctt atc cgt cgt atg gtg aaa gca cag agc ttc tac tgg gtg     1552
Arg Phe Leu Ile Arg Arg Met Val Lys Ala Gln Ser Phe Tyr Trp Val
            475                 480                 485

gta ctg tgc gtg gtg gcc ctg aac acg ttg tgt gtg gcc atg gta cac     1600
Val Leu Cys Val Val Ala Leu Asn Thr Leu Cys Val Ala Met Val His
        490                 495                 500

tat aat cag cct cag cgg ctt acc act gca ctg tac ttt gca gag ttt     1648
Tyr Asn Gln Pro Gln Arg Leu Thr Thr Ala Leu Tyr Phe Ala Glu Phe
    505                 510                 515

gtt ttc ctg ggt ctc ttc ctc aca gag atg tcc ctg aag atg tac ggt     1696
Val Phe Leu Gly Leu Phe Leu Thr Glu Met Ser Leu Lys Met Tyr Gly
520                 525                 530                 535

cta ggg ccc aga agc tac ttc cgg tct tcc ttc aac tgc ttt gac ttt     1744
Leu Gly Pro Arg Ser Tyr Phe Arg Ser Ser Phe Asn Cys Phe Asp Phe
                540                 545                 550

ggg gtg att gtg ggg agt atc ttt gaa gta gtc tgg gct gcc atc aag     1792
Gly Val Ile Val Gly Ser Ile Phe Glu Val Val Trp Ala Ala Ile Lys
            555                 560                 565
```

-continued

```
cca gga acc tcc ttc gga atc agt gtg ctg cgg gct ctc cga ctg ctg      1840
Pro Gly Thr Ser Phe Gly Ile Ser Val Leu Arg Ala Leu Arg Leu Leu
        570                 575                 580

agg att ttc aaa gtc acc aag tat tgg aac tcc ctg agg aac ctg gtt      1888
Arg Ile Phe Lys Val Thr Lys Tyr Trp Asn Ser Leu Arg Asn Leu Val
    585                 590                 595

gtt tcc ctc ctc aac tcc atg aag tcc atc atc agc ctt ctc ttc ctg      1936
Val Ser Leu Leu Asn Ser Met Lys Ser Ile Ile Ser Leu Leu Phe Leu
600                 605                 610                 615

ctt ttc ctt ttc att gtg gtc ttc gct ctg ttg ggg atg cag ctg ttt      1984
Leu Phe Leu Phe Ile Val Val Phe Ala Leu Leu Gly Met Gln Leu Phe
                620                 625                 630

ggg gga cag ttc aac ttt caa gat gag act cca acc acc aat ttt gat      2032
Gly Gly Gln Phe Asn Phe Gln Asp Glu Thr Pro Thr Thr Asn Phe Asp
            635                 640                 645

acc ttc cca gct gcc atc ctc act gtg ttt cag att ctg aca gga gag      2080
Thr Phe Pro Ala Ala Ile Leu Thr Val Phe Gln Ile Leu Thr Gly Glu
        650                 655                 660

gac tgg aat gca gtc atg tat cat ggg att gag tca caa gga gga gtc      2128
Asp Trp Asn Ala Val Met Tyr His Gly Ile Glu Ser Gln Gly Gly Val
    665                 670                 675

agc aaa ggc atg ttt tca tcc ttt tac ttc atc gtc ctg aca ctg ttt      2176
Ser Lys Gly Met Phe Ser Ser Phe Tyr Phe Ile Val Leu Thr Leu Phe
680                 685                 690                 695

gga aac tac acc ctg ttg aac gtt ttc ttg gcc att gct gtg gac aac      2224
Gly Asn Tyr Thr Leu Leu Asn Val Phe Leu Ala Ile Ala Val Asp Asn
                700                 705                 710

ctt gcc aat gcc cag gag ttg acc aag gat gaa gag gag atg gaa gag      2272
Leu Ala Asn Ala Gln Glu Leu Thr Lys Asp Glu Glu Glu Met Glu Glu
            715                 720                 725

gca gcc aat cag aag ctt gct ctt cag aag gcc aaa gaa gta gct gaa      2320
Ala Ala Asn Gln Lys Leu Ala Leu Gln Lys Ala Lys Glu Val Ala Glu
        730                 735                 740

gtc agc ccc atg tct gct gcc aac atc tcc att gct gcc agg cag cag      2368
Val Ser Pro Met Ser Ala Ala Asn Ile Ser Ile Ala Ala Arg Gln Gln
    745                 750                 755

aac tcg gcc aag gcg cgc tca gta tgg gag cag cgg gcc agt cag cta      2416
Asn Ser Ala Lys Ala Arg Ser Val Trp Glu Gln Arg Ala Ser Gln Leu
760                 765                 770                 775

agg ctc cag aac ctg cgt gcc agc tgt gag gca ctg tac agt gag atg      2464
Arg Leu Gln Asn Leu Arg Ala Ser Cys Glu Ala Leu Tyr Ser Glu Met
                780                 785                 790

gac ccg gag gag cgc ctg cgt tat gcc agc acg cgc cac gtg agg cca      2512
Asp Pro Glu Glu Arg Leu Arg Tyr Ala Ser Thr Arg His Val Arg Pro
            795                 800                 805

gac atg aag aca cac atg gac cga ccc cta gtg gtg gaa cct ggt cgg      2560
Asp Met Lys Thr His Met Asp Arg Pro Leu Val Val Glu Pro Gly Arg
        810                 815                 820

gat ggc ctg cgg gga ccc gcc ggg aac aag tca aag cct gag ggc acg      2608
Asp Gly Leu Arg Gly Pro Ala Gly Asn Lys Ser Lys Pro Glu Gly Thr
    825                 830                 835

gag gcc acc gaa ggt gcg gat cca cca cgc cga cac cac cgg cat cgt      2656
Glu Ala Thr Glu Gly Ala Asp Pro Pro Arg Arg His His Arg His Arg
840                 845                 850                 855

gat agg gac aag acc tca gcc tca acc cct gct gga ggc gaa cag gac      2704
Asp Arg Asp Lys Thr Ser Ala Ser Thr Pro Ala Gly Gly Glu Gln Asp
                860                 865                 870

agg aca gac tgc cca aag gcc gaa agc acc gag acc ggg gcc cgg gag      2752
Arg Thr Asp Cys Pro Lys Ala Glu Ser Thr Glu Thr Gly Ala Arg Glu
```

-continued

```
            875                 880                 885

gaa cgt gcg cgc cct cgt cga agt cac agc aag gag gct cca ggg gct     2800
Glu Arg Ala Arg Pro Arg Arg Ser His Ser Lys Glu Ala Pro Gly Ala
        890                 895                 900

gac aca caa gtg cgt tgt gag cgc agt aga cgt cac cac cgg cgc gga     2848
Asp Thr Gln Val Arg Cys Glu Arg Ser Arg Arg His His Arg Arg Gly
    905                 910                 915

tcc ccg gag gag gcc act gaa cgg gaa cct cgg cgc cac cgt gcc cac     2896
Ser Pro Glu Glu Ala Thr Glu Arg Glu Pro Arg Arg His Arg Ala His
920                 925                 930                 935

cgg cac gca cag gac tca agc aag gaa ggc aag gag ggc act gca ccg     2944
Arg His Ala Gln Asp Ser Ser Lys Glu Gly Lys Glu Gly Thr Ala Pro
                940                 945                 950

gtg ctt gta ccc aag ggc gag cgt cgc gca aga cat cga ggc ccg cgt     2992
Val Leu Val Pro Lys Gly Glu Arg Arg Ala Arg His Arg Gly Pro Arg
            955                 960                 965

acg ggc ccc cgt gag aca gag aac agt gag gag ccc aca cgc agg cac     3040
Thr Gly Pro Arg Glu Thr Glu Asn Ser Glu Glu Pro Thr Arg Arg His
        970                 975                 980

cgt gca aag cat aag gtg cca cca aca ctt gag ccc cca gag agg gag     3088
Arg Ala Lys His Lys Val Pro Pro Thr Leu Glu Pro Pro Glu Arg Glu
    985                 990                 995

gtt gca gag aag gag agc aac gtg gtg gaa ggg gat aag gaa act cga     3136
Val Ala Glu Lys Glu Ser Asn Val Val Glu Gly Asp Lys Glu Thr Arg
1000                1005                1010                1015

aat cac cag ccc aag gaa cct cgc tgt gac ctg gag gcc att gcg gtt     3184
Asn His Gln Pro Lys Glu Pro Arg Cys Asp Leu Glu Ala Ile Ala Val
                1020                1025                1030

aca ggc gtg ggc tct ctg cac atg ctg ccc agc acc tgt ctc cag aaa     3232
Thr Gly Val Gly Ser Leu His Met Leu Pro Ser Thr Cys Leu Gln Lys
            1035                1040                1045

gtg gac gaa cag cca gag gat gca gac aac cag cgt aat gtc acc cgg     3280
Val Asp Glu Gln Pro Glu Asp Ala Asp Asn Gln Arg Asn Val Thr Arg
        1050                1055                1060

atg ggc agt cag ccc tca gac ccc agc acc act gtg cat gtc cca gtg     3328
Met Gly Ser Gln Pro Ser Asp Pro Ser Thr Thr Val His Val Pro Val
    1065                1070                1075

aca ctg aca ggc cct ccc ggg gag gcc act gta gtt ccc agt gct aac     3376
Thr Leu Thr Gly Pro Pro Gly Glu Ala Thr Val Val Pro Ser Ala Asn
1080                1085                1090                1095

acg gac ctg gaa ggc caa gcg gag ggc aag aag gag gca gag gct gac     3424
Thr Asp Leu Glu Gly Gln Ala Glu Gly Lys Lys Glu Ala Glu Ala Asp
                1100                1105                1110

gat gtg ctg aga aga ggc ccc agg ccc atc gtt ccc tac agt tcc atg     3472
Asp Val Leu Arg Arg Gly Pro Arg Pro Ile Val Pro Tyr Ser Ser Met
            1115                1120                1125

ttc tgc ctc agc ccc acc aac cta ctc cgt cgc ttc tgc cat tac att     3520
Phe Cys Leu Ser Pro Thr Asn Leu Leu Arg Arg Phe Cys His Tyr Ile
        1130                1135                1140

gtg acc atg cgg tac ttt gag atg gtg att ctt gtg gtc atc gcc ttg     3568
Val Thr Met Arg Tyr Phe Glu Met Val Ile Leu Val Val Ile Ala Leu
    1145                1150                1155

agc agc att gcc ctg gct gct gag gat ccc gtg cgg acc gac tca ttc     3616
Ser Ser Ile Ala Leu Ala Ala Glu Asp Pro Val Arg Thr Asp Ser Phe
1160                1165                1170                1175

cgg aac aat gct ctg aag tac atg gac tac atc ttt aca gga gtc ttc     3664
Arg Asn Asn Ala Leu Lys Tyr Met Asp Tyr Ile Phe Thr Gly Val Phe
                1180                1185                1190

acc ttt gag atg gtc ata aag atg ata gac ttg ggc ctg ctg ctg cac     3712
```

-continued

```
Thr Phe Glu Met Val Ile Lys Met Ile Asp Leu Gly Leu Leu Leu His
            1195                1200                1205

cct ggg gcc tac ttc cgg gac ctg tgg aac att ctg gac ttc att gtt      3760
Pro Gly Ala Tyr Phe Arg Asp Leu Trp Asn Ile Leu Asp Phe Ile Val
        1210                1215                1220

gtc agt gga gcc ctg gtg gca ttt gca ttc tca gga tcc aaa ggg aaa      3808
Val Ser Gly Ala Leu Val Ala Phe Ala Phe Ser Gly Ser Lys Gly Lys
    1225                1230                1235

gac atc aat acc atc aag tct ctg aga gtc ctg cga gtc ctg cgg ccc      3856
Asp Ile Asn Thr Ile Lys Ser Leu Arg Val Leu Arg Val Leu Arg Pro
1240                1245                1250                1255

ctc aag acc atc aag cgg ctg cct aaa ctc aag gct gtg ttt gac tgt      3904
Leu Lys Thr Ile Lys Arg Leu Pro Lys Leu Lys Ala Val Phe Asp Cys
                1260                1265                1270

gtg gtg aac tct ctg aag aat gtc ttg aac atc ctg atc gtc tac atg      3952
Val Val Asn Ser Leu Lys Asn Val Leu Asn Ile Leu Ile Val Tyr Met
            1275                1280                1285

ctc ttc atg ttt ata ttt gcc gtc atc gcc gtc caa ctc ttc aaa ggg      4000
Leu Phe Met Phe Ile Phe Ala Val Ile Ala Val Gln Leu Phe Lys Gly
        1290                1295                1300

aag ttc ttt tac tgc act gat gag tcc aag gag ctg gag cgg gac tgc      4048
Lys Phe Phe Tyr Cys Thr Asp Glu Ser Lys Glu Leu Glu Arg Asp Cys
    1305                1310                1315

agg ggt cag tat ttg gat tat gag aag gaa gag gta gaa gcc cag cca      4096
Arg Gly Gln Tyr Leu Asp Tyr Glu Lys Glu Glu Val Glu Ala Gln Pro
1320                1325                1330                1335

agg cag tgg aag aaa tat gac ttc cac tat gac aat gtg ctc tgg gcc      4144
Arg Gln Trp Lys Lys Tyr Asp Phe His Tyr Asp Asn Val Leu Trp Ala
                1340                1345                1350

ttg ctg act ctg ttt acg gtg tcc aca gga gag ggg tgg ccc atg gtg      4192
Leu Leu Thr Leu Phe Thr Val Ser Thr Gly Glu Gly Trp Pro Met Val
            1355                1360                1365

ctg aaa cac tct gtg gac gcc acc tat gag gag cag ggg cca agc ccc      4240
Leu Lys His Ser Val Asp Ala Thr Tyr Glu Glu Gln Gly Pro Ser Pro
        1370                1375                1380

ggg ttt cgg atg gag ctt tcc atc ttc tat gtg gtc tac ttt gtg gtc      4288
Gly Phe Arg Met Glu Leu Ser Ile Phe Tyr Val Val Tyr Phe Val Val
    1385                1390                1395

ttc cct ttt ttc ttt gtc aac atc ttt gtg gcc ttg atc atc atc acc      4336
Phe Pro Phe Phe Phe Val Asn Ile Phe Val Ala Leu Ile Ile Ile Thr
1400                1405                1410                1415

ttc cag gag cag ggg gac aag gtg atg tct gag tgc agt ctg gaa aag      4384
Phe Gln Glu Gln Gly Asp Lys Val Met Ser Glu Cys Ser Leu Glu Lys
                1420                1425                1430

aat gag agg gct tgc att gac ttt gcc atc agc gcc aaa ccc ctg aca      4432
Asn Glu Arg Ala Cys Ile Asp Phe Ala Ile Ser Ala Lys Pro Leu Thr
            1435                1440                1445

cgg tac atg cct cag aac aag cag tcg ttc cag tat aag aca tgg aca      4480
Arg Tyr Met Pro Gln Asn Lys Gln Ser Phe Gln Tyr Lys Thr Trp Thr
        1450                1455                1460

ttt gtg gtc tct cca ccc ttt gag tac ttc att atg gcc atg ata gcc      4528
Phe Val Val Ser Pro Pro Phe Glu Tyr Phe Ile Met Ala Met Ile Ala
    1465                1470                1475

ctc aac aca gtg gtg ctg atg atg aag ttc tac gat gcc cct tat gag      4576
Leu Asn Thr Val Val Leu Met Met Lys Phe Tyr Asp Ala Pro Tyr Glu
1480                1485                1490                1495

tac gag ctg atg ctg aag tgc ttg aac atc gtc ttc aca tcc atg ttc      4624
Tyr Glu Leu Met Leu Lys Cys Leu Asn Ile Val Phe Thr Ser Met Phe
                1500                1505                1510
```

-continued

```
tct ctg gag tgc atc ctg aag atc atc gcc ttc ggg gtg ttg aac tac     4672
Ser Leu Glu Cys Ile Leu Lys Ile Ile Ala Phe Gly Val Leu Asn Tyr
            1515                1520                1525

ttc aga gat gcc tgg aac gtc ttt gac ttt gtc act gtt ttg gga agt     4720
Phe Arg Asp Ala Trp Asn Val Phe Asp Phe Val Thr Val Leu Gly Ser
        1530                1535                1540

att act gat att tta gta acg gag att gcg gaa acg aac aac ttc atc     4768
Ile Thr Asp Ile Leu Val Thr Glu Ile Ala Glu Thr Asn Asn Phe Ile
    1545                1550                1555

aac ttg agc ttc ctt cgc ctc ttc cgg gca gca cgg ctg atc aag ctg     4816
Asn Leu Ser Phe Leu Arg Leu Phe Arg Ala Ala Arg Leu Ile Lys Leu
1560                1565                1570                1575

ctt cgc cag ggc tac acc atc cgc atc ttg tta tgg acc ttt gtc cag     4864
Leu Arg Gln Gly Tyr Thr Ile Arg Ile Leu Leu Trp Thr Phe Val Gln
                1580                1585                1590

tcc ttt aag gcg ctg ccc tac gtg tgc ctc ctc att gcc atg ctg ttc     4912
Ser Phe Lys Ala Leu Pro Tyr Val Cys Leu Leu Ile Ala Met Leu Phe
            1595                1600                1605

ttc atc tac gcc atc atc ggc atg cag gtt ttt gga aac att gcc ctt     4960
Phe Ile Tyr Ala Ile Ile Gly Met Gln Val Phe Gly Asn Ile Ala Leu
        1610                1615                1620

gat gat ggc acc agc atc aac cga cac aac aac ttc cgg aca ttt ctg     5008
Asp Asp Gly Thr Ser Ile Asn Arg His Asn Asn Phe Arg Thr Phe Leu
    1625                1630                1635

caa gcc tta atg ctg ttg ttc agg agt gcc act ggg gag gcc tgg cac     5056
Gln Ala Leu Met Leu Leu Phe Arg Ser Ala Thr Gly Glu Ala Trp His
1640                1645                1650                1655

gaa atc atg ctg tct tgc ctg ggc aac cgg gcc tgc gac cca cat gcc     5104
Glu Ile Met Leu Ser Cys Leu Gly Asn Arg Ala Cys Asp Pro His Ala
                1660                1665                1670

aac gcc agc gaa tgc ggg agc gac ttt gcc tat ttt tat ttt gtc tcc     5152
Asn Ala Ser Glu Cys Gly Ser Asp Phe Ala Tyr Phe Tyr Phe Val Ser
            1675                1680                1685

ttc atc ttc ctc tgt tcc ttt ctg atg ctg aac ctc ttt gtt gct gtg     5200
Phe Ile Phe Leu Cys Ser Phe Leu Met Leu Asn Leu Phe Val Ala Val
        1690                1695                1700

atc atg gac aat ttc gaa tac ctc acg cgg gat tct tcc atc cta ggg     5248
Ile Met Asp Asn Phe Glu Tyr Leu Thr Arg Asp Ser Ser Ile Leu Gly
    1705                1710                1715

ccg cac cac ctc gat gaa ttc att cgc gtc tgg gct gaa tac gac cca     5296
Pro His His Leu Asp Glu Phe Ile Arg Val Trp Ala Glu Tyr Asp Pro
1720                1725                1730                1735

gct gcg tgt ggg cgc atc agt tac aat gac atg ttt gag atg ctg aaa     5344
Ala Ala Cys Gly Arg Ile Ser Tyr Asn Asp Met Phe Glu Met Leu Lys
                1740                1745                1750

cac atg tcc cca cct ctg ggt ttg ggg aag aaa tgc ccg gct cga gtt     5392
His Met Ser Pro Pro Leu Gly Leu Gly Lys Lys Cys Pro Ala Arg Val
            1755                1760                1765

gca tac aag cgc ctg gtt cga atg aac atg ccc ata tcc aat gag gac     5440
Ala Tyr Lys Arg Leu Val Arg Met Asn Met Pro Ile Ser Asn Glu Asp
        1770                1775                1780

atg acg gta cac ttt aca tcc aca ctg atg gcc ctc atc cgg acg gca     5488
Met Thr Val His Phe Thr Ser Thr Leu Met Ala Leu Ile Arg Thr Ala
    1785                1790                1795

ctg gag atc aag ctt gcc cca gcg ggg aca aaa cag cac caa tgt gat     5536
Leu Glu Ile Lys Leu Ala Pro Ala Gly Thr Lys Gln His Gln Cys Asp
1800                1805                1810                1815

gct gag ctg agg aag gag atc tct tct gtg tgg gct aat ctg ccc cag     5584
Ala Glu Leu Arg Lys Glu Ile Ser Ser Val Trp Ala Asn Leu Pro Gln
                1820                1825                1830
```

-continued

```
aag act ctg gac tta ctg gtg cca ccc cac aaa cct gac gag atg aca     5632
Lys Thr Leu Asp Leu Leu Val Pro Pro His Lys Pro Asp Glu Met Thr
            1835                1840                1845

gtg ggg aag gtc tat gcg gct ctc atg ata ttt gac ttc tac aaa cag     5680
Val Gly Lys Val Tyr Ala Ala Leu Met Ile Phe Asp Phe Tyr Lys Gln
        1850                1855                1860

aac aaa acc acc aga gat cag act cac caa gct cct gga ggc ctg tcc     5728
Asn Lys Thr Thr Arg Asp Gln Thr His Gln Ala Pro Gly Gly Leu Ser
    1865                1870                1875

cag atg ggt cct gtt tcc ctg ttc cat cct ctg aag gcc acc ctg gag     5776
Gln Met Gly Pro Val Ser Leu Phe His Pro Leu Lys Ala Thr Leu Glu
1880                1885                1890                1895

cag aca cag ccc gct gtg ctc cga gga gct cgg gtt ttc ctt cga caa     5824
Gln Thr Gln Pro Ala Val Leu Arg Gly Ala Arg Val Phe Leu Arg Gln
                1900                1905                1910

aag agt gca act tcc ctc agc aat ggg ggc gcc ata caa acc cag gaa     5872
Lys Ser Ala Thr Ser Leu Ser Asn Gly Gly Ala Ile Gln Thr Gln Glu
            1915                1920                1925

agt ggc atc aag gag tcc ctg tcc tgg ggc acg cag agg acc cag gac     5920
Ser Gly Ile Lys Glu Ser Leu Ser Trp Gly Thr Gln Arg Thr Gln Asp
        1930                1935                1940

gta ctt tat gag gcc aga gca cct cta gaa cgt ggc cat tct gca gag     5968
Val Leu Tyr Glu Ala Arg Ala Pro Leu Glu Arg Gly His Ser Ala Glu
    1945                1950                1955

atc cct gtg ggg cag cca gga gca ctg gct gta gat gtc cag atg cag     6016
Ile Pro Val Gly Gln Pro Gly Ala Leu Ala Val Asp Val Gln Met Gln
1960                1965                1970                1975

aac atg aca ttg aga gga ccg gat ggg gag ccc cag cct ggc ctg gag     6064
Asn Met Thr Leu Arg Gly Pro Asp Gly Glu Pro Gln Pro Gly Leu Glu
                1980                1985                1990

agc caa ggc cga gcg gcc tct atg cca cgc ctg gcg gca gaa aca cag     6112
Ser Gln Gly Arg Ala Ala Ser Met Pro Arg Leu Ala Ala Glu Thr Gln
            1995                2000                2005

ccg gcc cct aat gcc agc ccc atg aag cgc tcc atc tcc aca ctg gct     6160
Pro Ala Pro Asn Ala Ser Pro Met Lys Arg Ser Ile Ser Thr Leu Ala
        2010                2015                2020

cca cgc ccg cat ggg act cag ctt tgc aac aca gtc ctg gac cgg cca     6208
Pro Arg Pro His Gly Thr Gln Leu Cys Asn Thr Val Leu Asp Arg Pro
    2025                2030                2035

cct cct agc cag gtg tcc cat cac cac cac cac cgc tgc cac cgg cgc     6256
Pro Pro Ser Gln Val Ser His His His His His Arg Cys His Arg Arg
2040                2045                2050                2055

agg gac aag aag cag agg tcc ctg gaa aag ggg ccc agc ctg tct gtt     6304
Arg Asp Lys Lys Gln Arg Ser Leu Glu Lys Gly Pro Ser Leu Ser Val
                2060                2065                2070

gac aca gaa ggt gca cca agt act gct gca gga tct ggc ctg ccc cat     6352
Asp Thr Glu Gly Ala Pro Ser Thr Ala Ala Gly Ser Gly Leu Pro His
            2075                2080                2085

gga gaa ggg tcc aca ggc tgc cgg cgg gag cgt aag caa gag cga ggc     6400
Gly Glu Gly Ser Thr Gly Cys Arg Arg Glu Arg Lys Gln Glu Arg Gly
        2090                2095                2100

cgg tcc cag gag cgg agg cag ccc tcc tcc tct tct tca gag aag cag     6448
Arg Ser Gln Glu Arg Arg Gln Pro Ser Ser Ser Ser Ser Glu Lys Gln
    2105                2110                2115

cgc ttc tat tcc tgt gac cgc ttt ggg agc cgg gag ccc cca caa cct     6496
Arg Phe Tyr Ser Cys Asp Arg Phe Gly Ser Arg Glu Pro Pro Gln Pro
2120                2125                2130                2135

aag ccc tcc ctc agt agc cac ccc ata tcg cca aca gcg gca cta gag     6544
Lys Pro Ser Leu Ser Ser His Pro Ile Ser Pro Thr Ala Ala Leu Glu
```

-continued

```
                2140                2145                2150

cca gga ccc cac ccg cag ggc agt ggt tcc gtt aat ggg agc ccc ttg      6592
Pro Gly Pro His Pro Gln Gly Ser Gly Ser Val Asn Gly Ser Pro Leu
            2155                2160                2165

atg tca aca tct ggt gct agc acg ccg ggc cga ggt ggg cgg agg cag      6640
Met Ser Thr Ser Gly Ala Ser Thr Pro Gly Arg Gly Gly Arg Arg Gln
        2170                2175                2180

ctc ccc cag act ccc ctg acc cca cgc ccc agc atc acc tac aag acg      6688
Leu Pro Gln Thr Pro Leu Thr Pro Arg Pro Ser Ile Thr Tyr Lys Thr
    2185                2190                2195

gcc aat tcc tcg cct gtc cac ttt gct gag ggt cag agt ggc ctt cca      6736
Ala Asn Ser Ser Pro Val His Phe Ala Glu Gly Gln Ser Gly Leu Pro
2200                2205                2210                2215

gcc ttc tcc cct ggc cgt ctc agc cgc ggc ctt tct gaa cac aat gcc      6784
Ala Phe Ser Pro Gly Arg Leu Ser Arg Gly Leu Ser Glu His Asn Ala
                2220                2225                2230

ctg ctc cag aaa gag ccc ctg agc cag cct cta gct tct ggc tcc cgc      6832
Leu Leu Gln Lys Glu Pro Leu Ser Gln Pro Leu Ala Ser Gly Ser Arg
            2235                2240                2245

att ggc tct gac cct tac cta ggg cag cgt ctg gac agt gag gcc tct      6880
Ile Gly Ser Asp Pro Tyr Leu Gly Gln Arg Leu Asp Ser Glu Ala Ser
        2250                2255                2260

gcc cac aac ctg cct gag gat aca ctc acc ttt gaa gag gcc gtg gcc      6928
Ala His Asn Leu Pro Glu Asp Thr Leu Thr Phe Glu Glu Ala Val Ala
    2265                2270                2275

acc aac tct ggc cgc tcc tcc agg act tcc tat gtg tcc tcc ctc act      6976
Thr Asn Ser Gly Arg Ser Ser Arg Thr Ser Tyr Val Ser Ser Leu Thr
2280                2285                2290                2295

tcc caa tcc cac cct ctc cgc cgt gta ccc aat ggc tac cac tgc act      7024
Ser Gln Ser His Pro Leu Arg Arg Val Pro Asn Gly Tyr His Cys Thr
                2300                2305                2310

ttg gga ctc agc acc ggc gtc cgg gcg cgg cac agc tac cac cac cca      7072
Leu Gly Leu Ser Thr Gly Val Arg Ala Arg His Ser Tyr His His Pro
            2315                2320                2325

gac cag gat cac tgg tgc tag ctgcaccacg accacccatg caccagctcg         7123
Asp Gln Asp His Trp Cys
        2330

tgggtgcggg ttccagttga tgagttttat catccgctct gggttgtgcg gtcacagccc    7183

tgggaggagg gtcctcacat cgcggcctct gtggtggagg ttcctgcttc tctccctccc    7243

tcccttttac actggacaga ctaataaagc cctttcttag agggatatgg tcctctctat    7303

cctcctgtgt actgccttcc tgggttccat gccagatgtt ggatcctaag cagaggtagc    7363

tgagttgaga tagacccagc aaatccaaat cctatgtcat ggcctccagc ttccagggtg    7423

ggtacttggg actttcttag gaggtctgag cctcatggag attgtggttt gtccaaatgt    7483

gtggcatggg ggatagggta ccctcaaagg caaggaaagg agcccaactg tgtggcctgg    7543

cagcacctgc cagcatcact actctcatgt ctattgtggt cttggagtca aacagcacat    7603

gtatatagag atatgctcaa gggcctgcct ttcacctaca ttgtcaccat aatagggacc    7663

aaatctagag gatgtccttg ctgttgattc tggttttcag tcacaacact ttcacttttt    7723

gtcatttcta tatagttgat ctagaaaaac agaaatcaaa acagggaaga aaatgttcgt    7783

gtaacttaaa aaagaaatca acgtgtagga aggtctccat tttgcattgt ttctgtgact    7843

tgtatgcaat gttcctgtat gtattctacc cttcccggga agtccccaat gaccctggtt    7903

cctctgctca accaagtgcc tgatctctgg ctctgagcat cgtggctgag gtgcggcctc    7963

aggaagcatc ggggagctgc tcagagcagc actaggactt gtgtcttagg gacactgacc    8023
```

```
gtgtccagca gcatgtcaga gaagcagctg tagtgcccat gttcctccct gagtgatggg   8083

ttctgaagaa gccagagcag cacaatgtgt gcttgcgtga ggcactttcc gccttttaaa   8143

atctgattct cagggatggg atgcctgcca agtagggtgt gatctctgtt gtgttttaaa   8203

aaacaacaac aacaaacaaa caaaacctag tattcactga atgctgaaga gagcaaaatg   8263

caagcaaaga agggactggg gttagaggga gaagcccgca ctggcagcat aataagaaac   8323

tggcagggag gggatggtcc tggaacaggc caggtgccta gagctgagtc cagcccctgg   8383

cccggaactg gggacacagc actcaaataa aacctcatgg ctacttggtg aaaggcaaac   8443

ccatgctcag gaaggtgttc agtgtgcaga gatggctgtg aggccatgag agaaaggttt   8503

cacataggca ggcagtcctt ggtgtgttct ctgtgttttg aaacgtctga tgacttcttg   8563

gtggactgtt ggtttctacc ccatgtttct cacagaagct gtgtatatgt gtgattgcgc   8623

gtgtgattgc atgtgtgtgg tagtgtgcgt gcgtgagcat gcatgagtca taggaaatgt   8683

gtgtgtgtgt gtgtgtgtgt gtgtaggtgt gtgtacgtgt gttcagcaag tggcttttgt   8743

caaccatagg gctatgcaac aaaagacaca ttactagaaa caaaacacaa gaccaccact   8803

cggtctaggg tttcagcatg attgtgacca aacctttat agaatttcct tatatgaagg   8863

cacaataccc tgaaacttta aagataacag agtattttat tccagtaggg taagattaaa   8923

caggaccctg gactgcatgt gactgcactc atgtacaaca gaggaggatg tgcattttga   8983

tactgttctg tctctgtccc agccccagcc cttttctctt gagtgttgaa tgtatacatt   9043

ctgtgtggaa ctacagctgc tccagacagt cctgggttgg gaatcatctt tatcccacat   9103

taacatagct ggcttttctt ccaagcactg gtacacagga aaggagacat gatgtcttgc   9163

ttcctgactt tgggtttgtt tctgtactgt ctcttctcaa gatgttgtct gttccccctg   9223

aaatttcata gtgagttgcc aaatttgaaa tgcaacaacc agctgtctgc atctggaacc   9283

tgtcaagcag tgctgtagtt tgaaaaagtt atgtgtgcat gtaaaatata cacatatata   9343

tatatacatt atacaagtat gtgcatgaaa tgtatatctt catacttttt gatacaatgt   9403

attcatttgt taatttttaa ttatatttga tataaattga aggtttgttg caaaaattta   9463

tatttaacag tgttgagaga gagagaaaga gcgagagagg gagagagaga gaaagatcca   9523

atcatgcaac agaaatggga ctactttaaa aatcagtcct ttgactagtt tgctgccctg   9583

aataatattt acaaaccaaa ctttggattc tgctcttgtt tctacaatga ctttttgtat   9643

aaagcaaagt ccttggatta ataaaacaac caaaaatcaa attaaaccat ta           9695
```

<210> SEQ ID NO 13
<211> LENGTH: 2333
<212> TYPE: PRT
<213> ORGANISM: Rattus norvegicus

<400> SEQUENCE: 13

```
Met Val Arg Phe Gly Asp Glu Leu Gly Gly Arg Tyr Gly Gly Thr Gly
 1               5                  10                  15

Gly Gly Glu Arg Ala Arg Gly Gly Gly Ala Gly Gly Ala Gly Gly Pro
            20                  25                  30

Gly Gln Gly Gly Leu Pro Pro Gly Gln Arg Val Leu Tyr Lys Gln Ser
        35                  40                  45

Ile Ala Gln Arg Ala Arg Thr Met Ala Leu Tyr Asn Pro Ile Pro Val
    50                  55                  60

Lys Gln Asn Cys Phe Thr Val Asn Arg Ser Leu Phe Val Phe Ser Glu
65                  70                  75                  80
```

-continued

```
Asp Asn Val Val Arg Lys Tyr Ala Lys Arg Ile Thr Glu Trp Pro Pro
                85                  90                  95

Phe Glu Tyr Met Ile Leu Ala Thr Ile Ile Ala Asn Cys Ile Val Leu
            100                 105                 110

Ala Leu Glu Gln His Leu Pro Asp Gly Asp Lys Thr Pro Met Ser Glu
        115                 120                 125

Arg Leu Asp Asp Thr Glu Pro Tyr Phe Ile Gly Ile Phe Cys Phe Glu
    130                 135                 140

Ala Gly Ile Lys Ile Ile Ala Leu Gly Phe Val Phe His Lys Gly Ser
145                 150                 155                 160

Tyr Leu Arg Asn Gly Trp Asn Val Met Asp Phe Val Val Val Leu Thr
                165                 170                 175

Gly Ile Leu Ala Thr Ala Gly Thr Asp Phe Asp Leu Arg Thr Leu Arg
            180                 185                 190

Ala Val Arg Val Leu Arg Pro Leu Lys Leu Val Ser Gly Ile Pro Ser
        195                 200                 205

Leu Gln Val Val Leu Lys Ser Ile Met Lys Ala Met Val Pro Leu Leu
    210                 215                 220

Gln Ile Gly Leu Leu Leu Phe Phe Ala Ile Leu Met Phe Ala Ile Ile
225                 230                 235                 240

Gly Leu Glu Phe Tyr Met Gly Lys Phe His Lys Ala Cys Phe Pro Asn
                245                 250                 255

Ser Thr Asp Ala Glu Pro Val Gly Asp Phe Pro Cys Gly Lys Glu Ala
            260                 265                 270

Pro Ala Arg Leu Cys Asp Ser Asp Thr Glu Cys Arg Glu Tyr Trp Pro
        275                 280                 285

Gly Pro Asn Phe Gly Ile Thr Asn Phe Asp Asn Ile Leu Phe Ala Ile
    290                 295                 300

Leu Thr Val Phe Gln Cys Ile Thr Met Glu Gly Trp Thr Asp Ile Leu
305                 310                 315                 320

Tyr Asn Thr Asn Asp Ala Ala Gly Asn Thr Trp Asn Trp Leu Tyr Phe
                325                 330                 335

Ile Pro Leu Ile Ile Ile Gly Ser Phe Phe Met Leu Asn Leu Val Leu
            340                 345                 350

Gly Val Leu Ser Gly Glu Phe Ala Lys Glu Arg Glu Arg Val Glu Asn
        355                 360                 365

Arg Arg Ala Phe Leu Lys Leu Arg Arg Gln Gln Gln Ile Glu Arg Glu
    370                 375                 380

Leu Asn Gly Tyr Leu Glu Trp Ile Phe Lys Ala Glu Glu Val Met Leu
385                 390                 395                 400

Ala Glu Glu Asp Lys Asn Ala Glu Glu Lys Ser Pro Leu Asp Val Leu
                405                 410                 415

Lys Arg Ala Ala Thr Lys Lys Ser Arg Asn Asp Leu Ile His Ala Glu
            420                 425                 430

Glu Gly Glu Asp Arg Phe Val Asp Leu Cys Ala Ala Gly Ser Pro Phe
        435                 440                 445

Ala Arg Ala Ser Leu Lys Ser Gly Lys Thr Glu Ser Ser Ser Tyr Phe
    450                 455                 460

Arg Arg Lys Glu Lys Met Phe Arg Phe Leu Ile Arg Arg Met Val Lys
465                 470                 475                 480

Ala Gln Ser Phe Tyr Trp Val Val Leu Cys Val Val Ala Leu Asn Thr
                485                 490                 495
```

-continued

```
Leu Cys Val Ala Met Val His Tyr Asn Gln Pro Gln Arg Leu Thr Thr
            500                 505                 510

Ala Leu Tyr Phe Ala Glu Phe Val Phe Leu Gly Leu Phe Leu Thr Glu
        515                 520                 525

Met Ser Leu Lys Met Tyr Gly Leu Gly Pro Arg Ser Tyr Phe Arg Ser
    530                 535                 540

Ser Phe Asn Cys Phe Asp Phe Gly Val Ile Val Gly Ser Ile Phe Glu
545                 550                 555                 560

Val Val Trp Ala Ala Ile Lys Pro Gly Thr Ser Phe Gly Ile Ser Val
                565                 570                 575

Leu Arg Ala Leu Arg Leu Leu Arg Ile Phe Lys Val Thr Lys Tyr Trp
            580                 585                 590

Asn Ser Leu Arg Asn Leu Val Val Ser Leu Leu Asn Ser Met Lys Ser
        595                 600                 605

Ile Ile Ser Leu Leu Phe Leu Leu Phe Leu Phe Ile Val Val Phe Ala
    610                 615                 620

Leu Leu Gly Met Gln Leu Phe Gly Gly Gln Phe Asn Phe Gln Asp Glu
625                 630                 635                 640

Thr Pro Thr Thr Asn Phe Asp Thr Phe Pro Ala Ala Ile Leu Thr Val
                645                 650                 655

Phe Gln Ile Leu Thr Gly Glu Asp Trp Asn Ala Val Met Tyr His Gly
            660                 665                 670

Ile Glu Ser Gln Gly Gly Val Ser Lys Gly Met Phe Ser Ser Phe Tyr
        675                 680                 685

Phe Ile Val Leu Thr Leu Phe Gly Asn Tyr Thr Leu Leu Asn Val Phe
    690                 695                 700

Leu Ala Ile Ala Val Asp Asn Leu Ala Asn Ala Gln Glu Leu Thr Lys
705                 710                 715                 720

Asp Glu Glu Glu Met Glu Glu Ala Ala Asn Gln Lys Leu Ala Leu Gln
                725                 730                 735

Lys Ala Lys Glu Val Ala Glu Val Ser Pro Met Ser Ala Ala Asn Ile
            740                 745                 750

Ser Ile Ala Ala Arg Gln Gln Asn Ser Ala Lys Ala Arg Ser Val Trp
        755                 760                 765

Glu Gln Arg Ala Ser Gln Leu Arg Leu Gln Asn Leu Arg Ala Ser Cys
    770                 775                 780

Glu Ala Leu Tyr Ser Glu Met Asp Pro Glu Glu Arg Leu Arg Tyr Ala
785                 790                 795                 800

Ser Thr Arg His Val Arg Pro Asp Met Lys Thr His Met Asp Arg Pro
                805                 810                 815

Leu Val Val Glu Pro Gly Arg Asp Gly Leu Arg Gly Pro Ala Gly Asn
            820                 825                 830

Lys Ser Lys Pro Glu Gly Thr Glu Ala Thr Glu Gly Ala Asp Pro Pro
        835                 840                 845

Arg Arg His His Arg His Arg Asp Arg Asp Lys Thr Ser Ala Ser Thr
    850                 855                 860

Pro Ala Gly Gly Glu Gln Asp Arg Thr Asp Cys Pro Lys Ala Glu Ser
865                 870                 875                 880

Thr Glu Thr Gly Ala Arg Glu Glu Arg Ala Arg Pro Arg Arg Ser His
                885                 890                 895

Ser Lys Glu Ala Pro Gly Ala Asp Thr Gln Val Arg Cys Glu Arg Ser
            900                 905                 910

Arg Arg His His Arg Arg Gly Ser Pro Glu Glu Ala Thr Glu Arg Glu
```

-continued

```
        915                 920                 925

Pro Arg Arg His Arg Ala His Arg His Ala Gln Asp Ser Ser Lys Glu
    930                 935                 940

Gly Lys Glu Gly Thr Ala Pro Val Leu Val Pro Lys Gly Glu Arg Arg
945                 950                 955                 960

Ala Arg His Arg Gly Pro Arg Thr Gly Pro Arg Glu Thr Glu Asn Ser
                965                 970                 975

Glu Glu Pro Thr Arg Arg His Arg Ala Lys His Lys Val Pro Pro Thr
            980                 985                 990

Leu Glu Pro Pro Glu Arg Glu Val Ala Glu Lys Glu Ser Asn Val Val
        995                1000                1005

Glu Gly Asp Lys Glu Thr Arg Asn His Gln Pro Lys Glu Pro Arg Cys
    1010                1015                1020

Asp Leu Glu Ala Ile Ala Val Thr Gly Val Gly Ser Leu His Met Leu
1025                1030                1035                1040

Pro Ser Thr Cys Leu Gln Lys Val Asp Glu Gln Pro Glu Asp Ala Asp
                1045                1050                1055

Asn Gln Arg Asn Val Thr Arg Met Gly Ser Gln Pro Ser Asp Pro Ser
            1060                1065                1070

Thr Thr Val His Val Pro Val Thr Leu Thr Gly Pro Pro Gly Glu Ala
        1075                1080                1085

Thr Val Val Pro Ser Ala Asn Thr Asp Leu Glu Gly Gln Ala Glu Gly
    1090                1095                1100

Lys Lys Glu Ala Glu Ala Asp Asp Val Leu Arg Arg Gly Pro Arg Pro
1105                1110                1115                1120

Ile Val Pro Tyr Ser Ser Met Phe Cys Leu Ser Pro Thr Asn Leu Leu
                1125                1130                1135

Arg Arg Phe Cys His Tyr Ile Val Thr Met Arg Tyr Phe Glu Met Val
            1140                1145                1150

Ile Leu Val Val Ile Ala Leu Ser Ser Ile Ala Leu Ala Ala Glu Asp
        1155                1160                1165

Pro Val Arg Thr Asp Ser Phe Arg Asn Asn Ala Leu Lys Tyr Met Asp
    1170                1175                1180

Tyr Ile Phe Thr Gly Val Phe Thr Phe Glu Met Val Ile Lys Met Ile
1185                1190                1195                1200

Asp Leu Gly Leu Leu Leu His Pro Gly Ala Tyr Phe Arg Asp Leu Trp
                1205                1210                1215

Asn Ile Leu Asp Phe Ile Val Val Ser Gly Ala Leu Val Ala Phe Ala
            1220                1225                1230

Phe Ser Gly Ser Lys Gly Lys Asp Ile Asn Thr Ile Lys Ser Leu Arg
        1235                1240                1245

Val Leu Arg Val Leu Arg Pro Leu Lys Thr Ile Lys Arg Leu Pro Lys
    1250                1255                1260

Leu Lys Ala Val Phe Asp Cys Val Val Asn Ser Leu Lys Asn Val Leu
1265                1270                1275                1280

Asn Ile Leu Ile Val Tyr Met Leu Phe Met Phe Ile Phe Ala Val Ile
                1285                1290                1295

Ala Val Gln Leu Phe Lys Gly Lys Phe Phe Tyr Cys Thr Asp Glu Ser
            1300                1305                1310

Lys Glu Leu Glu Arg Asp Cys Arg Gly Gln Tyr Leu Asp Tyr Glu Lys
        1315                1320                1325

Glu Glu Val Glu Ala Gln Pro Arg Gln Trp Lys Lys Tyr Asp Phe His
    1330                1335                1340
```

-continued

```
Tyr Asp Asn Val Leu Trp Ala Leu Leu Thr Leu Phe Thr Val Ser Thr
1345                1350                1355                1360

Gly Glu Gly Trp Pro Met Val Leu Lys His Ser Val Asp Ala Thr Tyr
                1365                1370                1375

Glu Glu Gln Gly Pro Ser Pro Gly Phe Arg Met Glu Leu Ser Ile Phe
            1380                1385                1390

Tyr Val Val Tyr Phe Val Val Phe Pro Phe Phe Phe Val Asn Ile Phe
        1395                1400                1405

Val Ala Leu Ile Ile Ile Thr Phe Gln Glu Gln Gly Asp Lys Val Met
    1410                1415                1420

Ser Glu Cys Ser Leu Glu Lys Asn Glu Arg Ala Cys Ile Asp Phe Ala
1425                1430                1435                1440

Ile Ser Ala Lys Pro Leu Thr Arg Tyr Met Pro Gln Asn Lys Gln Ser
                1445                1450                1455

Phe Gln Tyr Lys Thr Trp Thr Phe Val Val Ser Pro Pro Phe Glu Tyr
            1460                1465                1470

Phe Ile Met Ala Met Ile Ala Leu Asn Thr Val Val Leu Met Met Lys
        1475                1480                1485

Phe Tyr Asp Ala Pro Tyr Glu Tyr Glu Leu Met Leu Lys Cys Leu Asn
    1490                1495                1500

Ile Val Phe Thr Ser Met Phe Ser Leu Glu Cys Ile Leu Lys Ile Ile
1505                1510                1515                1520

Ala Phe Gly Val Leu Asn Tyr Phe Arg Asp Ala Trp Asn Val Phe Asp
                1525                1530                1535

Phe Val Thr Val Leu Gly Ser Ile Thr Asp Ile Leu Val Thr Glu Ile
            1540                1545                1550

Ala Glu Thr Asn Asn Phe Ile Asn Leu Ser Phe Leu Arg Leu Phe Arg
        1555                1560                1565

Ala Ala Arg Leu Ile Lys Leu Leu Arg Gln Gly Tyr Thr Ile Arg Ile
    1570                1575                1580

Leu Leu Trp Thr Phe Val Gln Ser Phe Lys Ala Leu Pro Tyr Val Cys
1585                1590                1595                1600

Leu Leu Ile Ala Met Leu Phe Phe Ile Tyr Ala Ile Ile Gly Met Gln
                1605                1610                1615

Val Phe Gly Asn Ile Ala Leu Asp Asp Gly Thr Ser Ile Asn Arg His
            1620                1625                1630

Asn Asn Phe Arg Thr Phe Leu Gln Ala Leu Met Leu Leu Phe Arg Ser
        1635                1640                1645

Ala Thr Gly Glu Ala Trp His Glu Ile Met Leu Ser Cys Leu Gly Asn
    1650                1655                1660

Arg Ala Cys Asp Pro His Ala Asn Ala Ser Glu Cys Gly Ser Asp Phe
1665                1670                1675                1680

Ala Tyr Phe Tyr Phe Val Ser Phe Ile Phe Leu Cys Ser Phe Leu Met
                1685                1690                1695

Leu Asn Leu Phe Val Ala Val Ile Met Asp Asn Phe Glu Tyr Leu Thr
            1700                1705                1710

Arg Asp Ser Ser Ile Leu Gly Pro His His Leu Asp Glu Phe Ile Arg
        1715                1720                1725

Val Trp Ala Glu Tyr Asp Pro Ala Ala Cys Gly Arg Ile Ser Tyr Asn
    1730                1735                1740

Asp Met Phe Glu Met Leu Lys His Met Ser Pro Pro Leu Gly Leu Gly
1745                1750                1755                1760
```

-continued

```
Lys Lys Cys Pro Ala Arg Val Ala Tyr Lys Arg Leu Val Arg Met Asn
                1765                1770                1775

Met Pro Ile Ser Asn Glu Asp Met Thr Val His Phe Thr Ser Thr Leu
            1780                1785                1790

Met Ala Leu Ile Arg Thr Ala Leu Glu Ile Lys Leu Ala Pro Ala Gly
        1795                1800                1805

Thr Lys Gln His Gln Cys Asp Ala Glu Leu Arg Lys Glu Ile Ser Ser
    1810                1815                1820

Val Trp Ala Asn Leu Pro Gln Lys Thr Leu Asp Leu Leu Val Pro Pro
1825                1830                1835                1840

His Lys Pro Asp Glu Met Thr Val Gly Lys Val Tyr Ala Ala Leu Met
                1845                1850                1855

Ile Phe Asp Phe Tyr Lys Gln Asn Lys Thr Thr Arg Asp Gln Thr His
            1860                1865                1870

Gln Ala Pro Gly Gly Leu Ser Gln Met Gly Pro Val Ser Leu Phe His
        1875                1880                1885

Pro Leu Lys Ala Thr Leu Glu Gln Thr Gln Pro Ala Val Leu Arg Gly
    1890                1895                1900

Ala Arg Val Phe Leu Arg Gln Lys Ser Ala Thr Ser Leu Ser Asn Gly
1905                1910                1915                1920

Gly Ala Ile Gln Thr Gln Glu Ser Gly Ile Lys Glu Ser Leu Ser Trp
                1925                1930                1935

Gly Thr Gln Arg Thr Gln Asp Val Leu Tyr Glu Ala Arg Ala Pro Leu
            1940                1945                1950

Glu Arg Gly His Ser Ala Glu Ile Pro Val Gly Gln Pro Gly Ala Leu
        1955                1960                1965

Ala Val Asp Val Gln Met Gln Asn Met Thr Leu Arg Gly Pro Asp Gly
    1970                1975                1980

Glu Pro Gln Pro Gly Leu Glu Ser Gln Gly Arg Ala Ala Ser Met Pro
1985                1990                1995                2000

Arg Leu Ala Ala Glu Thr Gln Pro Ala Pro Asn Ala Ser Pro Met Lys
                2005                2010                2015

Arg Ser Ile Ser Thr Leu Ala Pro Arg Pro His Gly Thr Gln Leu Cys
            2020                2025                2030

Asn Thr Val Leu Asp Arg Pro Pro Pro Ser Gln Val Ser His His His
        2035                2040                2045

His His Arg Cys His Arg Arg Arg Asp Lys Lys Gln Arg Ser Leu Glu
    2050                2055                2060

Lys Gly Pro Ser Leu Ser Val Asp Thr Glu Gly Ala Pro Ser Thr Ala
2065                2070                2075                2080

Ala Gly Ser Gly Leu Pro His Gly Glu Gly Ser Thr Gly Cys Arg Arg
                2085                2090                2095

Glu Arg Lys Gln Glu Arg Gly Arg Ser Gln Glu Arg Arg Gln Pro Ser
            2100                2105                2110

Ser Ser Ser Ser Glu Lys Gln Arg Phe Tyr Ser Cys Asp Arg Phe Gly
        2115                2120                2125

Ser Arg Glu Pro Pro Gln Pro Lys Pro Ser Leu Ser Ser His Pro Ile
    2130                2135                2140

Ser Pro Thr Ala Ala Leu Glu Pro Gly Pro His Pro Gln Gly Ser Gly
2145                2150                2155                2160

Ser Val Asn Gly Ser Pro Leu Met Ser Thr Ser Gly Ala Ser Thr Pro
                2165                2170                2175

Gly Arg Gly Gly Arg Arg Gln Leu Pro Gln Thr Pro Leu Thr Pro Arg
```

-continued

```
            2180                2185                2190

Pro Ser Ile Thr Tyr Lys Thr Ala Asn Ser Ser Pro Val His Phe Ala
        2195                2200                2205

Glu Gly Gln Ser Gly Leu Pro Ala Phe Ser Pro Gly Arg Leu Ser Arg
    2210                2215                2220

Gly Leu Ser Glu His Asn Ala Leu Leu Gln Lys Glu Pro Leu Ser Gln
2225                2230                2235                2240

Pro Leu Ala Ser Gly Ser Arg Ile Gly Ser Asp Pro Tyr Leu Gly Gln
                2245                2250                2255

Arg Leu Asp Ser Glu Ala Ser Ala His Asn Leu Pro Glu Asp Thr Leu
            2260                2265                2270

Thr Phe Glu Glu Ala Val Ala Thr Asn Ser Gly Arg Ser Ser Arg Thr
        2275                2280                2285

Ser Tyr Val Ser Ser Leu Thr Ser Gln Ser His Pro Leu Arg Arg Val
    2290                2295                2300

Pro Asn Gly Tyr His Cys Thr Leu Gly Leu Ser Thr Gly Val Arg Ala
2305                2310                2315                2320

Arg His Ser Tyr His His Pro Asp Gln Asp His Trp Cys
                2325                2330
```